(12) United States Patent
Vu

(10) Patent No.: US 11,963,953 B2
(45) Date of Patent: Apr. 23, 2024

(54) DEUTERATED COMPOUNDS FOR RESTORING MUTANT p53 FUNCTION

(71) Applicant: PMV Pharmaceuticals, Inc., Cranbury, NJ (US)

(72) Inventor: Binh Vu, North Caldwell, NJ (US)

(73) Assignee: PMV Pharmaceuticals, Inc., Princeton, NJ (US)

( * ) Notice: Subject to any disclaimer, the term of this patent is extended or adjusted under 35 U.S.C. 154(b) by 0 days.

(21) Appl. No.: 18/160,060

(22) Filed: Jan. 26, 2023

(65) Prior Publication Data

US 2023/0301975 A1    Sep. 28, 2023

Related U.S. Application Data

(60) Provisional application No. 63/303,535, filed on Jan. 27, 2022.

(51) Int. Cl.
*A61K 31/454*    (2006.01)

(52) U.S. Cl.
CPC ................... *A61K 31/454* (2013.01)

(58) Field of Classification Search
CPC .................................................. A61K 31/454
See application file for complete search history.

(56) References Cited

U.S. PATENT DOCUMENTS

| | | |
|---|---|---|
| 10,138,219 B2 | 11/2018 | Vu et al. |
| 10,640,485 B2 | 5/2020 | Vu et al. |
| 11,339,141 B2 | 5/2022 | Vu et al. |
| 2019/0002460 A1 | 1/2019 | Whitehead et al. |
| 2019/0119249 A1 | 4/2019 | Vu et al. |
| 2019/0284135 A1 | 9/2019 | Bonafoux et al. |
| 2022/0315564 A1 | 10/2022 | Vu et al. |
| 2023/0002403 A1 | 1/2023 | Vu et al. |
| 2023/0024905 A1 | 1/2023 | Vu et al. |
| 2023/0033324 A1 | 2/2023 | Levine et al. |
| 2023/0044826 A1 | 2/2023 | Dumble |
| 2023/0049952 A1 | 2/2023 | Levine et al. |

FOREIGN PATENT DOCUMENTS

| | | |
|---|---|---|
| CA | 3084777 A1 | 7/2019 |
| CN | 104672241 | 6/2015 |
| CN | 115504995 A | 12/2022 |
| WO | WO2012175962 A1 | 12/2012 |
| WO | WO-2016004513 A1 | 1/2016 |
| WO | WO-2018075937 A1 | 4/2018 |
| WO | WO-2018191587 A1 | 10/2018 |
| WO | WO-2021087096 A1 | 5/2021 |
| WO | WO-2022213975 A1 | 10/2022 |
| WO | WO-2023016434 A1 | 2/2023 |
| WO | WO-2023025324 A1 | 3/2023 |
| WO | WO-2023165523 A1 | 9/2023 |

OTHER PUBLICATIONS

Bilbao, et al., Two-Dimensional Nanoporous Networks Formed by Liquid-to-Solid Transfer of Hydrogen-Bonded Macrocycles Built from DNA Bases, 2015.
Dell'Acqua, et al., MediaChrom: Discovering a Class of Pyrimidoindolone-Based Polarity-Sensitive Dyes, 2015, Journal of Organic Chemistry, vol. 80 (21, pp. 10939-10954.
Fiandanese, et al., A straightforward synthesis of indole and benzofuran derivatives, 2007, Tetrahedron, Elsevier Science Publishers, vol. 64 (1), pp. 53-60.
Gergely, et al., C2-Selective Direct Alkynylation of Indoles, 2012, Organic Letters, vol. 15(1), pp. 112-115.
Guo, et al., PIM inhibitors target CD25-positive AML cells through concomitant suppression of STAT5 activation and degradation of MYC oncogene, 2014, Blood, vol. 124 (11), pp. 1777-1789.
Shinohara, et al., Design of environmentally sensitive fluorescent 2-deoxyguanosine containing arylethynyl moieties: Distenction of thymine base by base-discriminating fluorescent (BDF) probe, 2010, Bioorganic & Medicinal Chemistry Letters, vol. 20, pp. 2817-2820.
Database registry chemical abstracts service, Columbus, OH, Accession No. RN 1610707-41-9, Entered STN: Jun. 16, 2014.
Database registry chemical abstracts service, Columbus, OH, Accession No. RN 1511000-46-6, Entered STN: Jan. 5, 2014.
Database registry chemical abstracts service, Columbus, OH, Accession No. RN 1400286-50-1, Entered STN: Oct. 10, 2012.
Database registry chemical abstracts service, Columbus, OH, Accession No. RN 1336929-69-1, Entered STN: Oct. 17, 2011.
Coburn, CAPLUS abstract of WO2010111483.
Patani, G.A. et al., "Bioisosterism: A rational approach in drug design," Chemical Reviews, 1996;96:3147-3176.
International Search Report and Written Opinion issued in PCT/US2023/061374, dated Jul. 11, 2023.

*Primary Examiner* — Kamal A Saeed
(74) *Attorney, Agent, or Firm* — Wilson Sonsini Goodrich & Rosati

(57) ABSTRACT

The compounds of the current disclosure include propynyl substituted indoles, where one or more hydrido radicals is substituted with a deuterium atom, wherein the compound binds a mutant p53 protein and increases wild-type p53 activity of the mutant p53 protein.

33 Claims, No Drawings

Specification includes a Sequence Listing.

DEUTERATED COMPOUNDS FOR RESTORING MUTANT p53 FUNCTION

CROSS-REFERENCE

This application claims the benefit of U.S. Provisional Application No. 63/303,535, filed Jan. 27, 2022, which is incorporated by reference herein in its entirety.

SEQUENCE LISTING

The instant application contains a Sequence Listing, which has been submitted electronically in XML format and is hereby incorporated by reference in its entirety. Said XML copy, created on Jan. 26, 2023, is named 44727-721.201_SL.xml and is 3003 bytes in size.

BACKGROUND

Cancer, an uncontrolled proliferation of cells, is a multifactorial disease characterized by tumor formation, growth, and in some instances, metastasis. Cells carrying an activated oncogene, damaged genome, or other cancer-promoting alterations can be prevented from replicating through an elaborate tumor suppression network. A central component of this tumor suppression network is p53, one of the most potent tumor suppressors in the cell. Both the wild type and mutant conformations of p53 are implicated in the progression of cancer.

INCORPORATION BY REFERENCE

Each patent, publication, and non-patent literature cited in the application is hereby incorporated by reference in its entirety as if each was incorporated by reference individually.

SUMMARY OF THE DISCLOSURE

In some embodiments, described herein is a compound, the compound comprising: a propynyl substituted indolyl group, where one or more hydrido radicals is substituted with a deuterium atom, wherein the compound binds a mutant p53 protein and increases wild-type p53 activity of the mutant p53 protein.

In some embodiments, described herein is a composition comprising a population of molecules, wherein the population of molecules has a mass of at least 1 μg, wherein at least 10% of the molecules in the population of molecules each independently comprise a deuterium atom, wherein each molecule is a compound of Formula (Ia):

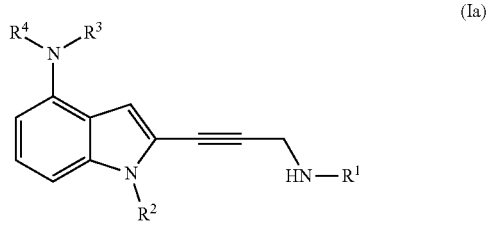

(Ia)

wherein:
R$^1$ is selected from aryl, heteroaryl, and heterocyclyl, each of which is independently unsubstituted or substituted with one, two or three substituents selected from a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, —P(O)R$^{21}$, and an ester group;

R$^2$ is alkyl, alkenyl, alkynyl, aryl, heteroaryl, or heterocyclyl, each of which is independently unsubstituted or substituted with one, two or three substituents selected from a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, —P(O)R$^{21}$, and an ester group; or hydrogen, —C(O)R$^{21}$, —C(O)OR$^{21}$, —C(O)NR$^{21}$R$^{22}$, —OR$^{21}$, —SR$^{21}$, —NR$^{21}$R$^{22}$, —NR$^{21}$C(O)R$^{22}$, or —OC(O)R$^{21}$;

R$^3$ is H;

R$^4$ is heterocyclyl substituted with one, two or three substituents selected from a halogen group, a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, —P(O)R$^{21}$, and an ester group; and each R$^{21}$ and R$^{22}$ is independently hydrido, alkyl, alkenyl, alkynyl, aryl, heteroaryl, or heterocyclyl, each of which is independently substituted or unsubstituted, or pharmaceutically acceptable salt thereof, wherein the compound is optionally substituted with at least one deuterium.

In some embodiments, described herein is a method of inducing apoptosis in a cell, the method comprising contacting the cell with a therapeutically-effective amount of a compound of the disclosure that binds a p53 mutant, wherein the compound increases the ability of the p53 mutant to bind DNA, wherein the cell expresses the p53 mutant.

In some embodiments, described herein is a method of treating a cancer, the method comprising administering to a subject in need thereof a therapeutically-effective amount of a compound of the disclosure.

In some embodiments, compounds are described that have improved metabolic stability.

DETAILED DESCRIPTION

The present disclosure provides compounds and methods for restoring wild-type function to mutant p53. The compounds of the present disclosure can bind to mutant p53 and restore the ability of the p53 mutant to bind DNA. The restoration of activity of the p53 mutant can allow for the activation of downstream effectors of p53 leading to inhibition of cancer progression. The disclosure further provides methods of treatment of a cancerous lesion or a tumor harboring a p53 mutation.

Cancer is a collection of related diseases characterized by uncontrolled proliferation of cells with the potential to metastasize throughout the body. Cancer can be classified into five broad categories including, for example: carcinomas, which can arise from cells that cover internal and external parts of the body such as the lung, breast, and colon; sarcomas, which can arise from cells that are located in bone, cartilage, fat, connective tissue, muscle, and other supportive tissues; lymphomas, which can arise in the lymph nodes and immune system tissues; leukemia, which can arise in the bone marrow and accumulate in the bloodstream; and adenomas, which can arise in the thyroid, the pituitary gland, the adrenal gland, and other glandular tissues.

Although different cancers can develop in virtually any of the body's tissues and contain unique features, the basic processes that cause cancer can be similar in all forms of the disease. Cancer begins when a cell breaks free from the normal restraints on cell division and begins to grow and divide out of control. Genetic mutations in the cell can preclude the ability of the cell to repair damaged DNA or initiate apoptosis, and can result in uncontrolled growth and division of cells.

The ability of tumor cell populations to multiply is determined not only by the rate of cell proliferation but also by the rate of cell attrition. Programmed cell death, or apoptosis, represents a major mechanism of cellular attrition. Cancer cells can evade apoptosis through a variety of strategies, for example, through the suppression of p53 function, thereby suppressing expression of pro-apoptotic proteins.

Oncogenes and tumor suppressor genes can regulate the proliferation of cells. Genetic mutations can affect oncogenes and tumor suppressors, potentially activating or suppressing activity abnormally, further facilitating uncontrolled cell division. Whereas oncogenes assist in cellular growth, tumor suppressor genes slow cell division by repairing damaged DNA and activating apoptosis. Cellular oncogenes that can be mutated in cancer include, for example, Cdk1, Cdk2, Cdk3, Cdk4, Cdk6, EGFR, PDGFR, VEGF, HER2, Raf kinase, K-Ras, and myc. Tumor suppressor genes that can be mutated in cancer include, for example, BRCA1, BRCA2, cyclin-dependent kinase inhibitor 1C, Retinoblastoma protein (pRb), PTEN, p16, p27, p53, and p73. Tumor suppressor p53.

The tumor suppressor protein p53 is a 393 amino acid transcription factor that can regulate cell growth in response to cellular stresses including, for example, UV radiation, hypoxia, oncogene activation, and DNA damage. p53 has various mechanisms for inhibiting the progression of cancer including, for example, initiation of apoptosis, maintenance of genomic stability, cell cycle arrest, induction of senescence, and inhibition of angiogenesis. Due to the critical role of p53 in tumor suppression, p53 is inactivated in almost all cancers either by direct mutation or through perturbation of associated signaling pathways involved in tumor suppression. Homozygous loss of the p53 gene occurs in almost all types of cancer, including carcinomas of the breast, colon, and lung. The presence of certain p53 mutations in several types of human cancer can correlate with less favorable patient prognosis.

In the absence of stress signals, p53 levels are maintained at low levels via the interaction of p53 with Mdm2, an E3 ubiquitin ligase. In an unstressed cell, Mdm2 can target p53 for degradation by the proteasome. Under stress conditions, the interaction between Mdm2 and p53 is disrupted, and p53 accumulates. The critical event leading to the activation of p53 is phosphorylation of the N-terminal domain of p53 by protein kinases, thereby transducing upstream stress signals. The phosphorylation of p53 leads to a conformational change, which can promote DNA binding by p53 and allow transcription of downstream effectors. The activation of p53 can induce, for example, the intrinsic apoptotic pathway, the extrinsic apoptotic pathway, cell cycle arrest, senescence, and DNA repair. p53 can activate proteins involved in the above pathways including, for example, Fas/Apol, KILLER/DR5, Bax, Puma, Noxa, Bid, caspase-3, caspase-6, caspase-7, caspase-8, caspase-9, and p21 (WAF1). Additionally, p53 can repress the transcription of a variety of genes including, for example, c-MYC, Cyclin B, VEGF, RAD51, and hTERT.

Each chain of the p53 tetramer is composed of several functional domains including the transactivation domain (amino acids 1-100), the DNA-binding domain (amino acids 101-306), and the tetramerization domain (amino acids 307-355), which are highly mobile and largely unstructured. Most p53 cancer mutations are located in the DNA-binding core domain of the protein, which contains a central b-sandwich of anti-parallel b-sheets that serves as a basic scaffold for the DNA-binding surface. The DNA-binding surface is composed of two b-turn loops, L2 and L3, which are stabilized by a zinc ion, for example, at Arg175 and Arg248, and a loop-sheet-helix motif. Altogether, these structural elements form an extended DNA-binding surface that is rich in positively-charged amino acids and makes specific contact with various p53 response elements.

Due to the prevalence of p53 mutations in virtually every type of cancer, the reactivation of wild type p53 function in a cancerous cell can be an effective therapy. Mutations in p53 located in the DNA-binding domain of the protein or periphery of the DNA-binding surface result in aberrant protein folding required for DNA recognition and binding. Mutations in p53 can occur, for example, at amino acids Val143, His168, Arg175, Tyr220, Gly245, Arg248, Arg249, Phe270, Arg273, and Arg282. p53 mutations that can abrogate the activity of p53 include, for example, R175H, Y220C, G245S, R248Q, R248W, R273H, and R282H. These p53 mutations can either distort the structure of the DNA-binding site or thermodynamically destabilize the folded protein at body temperature. Wild-type function of p53 mutants can be recovered by binding of the p53 mutant to a compound that can shift the folding-unfolding equilibrium towards the folded state, thereby reducing the rate of unfolding and destabilization.

Non-limiting examples of amino acids include: alanine (A, Ala); arginine (R, Arg); asparagine (N, Asn); aspartic acid (D, Asp); cysteine (C, Cys); glutamic acid (E, Glu); glutamine (Q, Gln); glycine (G, Gly); histidine (H, His); isoleucine (I, Ile); leucine (L, Leu); lysine (K, Lys); methionine (M, Met); phenylalanine (F, Phe); proline (P, Pro); serine (S, Ser); threonine (T, Thr); tryptophan (W, Trp); tyrosine (Y, Tyr); and valine (V, Val). Mechanism of compounds of the disclosure.

The compounds of the present disclosure can selectively bind to a p53 mutant and can recover wild-type activity of the p53 mutant including, for example, DNA binding function and activation of downstream targets involved in tumor suppression. In some embodiments, a compound of the disclosure selectively binds to the p53 Y220C mutant. The Y220C mutant is a temperature sensitive mutant, which binds to DNA at lower temperature and is denatured at body temperature. A compound of the disclosure can stabilize the Y220C mutant to reduce the likelihood of denaturation of the protein at body temperature.

Located in the periphery of the p53 b-sandwich connecting b-strands S7 and S8, the aromatic ring of Y220 is an integral part of the hydrophobic core of the b-sandwich. The Y220C mutation can be highly destabilizing, due to the formation of an internal surface cavity. A compound of the disclosure can bind to and occupy this surface crevice to stabilize the b-sandwich, thereby restoring wild-type p53 DNA-binding activity.

To determine the ability of a compound of the disclosure to bind and stabilize mutant p53, assays can be employed to detect, for example, a conformational change in the p53 mutant or activation of wild-type p53 targets. Conformational changes in p53 can be measured by, for example, differential scanning fluorimetry (DSF), isothermal titration calorimetry (ITC), nuclear magnetic resonance spectrometry (NMR), or X-ray crystallography. Additionally, antibodies specific for the wild type of mutant conformation of p53 can be used to detect a conformational change via, for example, immunoprecipitation (IP), immunofluorescence (IF), or immunoblotting.

Methods used to detect the ability of the p53 mutant to bind DNA can include, for example, DNA affinity immunoblotting, modified enzyme-linked immunosorbent assay (ELISA), electrophoretic mobility shift assay (EMSA), fluorescence resonance energy transfer (FRET), homogeneous time-resolved fluorescence (HTRF), and a chromatin immunoprecipitation (ChIP) assay.

To determine whether a compound described herein is able to reactivate the transcriptional activity of p53, the activation of downstream targets in the p53 signaling cascade can be measured. Activation of p53 effector proteins can be detected by, for example, immunohistochemistry (IHC-P), reverse transcription polymerase chain reaction (RT-PCR), and western blotting. The activation of p53 can also be measured by the induction of apoptosis via the caspase cascade and using methods including, for example, Annexin V staining, TUNEL assays, pro-caspase and caspase levels, and cytochrome c levels. Another consequence of p53 activation is senescence, which can be measured using methods such as b-galactosidase staining.

A p53 mutant that can be used to determine the effectiveness of a compound of the disclosure to increase the DNA binding ability of a p53 mutant is a p53 truncation mutant, which contains only amino acids 94-312, encompassing the DNA-binding domain of p53. For example, the sequence of the p53 Y220C mutant used for testing compound efficacy can be:

```
                                        (SEQ ID NO. 1)
SSSVPSQ KTYQGSYGFR LGFLHSGTAK SVTCTYSPAL

NKMFCQLAKT CPVQLWVDST PPPGTRVRAM AIYKQSQHMT

EVVRRCPHHE RCSDSDGLAP PQHLIRVEGN LRVEYLDDRN

TFRHSVVVPC EPPEVGSDCT TIHYNYMCNS SCMGGMNRRP

ILTIITLEDS SGNLLGRNSF EVHVCACPGR DRRTEEENLR

KKGEPHHELP PGSTKRALSN NT
```

A compound of the disclosure can increase the ability of a p53 mutant to bind DNA by at least or up to about 0.1%, at least or up to about 0.2%, at least or up to about 0.3%, at least or up to about 0.4%, at least or up to about 0.5%, at least or up to about 0.6%, at least or up to about 0.7%, at least or up to about 0.8%, at least or up to about 0.9%, at least or up to about 1%, at least or up to about 2%, at least or up to about 3%, at least or up to about 4%, at least or up to about 5%, at least or up to about 6%, at least or up to about 7%, at least or up to about 8%, at least or up to about 9%, at least or up to about 10%, at least or up to about 11%, at least or up to about 12%, at least or up to about 13%, at least or up to about 14%, at least or up to about 15%, at least or up to about 16%, at least or up to about 17%, at least or up to about 18%, at least or up to about 19%, at least or up to about 20%, at least or up to about 21%, at least or up to about 22%, at least or up to about 23%, at least or up to about 24%, at least or up to about 25%, at least or up to about 26%, at least or up to about 27%, at least or up to about 28%, at least or up to about 29%, at least or up to about 30%, at least or up to about 31%, at least or up to about 32%, at least or up to about 33%, at least or up to about 34%, at least or up to about 35%, at least or up to about 36%, at least or up to about 37%, at least or up to about 38%, at least or up to about 39%, at least or up to about 40%, at least or up to about 41%, at least or up to about 42%, at least or up to about 43%, at least or up to about 44%, at least or up to about 45%, at least or up to about 46%, at least or up to about 47%, at least or up to about 48%, at least or up to about 49%, at least or up to about 50%, at least or up to about 51%, at least or up to about 52%, at least or up to about 53%, at least or up to about 54%, at least or up to about 55%, at least or up to about 56%, at least or up to about 57%, at least or up to about 58%, at least or up to about 59%, at least or up to about 60%, at least or up to about 61%, at least or up to about 62%, at least or up to about 63%, at least or up to about 64%, at least or up to about 65%, at least or up to about 66%, at least or up to about 67%, at least or up to about 68%, at least or up to about 69%, at least or up to about 70%, at least or up to about 71%, at least or up to about 72%, at least or up to about 73%, at least or up to about 74%, at least or up to about 75%, at least or up to about 76%, at least or up to about 77%, at least or up to about 78%, at least or up to about 79%, at least or up to about 80%, at least or up to about 81%, at least or up to about 82%, at least or up to about 83%, at least or up to about 84%, at least or up to about 85%, at least or up to about 86%, at least or up to about 87%, at least or up to about 88%, at least or up to about 89%, at least or up to about 90%, at least or up to about 91%, at least or up to about 92%, at least or up to about 93%, at least or up to about 94%, at least or up to about 95%, at least or up to about 96%, at least or up to about 97%, at least or up to about 98%, at least or up to about 99%, at least or up to about 100%, at least or up to about 125%, at least or up to about 150%, at least or up to about 175%, at least or up to about 200%, at least or up to about 225%, or at least or up to about 250% as compared to the ability of the p53 mutant to bind DNA in the absence of a compound of the disclosure.

A compound described herein can increase the activity of the p53 mutant that is, for example, at least or up to about 2-fold, at least or up to about 3-fold, at least or up to about 4-fold, at least or up to about 5-fold, at least or up to about 6-fold, at least or up to about 7-fold, at least or up to about 8-fold, at least or up to about 9-fold, at least or up to about 10-fold, at least or up to about 11-fold, at least or up to about 12-fold, at least or up to about 13-fold, at least or up to about 14-fold, at least or up to about 15-fold, at least or up to about 16-fold, at least or up to about 17-fold, at least or up to about 18-fold, at least or up to about 19-fold, at least or up to about 20-fold, at least or up to about 25-fold, at least or up to about 30-fold, at least or up to about 35-fold, at least or up to about 40-fold, at least or up to about 45-fold, at least or up to about 50-fold, at least or up to about 55-fold, at least or up to about 60-fold, at least or up to about 65-fold, at least or up to about 70-fold, at least or up to about 75-fold, at least or up to about 80-fold, at least or up to about 85-fold, at least or up to about 90-fold, at least or up to about 95-fold, at least or up to about 100-fold, at least or up to about 110-fold, at least or up to about 120-fold, at least or up to about 130-fold, at least or up to about 140-fold, at least or up to about 150-fold, at least or up to about 160-fold, at least or up to about 170-fold, at least or up to about 180-fold, at least or up to about 190-fold, at least or up to about 200-fold, at least or up to about 250-fold, at least or up to about 300-fold, at least or up to about 350-fold, at least or up to about 400-fold, at least or up to about 450-fold, at least or up to about 500-fold, at least or up to about 550-fold, at least or up to about 600-fold, at least or up to about 650-fold, at least or up to about 700-fold, at least or up to about 750-fold, at least or up to about 800-fold, at least or up to about 850-fold, at least or up to about 900-fold, at least or up to about 950-fold, at least or up to about 1,000-fold, at least or up to about 1,500-fold, at least or up to about 2,000-fold, at least or up to about 3,000-fold, at least or up to about 4,000-fold, at least or up to about 5,000-fold, at least or up to about 6,000-fold, at least or up to about 7,000-fold, at least or up to about 8,000-fold, at least or up to about 9,000-fold, or at least or up to about 10,000-fold greater than the activity of the p53 mutant in the absence of the compound.

A compound of the disclosure can be used, for example, to induce apoptosis, cell cycle arrest, or senescence in a cell. In some embodiments, the cell is a cancer cell. In some embodiments, the cell carries a mutation in p53.

Compounds of the Disclosure

In some embodiments, compounds comprise one or more isotopically enriched atoms. For example, compounds having a hydrogen atom is replaced by a deuterium or deuterio group [D], are within the scope of this is selected from disclosure.

Isotopically-labeled compounds of the present disclosure can generally be prepared by conventional techniques known to those skilled in the art or by processes analogous to those described in the accompanying Examples and Preparations using an appropriate isotopically-labeled reagent in place of the non-labeled reagent previously employed.

In some embodiments, the disclosure provides a composition comprising a population of molecules, wherein the population of molecules has a mass of at least 1 μg, wherein at least 10% of the molecules in the population of molecules each independently comprise a deuterium atom, wherein each molecule is a compound of formula:

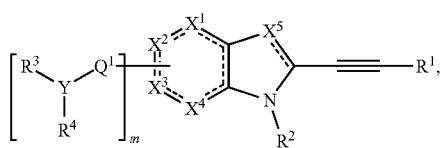

wherein:
each ------- is independently a single bond or a double bond;
$X^1$ is $CR^5$, $CR^5R^6$, N, $NR^5$, O, S, C=O, C=S, or a carbon atom connected to $Q^1$;
$X^2$ is $CR^7$, $CR^7R^8$, N, $NR^7$, O, S, C=O, C=S, or a carbon atom connected to $Q^1$;
$X^3$ is $CR^9$, $CR^9R^{10}$, N, $NR^9$, O, S, C=O, C=S, or a carbon atom connected to $Q^1$;
$X^4$ is $CR^{11}$, $CR^{11}R^{12}$, N, $NR^{11}$, 0, S, C=O, C=S, or a carbon atom connected to $Q^1$;
$X^5$ is $CR^{13}$, N, or $NR^{13}$;
wherein at least one of $X^1$, $X^2$, $X^3$, and $X^4$ is a carbon atom connected to $Q^1$;
$Q^1$ is alkylene, alkenylene, or alkynylene, each of which is independently substituted or unsubstituted, or C=O, C=S, C=$CR^{14}R^{15}$, C=$NR^{14}$, or a bond;
m is 1, 2, 3, or 4;
Y is N;
$R^1$ is alkyl, alkenyl, alkynyl, aryl, heteroaryl, or heterocyclyl, each of which is independently substituted or unsubstituted, or —C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, —OC(O)$R^{16}$, —CN, —Si$R^{16}R^{17}R^{18}$, or hydrogen;
each $R^3$ and $R^4$ is independently, alkyl, alkylene, alkenyl, alkenylene, alkynyl, aryl, heteroaryl, or heterocyclyl, each of which is independently substituted or unsubstituted, or —C(O)$R^{19}$, —C(O)O$R^{19}$, —C(O)N$R^{19}R^{20}$, —SO$R^{19}$, —SO$^2R^{19}$, or hydrogen, or $R^3$ and $R^4$ together with the nitrogen atom to which $R^3$ and $R^4$ are bound form a ring, wherein the ring is substituted or unsubstituted;
each $R^2$, $R^5$, $R^6$, $R^7$, $R^8$, $R^9$, $R^{10}$, $R^{11}$, $R^{12}$, $R^{13}$, $R^{14}$, $R^1$, $R^{16}$, $R^{17}$, and $R^{18}$ is independently alkyl, alkenyl, alkynyl, aryl, heteroaryl, or heterocyclyl, each of which is independently substituted or unsubstituted, or —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, —OC(O)$R^{21}$, hydrogen, or halogen;
each $R^{19}$ and $R^{20}$ is alkyl, alkenyl, alkynyl, aryl, heteroaryl, or heterocyclyl, each of which is independently substituted or unsubstituted, or C(O)$R^{23}$, —C(O)O$R^{23}$, —C(O)N$R^{23}R^{24}$, —O$R^{23}$, —S$R^{23}$, —N$R^{23}R^{24}$, —N$R^{23}$C(O)$R^{24}$, —OC(O)$R^{23}$, hydrogen, or halogen;
each $R^{21}$ and $R^{22}$ is independently alkyl, alkenyl, alkynyl, aryl, heteroaryl, or heterocyclyl, each of which is independently substituted or unsubstituted, or hydrogen; and
each $R^{23}$ and $R^{24}$ is independently alkyl, alkenyl, alkynyl, aryl, heteroaryl, or heterocyclyl, each of which is independently substituted or unsubstituted, or hydrogen, or a pharmaceutically-acceptable salt thereof, wherein the compound is optionally substituted with at least one deuterio [D] group.

In some embodiments, $Q^1$ is a bond. In some embodiments, $Q^1$ is $C_1$-alkylene. In some embodiments, m is 1. In some embodiments, m is 2. In some embodiments, m is 3.

In some embodiments, the pattern of dashed bonds is chosen to provide an aromatic system, for example, an indole, an indolene, a pyrrolopyridine, a pyrrolopyrimidine, or a pyrrolopyrazine.

In some embodiments, $X^1$ is $CR^5$, $CR^5R^6$, or a carbon atom connected to $Q^1$. In some embodiments, $X^2$ is $CR^7$, $CR^7R^8$, or a carbon atom connected to $Q^1$. In some embodiments, $X^3$ is $CR^9$, $CR^9R^{10}$, or a carbon atom connected to $Q^1$. In some embodiments, $X^4$ is $CR^{11}$, $CR^{11}R^{12}$, or a carbon atom connected to $Q^1$. In some embodiments, $X^5$ is $CR^{13}$, N, or $NR^{13}$. In some embodiments, $X^1$ is a carbon atom connected to $Q^1$. In some embodiments, $X^2$ is a carbon atom connected to $Q^1$. In some embodiments, $X^3$ is a carbon atom connected to $Q^1$. In some embodiments, $X^4$ is a carbon atom connected to $Q^1$. In some embodiments, $X^5$ is N.

In some embodiments, the disclosure provides a composition comprising a population of molecules, wherein the population of molecules has a mass of at least 1 μg, wherein at least 10% of the molecules in the population of molecules each independently comprise a deuterium atom, wherein each molecule is a compound of Formula (I'):

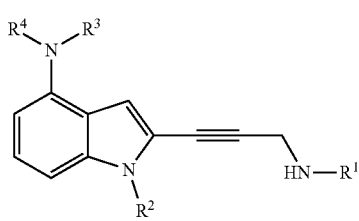

(I')

wherein:
- $R^1$ is selected from aryl, heteroaryl, and heterocyclyl, each of which is independently unsubstituted or substituted with one, two or three substituents selected from a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, —P(O)$R^{21}$, and an ester group; —$R^2$ is alkyl, alkenyl, alkynyl, aryl, heteroaryl, or heterocyclyl, each of which is independently unsubstituted or substituted with one, two or three substituents selected from a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, —P(O)$R^{21}$, and an ester group; or hydrogen, —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, or —OC(O)$R^{21}$; —$R^3$ is H;
- —$R^4$ is heterocyclyl substituted with one, two or three substituents selected from a halogen group, a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, —P(O)$R^{21}$, and an ester group;
- each $R^{21}$ and $R^{22}$ is independently hydrido, alkyl, alkenyl, alkynyl, aryl, heteroaryl, or heterocyclyl, each of which is independently substituted or unsubstituted, or a pharmaceutically-acceptable salt thereof,
- wherein the compound is optionally substituted with at least one deuterium atom.

In some embodiments, the disclosure provides a composition comprising a population of molecules, wherein the population of molecules has a mass of at least 1 μg, wherein at least 10% of the molecules in the population of molecules each independently comprise a deuterium atom, wherein each molecule is a compound of Formula (I):

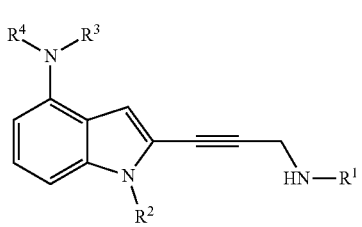

(I)

wherein:
- $R^1$ is selected from aryl, heteroaryl, and heterocyclyl, each of which is independently unsubstituted or substituted with one, two or three substituents selected from a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, —P(O)$R^{21}$, and an ester group;
- $R^2$ is alkyl, alkenyl, alkynyl, aryl, heteroaryl, or heterocyclyl, each of which is independently unsubstituted or substituted with one, two or three substituents selected from a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, —P(O)$R^{21}$, and an ester group; or hydrido, —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, or —OC(O)$R^{21}$;
- $R^3$ is H;
- $R^4$ is heterocyclyl substituted with one, two or three substituents selected from a halogen group, a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, —P(O)$R^{21}$, and an ester group; and
- each $R^{21}$ and $R^{22}$ is independently hydrido, alkyl, alkenyl, alkynyl, aryl, heteroaryl, or heterocyclyl, each of which is independently substituted or unsubstituted, or a pharmaceutically acceptable salt thereof,
wherein the compound is optionally substituted with least one deuterio [D] group.

In some embodiments, $R^1$ is aryl, independently substituted with one, two, or three substituents selected from alkylsulfonyl, alkoxy, alkylaminocarbonyl, deuterated alkoxy, and (deuterated alkyl)aminocarbonyl.

In some embodiments, $R^1$ is phenyl independently substituted with one, two, or three substituents selected from $C_{1-4}$ alkylsulfonyl, $C_{1-4}$ alkoxy, $C_{1-4}$ alkylaminocarbonyl, deuterated $C_{1-4}$ alkoxy, and (deuterated $C_{1-4}$ alkyl)aminocarbonyl.

In some embodiments, $R^1$ is phenyl independently substituted with one, two, or three substituents selected from the group consisting of methylsulfonyl, methoxy, methylaminocarbonyl, trideuteriomethoxy, and (trideuteriomethyl) aminocarbonyl.

In some embodiments, $R^2$ is alkyl, unsubstituted or substituted with halo.

In some embodiments, $R^2$ is $C_{1-4}$ haloalkyl.

In some embodiments, $R^2$ is 1,1,1-trifluoroethyl.

In some embodiments, $R^4$ is 4-piperidinyl unsubstituted or substituted with one, two or three substituents selected from halo, $C_{1-4}$ alkyl, and $C_{1-4}$ alkoxy-(hydroxy)-$C_{1-4}$ alkyl;

In some embodiments, $R^4$ is 4-piperidinyl substituted with fluoro and one or two additional substituents selected from methyl, trideuteriomethyl, tert-butyl, 2-hydroxy-methoxypropyl and 2-hydroxy-trideuteriomethoxypropyl.

In some embodiments, the disclosure provides a composition comprising a population of molecules, wherein the population of molecules has a mass of at least 1 μg, wherein each molecule is a compound of Formula (II):

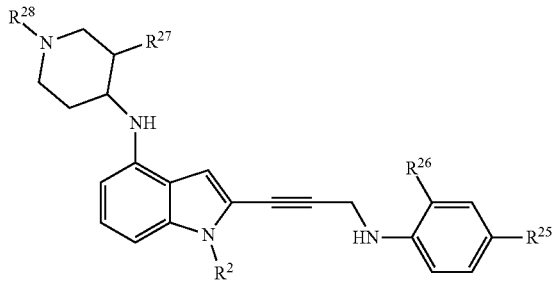

(II)

wherein:
$R^2$ is $C_1$-$C_4$ haloalkyl,
$R^{25}$ is selected from hydrido, a hydroxyl group, sulfhydryl group, halogen, amino group, nitro group, nitroso group, cyano group, azido group, sulfoxide group, alkyl sulfonyl group, sulfonamide group, carboxyl group, carboxaldehyde group, imine group, alkyl group, halo-alkyl group, alkenyl group, halo-alkenyl group, alkynyl group, halo-alkynyl group, alkoxy group, deuterated alkoxy group, aryl group, aryloxy group, aralkyl group, arylalkoxy group, heterocyclyl group, acyl group, acyloxy group, carbamate group, amide group, deuterated alkyl amide group, ureido group, epoxy group, —P(O)$R^{21}$, and an ester group;
$R^{26}$ is selected from hydrido, a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, alkenyl group, halo-alkenyl group, alkynyl group, halo-alkynyl group, alkoxy group, deuterated alkoxy group, aryl group, aryloxy group, aralkyl group, arylalkoxy group, heterocyclyl group, acyl group, acyloxy group, carbamate group, amide group, deuterated amide group, ureido group, epoxy group, —P(O)$R^{21}$, and an ester group;

$R^{27}$ is selected from hydrido, substituted with a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, —P(O)$R^{21}$, and an ester group; and $R^{28}$ is selected from hydrido, a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, deuterated alkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, —P(O)$R^{21}$, and an ester group, or a pharmaceutically-acceptable salt thereof;

provided that in at least 10% of the population of molecules, one or more of $R^{25}$, $R^{26}$, $R^{27}$ or $R^{28}$ independently comprises a deuterated group.

In some embodiments, $R^2$ is 1,1,1-trifluoroethyl; $R^{25}$ is selected from $C_1$-$C_4$ alkylaminocarbonyl, deuterated $C_1$-$C_4$ alkylaminocarbonyl or $C_1$-$C_4$ alkylsulfonyl; $R^{26}$ is $C_1$-$C_4$ alkoxy, or deuterated $C_1$-$C_4$ alkoxy; $R^{27}$ is hydrido, or fluoro; and $R^{28}$ is selected from $C_1$-$C_4$ alkyl, deuterated $C_1$-$C_4$ alkyl, optionally hydroxy substituted $C_1$-$C_4$ alkoxy-$C_1$-$C_4$ alkyl, or optionally hydroxy substituted deuterated $C_1$-$C_4$ alkoxy-$C_1$-$C_4$ alkyl.

In some embodiments, $R^{25}$ is methylsuflonyl, methylaminocarbonyl, or trideuteriomethylaminocarbonyl; $R^{26}$ is methoxy, or trideuteriomethoxy; and $R^{28}$ is selected from methyl, tert-butyl, deuterated methyl, 2-hydroxy-1-methoxypropyl, or 1-trideuteriomethoxy-2-hydroxypropyl.

Non-limiting examples of compounds of the current disclosure include the following:

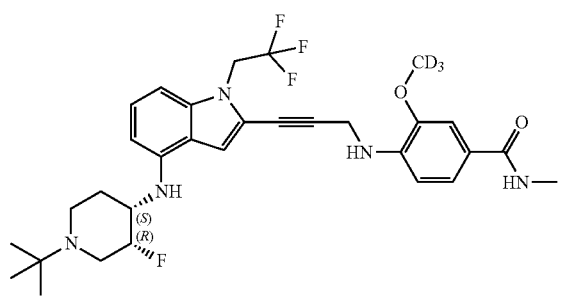

-continued
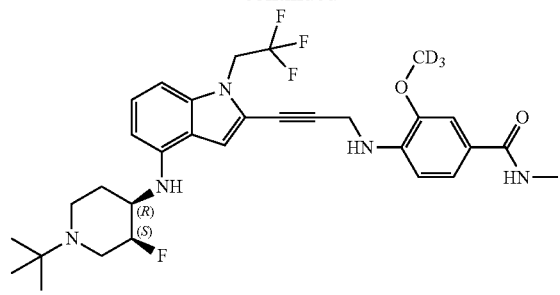
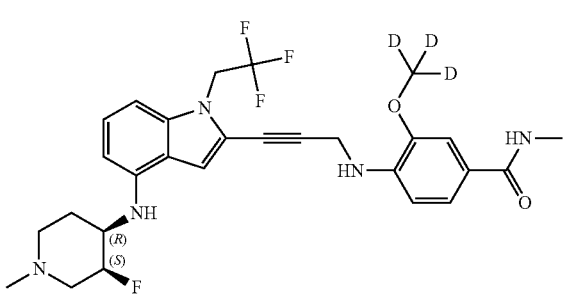
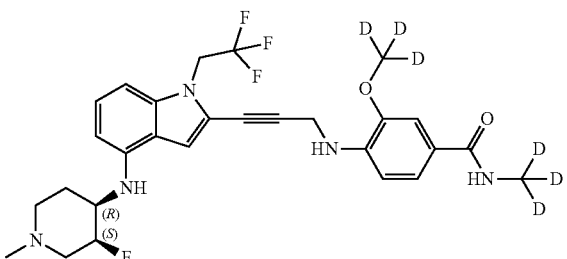
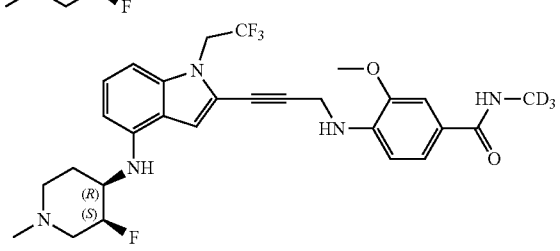
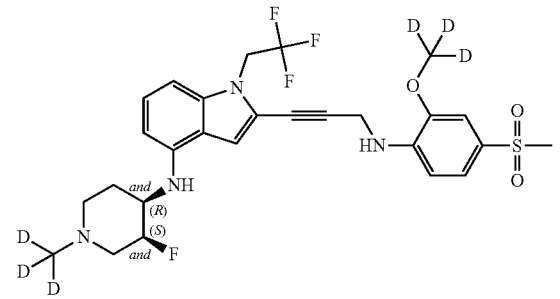
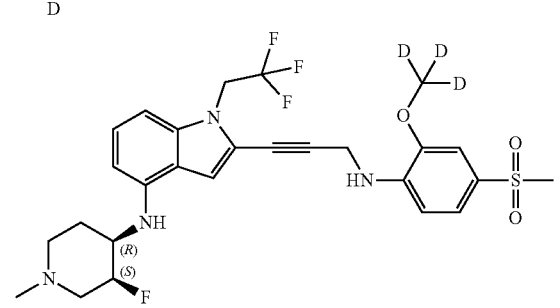
-continued
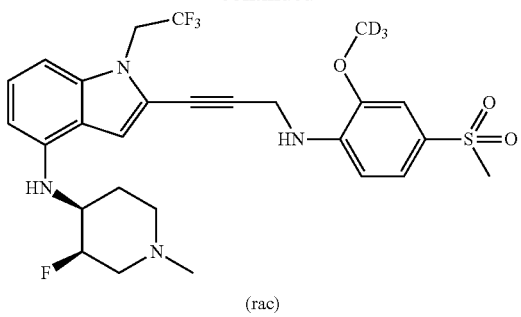
(rac)
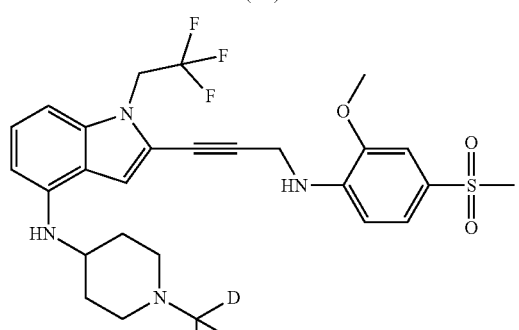
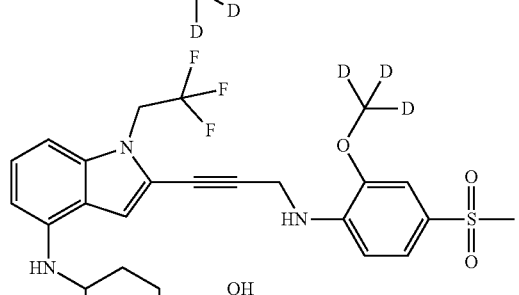
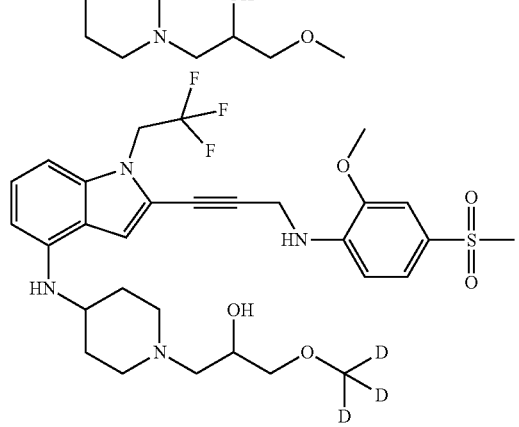
and
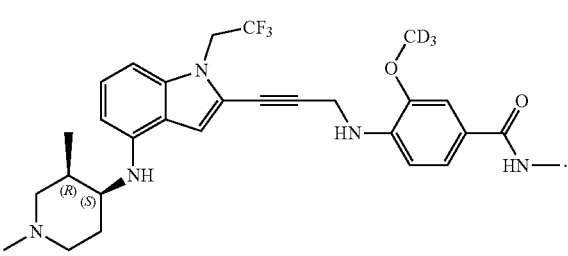
Non-limiting examples of compounds of the current disclosure include the following:

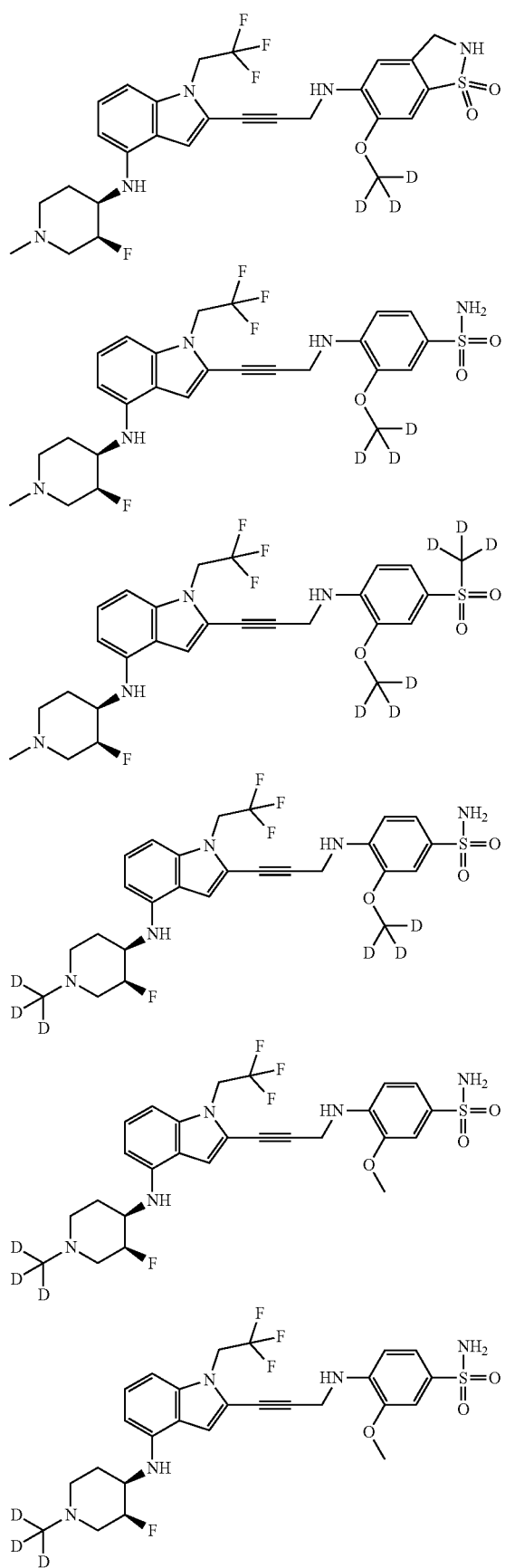

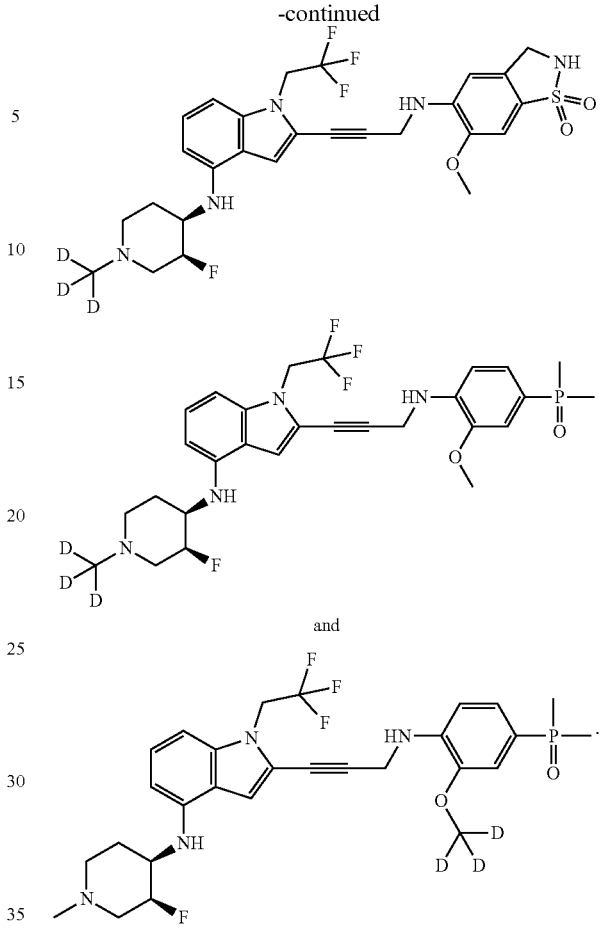

and

Compounds herein can include all stereoisomers, enantiomers, diastereomers, mixtures, racemates, atropisomers, and tautomers thereof.

In some instances, a deuterated compound of the disclosure provides a plasma $AUC_{0-24}$ in primates that is greater than a plasma $AUC_{0-24}$ in primates of an analogous compound, wherein the analogous compound is identical to the deuterated compound except that the analogous compound bears hydrogen atoms in place of deuterium atoms. In some embodiments, the analogous compound is compound C:

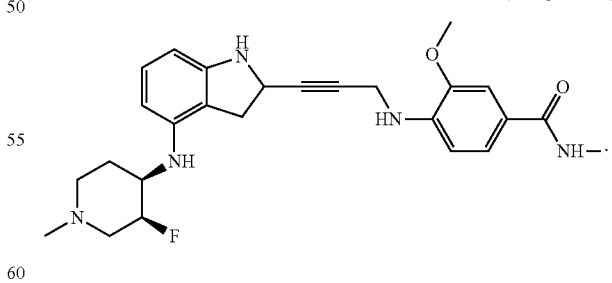

(Compound C)

In some instances, the deuterated compound has improved exposure relative to the exposure exhibited by the analogous compound. In some embodiments, the $AUC_{0-24}$ of the deuterated compound is about 10% greater, about 20% greater, about 30% greater, about 40% greater, about 50% greater, about 60% greater or about 70% greater than that observed for the analogous compound.

A deuterated compound of the disclosure can undergo glucuronidation in primates at a rate that is less than the rate of glucuronidation in primates of an analogous compound, wherein the analogous compound is identical to the deuterated compound except that the analogous compound bears hydrogen atoms in place of deuterium atoms. In some instances, the rate of glucuronidation in primates of the deuterated compound is about 10%, about 20%, about 30%, about 40%, about 50%, about 60% or about 70% of the rate of glucuronidation in primates of the analogous compound.

Non-limiting examples of optional substituents include hydroxyl groups, sulfhydryl groups, halogens, amino groups, nitro groups, nitroso groups, cyano groups, azido groups, sulfoxide groups, sulfone groups, sulfonamide groups, carboxyl groups, carboxaldehyde groups, imine groups, alkyl groups, halo-alkyl groups, alkenyl groups, halo-alkenyl groups, alkynyl groups, halo-alkynyl groups, alkoxy groups, aryl groups, aryloxy groups, aralkyl groups, arylalkoxy groups, heterocyclyl groups, acyl groups, acyloxy groups, carbamate groups, amide groups, ureido groups, epoxy groups, —P(O)$R^A$, and ester groups, wherein $R^A$ is hydrido, alkyl, alkenyl, alkynyl, aryl, heteroaryl, or heterocyclyl.

Non-limiting examples of alkyl and alkylene groups include straight, branched, and cyclic alkyl and alkylene groups. An alkyl or alkylene group can be, for example, a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted. Non-limiting examples of alkyl can be $C_{1-4}$-alkyl.

Non-limiting examples of straight alkyl groups include methyl, ethyl, propyl, butyl, pentyl, hexyl, heptyl, octyl, nonyl, and decyl. Branched alkyl groups include any straight alkyl group substituted with any number of alkyl groups. Non-limiting examples of branched alkyl groups include isopropyl, isobutyl, sec-butyl, and t-butyl. Non-limiting examples of substituted alkyl groups includes hydroxymethyl, chloromethyl, trifluoromethyl, aminomethyl, 1-chloroethyl, 2-hydroxyethyl, 1,2-difluoroethyl, and 3-carboxypropyl. Non-limiting examples of cyclic alkyl groups include cyclopropyl, cyclobutyl, cyclopentyl, cyclohexyl, cycloheptlyl, and cyclooctyl groups. Cyclic alkyl groups also include fused-, bridged-, and spiro-bicycles and higher fused-, bridged-, and spiro-systems. A cyclic alkyl group can be substituted with any number of straight, branched, or cyclic alkyl groups. Non-limiting examples of cyclic alkyl groups include cyclopropyl, 2-methyl-cycloprop-1-yl, cycloprop-2-en-1-yl, cyclobutyl, 2,3-dihydroxycyclobut-1-yl, cyclobut-2-en-1-yl, cyclopentyl, cyclopent-2-en-1-yl, cyclopenta-2,4-dien-1-yl, cyclohexyl, cyclohex-2-en-1-yl, cycloheptyl, cyclooctanyl, 2,5-dimethylcyclopent-1-yl, 3,5-dichlorocyclohex-1-yl, 4-hydroxycyclohex-1-yl, 3,3,5-trimethylcyclohex-1-yl, octahydropentalenyl, octahydro-1H-indenyl, 3a,4,5,6,7,7a-hexahydro-3H-inden-4-yl, decahydroazulenyl, bicyclo[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

Non-limiting examples of deuterated alkyl includes mono-deuterated, di-deuterated, tri-deuterated through per-deuterated alkyl.

Non-limiting examples of alkenyl and alkenylene groups include straight, branched, and cyclic alkenyl groups. The olefin or olefins of an alkenyl group can be, for example, E, Z, cis, trans, terminal, or exo-methylene. An alkenyl or alkenylene group can be, for example, a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted. Non-limiting examples of alkenyl and alkenylene groups include ethenyl, prop-1-en-1-yl, isopropenyl, but-1-en-4-yl; 2-chloroethenyl, 4-hydroxybuten-1-yl, 7-hydroxy-7-methyloct-4-en-2-yl, and 7-hydroxy-7-methyloct-3,5-dien-2-yl.

Non-limiting examples of alkynyl or alkynylene groups include straight, branched, and cyclic alkynyl groups. The triple bond of an alkylnyl or alkynylene group can be internal or terminal. An alkylnyl or alkynylene group can be, for example, a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted. Non-limiting examples of alkynyl or alkynylene groups include ethynyl, prop-2-yn-1-yl, prop-1-yn-1-yl, and 2-methyl-hex-4-yn-1-yl; 5-hydroxy-5-methylhex-3-yn-1-yl, 6-hydroxy-6-methylhept-3-yn-2-yl, and 5-hydroxy-5-ethylhept-3-yn-1-yl.

A halo-alkyl group can be any alkyl group substituted with any number of halogen atoms, for example, fluorine, chlorine, bromine, and iodine atoms. Non-limiting examples of halo alkyl can be $C_{1-4}$-haloalkyl. A halo-alkenyl group can be any alkenyl group substituted with any number of halogen atoms. A halo-alkynyl group can be any alkynyl group substituted with any number of halogen atoms.

An alkoxy group can be, for example, an oxygen atom substituted with any alkyl, alkenyl, or alkynyl group. Non-limiting examples of alkoxy can be $C_{1-4}$-alkoxy. An ether or an ether group comprises an alkoxy group. Non-limiting examples of alkoxy groups include methoxy, ethoxy, propoxy, isopropoxy, and isobutoxy. Non-limiting examples of deuterated alkyl includes monodeuterated, dideuterated, tri deuterated through perdeuterated alkyl.

An alkylsulfonyl group can be, for example, a sulfonyl group [—$SO_2$—] substituted with any alkyl. Non-limiting examples of alkylsulfonyl can be $C_{1-4}$ alkylsulfonyl, e.g. methylsulfonyl.

An alkylaminocarbonyl group can be, for example, an aminocarbonyl {—$NHCO_2$—} substituted with any alkyl. Non-limiting examples of alkylaminocarbonyl can be $C_{1-4}$ alkylaminocarbonyl, e.g. methylaminocarbonyl.

An aryl group can be heterocyclic or non-heterocyclic. An aryl group can be monocyclic or polycyclic. An aryl group can be substituted with any number of substituents described herein, for example, hydrocarbyl groups, alkyl groups, alkoxy groups, and halogen atoms. Non-limiting examples of aryl groups include phenyl, toluyl, naphthyl, pyrrolyl, pyridyl, imidazolyl, thiophenyl, and furyl. Non-limiting examples of substituted aryl groups include 3,4-dimethylphenyl, 4-tert-butylphenyl, 4-cyclopropylphenyl, 4-diethylaminophenyl, 4-(trifluoromethyl)phenyl, 4-(difluoromethoxy)-phenyl, 4-(trifluoromethoxy)phenyl, 3-chlorophenyl, 4-chlorophenyl, 3,4-dichlorophenyl, 2-fluorophenyl, 2-chlorophenyl, 2-iodophenyl, 3-iodophenyl, 4-iodophenyl, 2-methylphenyl, 3-fluorophenyl, 3-methylphenyl, 3-methoxyphenyl, 4-fluorophenyl, 4-methylphenyl, 4-methoxyphenyl, 2,3-difluorophenyl, 3,4-difluorophenyl, 3,5-difluorophenyl, 2,3-dichlorophenyl, 3,4-dichlorophenyl, 3,5-dichlorophenyl, 2-hydroxyphenyl, 3-hydroxyphenyl, 4-hydroxyphenyl, 2-methoxyphenyl, 3-methoxyphenyl, 4-methoxyphenyl, 2,3-dimethoxyphenyl, 3,4-dimethoxyphenyl, 3,5-dimethoxyphenyl, 2,4-difluorophenyl, 2,5-difluorophenyl, 2,6-difluorophenyl, 2,3,4-trifluorophenyl, 2,3,5-trifluorophenyl, 2,3,6-trifluorophenyl, 2,4,5-trifluorophenyl, 2,4,6-trifluorophenyl, 2,4-dichlorophenyl, 2,5-dichlorophenyl, 2,6-dichlorophenyl, 3,4-dichlorophenyl, 2,3,4-trichlorophenyl, 2,3,5-trichlorophenyl, 2,3,6-trichlorophenyl, 2,4,5-trichlorophenyl, 3,4,5-trichlorophenyl, 2,4,6-trichlorophenyl, 2,3-dimethylphenyl, 2,4-dimethylphenyl, 2,5-dimethylphenyl, 2,6-dimethylphenyl, 2,3,4-trimethylphenyl, 2,3,5-trimethylphenyl, 2,3,6-trimethylphenyl, 2,4,5-trimethylphenyl, 2,4,6-trimethylphenyl, 2-ethylphenyl, 3-ethylphenyl, 4-ethylphenyl, 2,3-diethylphenyl, 2,4-diethylphenyl, 2,5-diethylphenyl, 2,6-diethylphenyl, 3,4-diethylphenyl, 2,3,4-triethylphenyl, 2,3,5-triethylphenyl, 2,3,6-triethylphenyl, 2,4,5-triethylphenyl, 2,4,6-triethylphenyl, 2-isopropylphenyl, 3-isopropylphenyl, and 4-isopropylphenyl. Non-limiting examples of substituted aryl groups include 2-aminophenyl, 2-(N-methylamino)phenyl, 2-(N,N-dimethylamino)phenyl, 2-(N-ethylamino)phenyl, 2-(N,N-diethylamino)phenyl, 3-aminophenyl, 3-(N-methylamino)phenyl, 3-(N,N-dimethylamino)phenyl, 3-(N-ethylamino)phenyl, 3-(N,N-diethylamino)phenyl, 4-aminophenyl, 4-(N-methylamino)phenyl, 4-(N,N-dimethylamino)phenyl, 4-(N-ethylamino)phenyl, and 4-(N,N-diethylamino)phenyl.

A heterocycle can be any ring containing a ring atom that is not carbon, for example, N, O, S, P, Si, B, or any other heteroatom. A heterocycle can be substituted with any number of substituents, for example, alkyl groups and halogen atoms. A heterocycle can be aromatic (heteroaryl) or non-aromatic. Non-limiting examples of heterocycles include pyrrole, pyrrolidine, pyridine, piperidine, succinimide, maleimide, morpholine, imidazole, thiophene, furan, tetrahydrofuran, pyran, and tetrahydropyran.

Non-limiting examples of heterocycles include: heterocyclic units having a single ring containing one or more heteroatoms, non-limiting examples of which include, diazirinyl, aziridinyl, azetidinyl, pyrazolidinyl, imidazolidinyl, oxazolidinyl, isoxazolinyl, thiazolidinyl, isothiazolinyl, oxathiazolidinonyl, oxazolidinonyl, hydantoinyl, tetrahydrofuranyl, pyrrolidinyl, morpholinyl, piperazinyl, piperidinyl, dihydropyranyl, tetrahydropyranyl, piperidin-2-onyl, 2,3,4,5-tetrahydro-1H-azepinyl, 2,3-dihydro-1H-indole, and 1,2,3,4-tetrahydroquinoline; and ii) heterocyclic units having 2 or more rings one of which is a heterocyclic ring, non-limiting examples of which include hexahydro-1H-pyrrolizinyl, 3a,4,5,6,7,7a-hexahydro-1H-benzo[d]imidazolyl, 3a,4,5,6,7,7a-hexahydro-1H-indolyl, 1,2,3,4-tetrahydroquinolinyl, and decahydro-1H-cycloocta[b]pyrrolyl.

Non-limiting examples of heteroaryl include: i) heteroaryl rings containing a single ring, non-limiting examples of which include, 1,2,3,4-tetrazolyl, [1,2,3]triazolyl, [1,2,4]triazolyl, triazinyl, thiazolyl, 1H-imidazolyl, oxazolyl, isoxazolyl, isothiazolyl, furanyl, thiophenyl, pyrimidinyl, 2-phenylpyrimidinyl, pyridinyl, 3-methylpyridinyl, and 4-dimethylaminopyridinyl; and ii) heteroaryl rings containing 2 or more fused rings one of which is a heteroaryl ring, non-limiting examples of which include: 7H-purinyl, 9H-purinyl, 6-amino-9H-purinyl, 5H-pyrrolo[3,2-d]pyrimidinyl, 7H-pyrrolo[2,3-d]pyrimidinyl, pyrido[2,3-d]pyrimidinyl, 4,5,6,7-tetrahydro-1-H-indolyl, quinoxalinyl, quinazolinyl, quinolinyl, 8-hydroxy-quinolinyl, and isoquinolinyl.

Any compound herein can be purified. A compound herein can be least 1% pure, at least 2% pure, at least 3% pure, at least 4% pure, at least 5% pure, at least 6% pure, at least 7% pure, at least 8% pure, at least 9% pure, at least 10% pure, at least 11% pure, at least 12% pure, at least 13% pure, at least 14% pure, at least 15% pure, at least 16% pure, at least 17% pure, at least 18% pure, at least 19% pure, at least 20% pure, at least 21% pure, at least 22% pure, at least 23% pure, at least 24% pure, at least 25% pure, at least 26% pure, at least 27% pure, at least 28% pure, at least 29% pure, at least 30% pure, at least 31% pure, at least 32% pure, at least 33% pure, at least 34% pure, at least 35% pure, at least 36% pure, at least 37% pure, at least 38% pure, at least 39% pure, at least 40% pure, at least 41% pure, at least 42% pure, at least 43% pure, at least 44% pure, at least 45% pure, at least 46% pure, at least 47% pure, at least 48% pure, at least 49% pure, at least 50% pure, at least 51% pure, at least 52% pure, at least 53% pure, at least 54% pure, at least 55% pure, at least 56% pure, at least 57% pure, at least 58% pure, at least 59% pure, at least 60% pure, at least 61% pure, at least 62% pure, at least 63% pure, at least 64% pure, at least 65% pure, at least 66% pure, at least 67% pure, at least 68% pure, at least 69% pure, at least 70% pure, at least 71% pure, at least 72% pure, at least 73% pure, at least 74% pure, at least 75% pure, at least 76% pure, at least 77% pure, at least 78% pure, at least 79% pure, at least 80% pure, at least 81% pure, at least 82% pure, at least 83% pure, at least 84% pure, at least 85% pure, at least 86% pure, at least 87% pure, at least 88% pure, at least 89% pure, at least 90% pure, at least 91% pure, at least 92% pure, at least 93% pure, at least 94% pure, at least 95% pure, at least 96% pure, at least 97% pure, at least 98% pure, at least 99% pure, at least 99.1% pure, at least 99.2% pure, at least 99.3% pure, at least 99.4% pure, at least 99.5% pure, at least 99.6% pure, at least 99.7% pure, at least 99.8% pure, or at least 99.9% pure.

In some embodiments, disclosed herein is a method of treating a cancer, the method comprising administering to a subject in need thereof a therapeutically-effective amount of a compound of the disclosure. A compound of the disclosure can, for example, slow the proliferation of cancer cell lines, or kill cancer cells. Non-limiting examples of cancer that can be treated by a compound of the disclosure include: acute lymphoblastic leukemia, acute myeloid leukemia, adrenocortical carcinoma, AIDS-related cancers, AIDS-related lymphoma, anal cancer, appendix cancer, astrocytomas, basal cell carcinoma, bile duct cancer, bladder cancer, bone cancers, brain tumors, such as cerebellar astrocytoma, cerebral astrocytoma/malignant glioma, ependymoma, medulloblastoma, supratentorial primitive neuroectodermal tumors, visual pathway and hypothalamic glioma, breast cancer, bronchial adenomas, Burkitt lymphoma, carcinoma of unknown primary origin, central nervous system lymphoma, cerebellar astrocytoma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma, germ cell tumors, gallbladder cancer, gastric cancer, gastrointestinal carcinoid tumor, gastrointestinal stromal tumor, gliomas, hairy cell leukemia, head and neck cancer, heart cancer, hepatocellular (liver) cancer, Hodgkin lymphoma, Hypopharyngeal cancer, intraocular melanoma, islet cell carcinoma, Kaposi sarcoma, kidney cancer, laryngeal cancer, lip and oral cavity cancer, liposarcoma, liver cancer, lung cancers, such as non-small cell and small cell lung cancer, lymphomas, leukemias, macroglobulinemia, malignant fibrous histiocytoma of bone/osteosarcoma, medulloblastoma, melanomas, mesothelioma, metastatic squamous neck cancer with occult primary, mouth cancer, multiple endocrine neoplasia syndrome, myelodysplastic syndromes, myeloid leukemia, nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer, ovarian germ cell tumor, pancreatic cancer, pancreatic cancer islet cell, paranasal sinus and nasal cavity cancer, parathyroid cancer, penile cancer, pharyngeal cancer, pheochromocytoma, pineal astrocytoma, pineal germinoma, pituitary adenoma, pleuropulmonary blastoma, plasma cell neoplasia, primary central nervous system lymphoma, prostate cancer, rectal cancer, renal cell carcinoma, renal pelvis and ureter transitional cell cancer, retinoblastoma, rhabdomyosarcoma, salivary gland cancer, sarcomas, skin cancers, skin carcinoma merkel cell, small intestine cancer, soft tissue sarcoma, squamous cell carcinoma, stomach cancer, T-cell lymphoma, throat cancer, thymoma, thymic carcinoma, thyroid cancer, trophoblastic tumor (gestational), cancers of unknown primary site, urethral cancer, uterine sarcoma, vaginal cancer, vulvar cancer, Waldenström macroglobulinemia, and Wilms tumor.

In some embodiments, the compounds of the disclosure show non-lethal toxicity.

In some embodiments, disclosed herein is a method of treating cancer comprising administering to a subject in need thereof a pharmaceutical composition of the disclosure. In some embodiments, the pharmaceutical composition comprises a population of molecules, wherein the population of molecules has a mass of at least 1 µg, wherein at least 10% of the molecules in the population of molecules each independently comprise a deuterium atom, wherein each molecule is a compound of Formula (I):

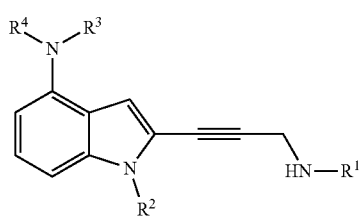

(I)

wherein:
$R^1$ is selected from aryl, heteroaryl, and heterocyclyl, each of which is independently unsubstituted or substituted with one, two or three substituents selected from a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, —P(O)$R^{21}$, and an ester group;
$R^2$ is alkyl, alkenyl, alkynyl, aryl, heteroaryl, or heterocyclyl, each of which is independently unsubstituted or substituted with one, two or three substituents selected from a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, and an ester group; or hydrogen, —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, or —OC(O)$R^{21}$;
$R^3$ is H;
$R^4$ is heterocyclyl substituted with one, two or three substituents selected from a halogen group, a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, and an ester group; and
each $R^{21}$ and $R^{22}$ is independently hydrido, alkyl, alkenyl, alkynyl, aryl, heteroaryl, or heterocyclyl, each of which is independently substituted or unsubstituted;
or a pharmaceutically-acceptable salt thereof,
wherein the compound is optionally substituted with at least one deuterium atom, and the compound has an $SC_{150}$ value for p53 Y220C of less than 1 mM as measured by a homogeneous time-resolved fluorescence (HTRF) assay.

In some embodiments, disclosed herein is a method of inducing apoptosis in a cell, the method comprising contacting the cell with a therapeutically-effective amount of a pharmaceutical composition disclosed herein. In some embodiments, disclosed herein is a method of inducing apoptosis in a cell, the method comprising contacting the cell with a therapeutically-effective amount of a compound that binds a p53 mutant, wherein the compound is a compound disclosed herein. In some embodiments, the compound increases the ability of the p53 mutant to bind DNA. In some embodiments, the cell expresses the p53. In some embodiments, the p53 mutant has a mutation at amino acid 220. In some embodiments, the p53 mutant is p53 Y220C. In some embodiments, the compound induces a conformational change in the p53 mutant. In some embodiments, the compound selectively binds the p53 mutant as compared to a wild type p53. In some embodiments, the therapeutically effective amount is from about 50 mg to about 3000 mg. In some embodiments, the compound increases a stability of a biologically active conformation of the p53 mutant relative to a stability of the biologically active conformation of the p53 mutant in an absence of the compound.

Unless otherwise stated, when a position in a specific or generic formula of the present disclosure (e.g., Compound 1 or Formula (I)) is designated implicitly or explicitly as "H" or "hydrogen", in a composition containing a plurality of molecules where each molecule is independently a compound according to the formula, the proportion of the plurality of molecules that have hydrogen at the position is equal to the natural isotopic abundance of hydrogen at the position. However, in some embodiments, where specifically stated, when a position is designated specifically as "H" or "hydrogen", the proportion of the plurality of molecules that have deuterium at the position is <5 mol %, <4 mol %, <3 mol %, <2 mol %, or <1 mol %.

In some embodiments, when a position in a specific or generic formula of the present disclosure (e.g., Compound 1 or Formula (I)) is designated as "D" or "deuterium", in a composition containing a plurality of molecules where each molecule is independently a compound according to the formula, the proportion of the plurality of compounds that have deuterium at the position is at least 3000 times greater than the natural abundance of deuterium (i.e., at least 45 mol %); at least 3500 times greater than the natural abundance of deuterium (at least 52.5 mol %), at least 4500 times greater than the natural abundance of deuterium (at least 67.5 mol %), at least 5000 (at least 75 mol %), at least 5500 times greater than the natural abundance of deuterium (at least 82.5 mol %), at least 6000 times greater than the natural abundance of deuterium (at least 90 mol %), at least 6333.3 times greater than the natural abundance of deuterium (at least 95 mol %), at least 6466.7 times greater than the natural abundance of deuterium (at least 97 mol %), at least 6600 times greater than the natural abundance of deuterium (at least 99 mol %), or at least 6633.3 times greater than the natural abundance of deuterium (at least 99.5 mol %).

In some embodiments, when a position in a specific or generic formula of the present disclosure (e.g., Compound 1 or Formula (I)) is designated as "D" or "deuterium", in a composition containing a plurality of molecules where each molecule is independently a compound according to the formula, the proportion of the plurality of molecules that have deuterium at the position is at least about 10 mol %, at least about 25 mol %, at least about 50 mol %, at least about 75 mol %, at least about 80 mol %, at least about 82.5 mol %, at least about 85 mol %, at least about 87.5 mol %, at least about 90 mol %, at least about 92.5 mol %, at least about 95 mol %, at least about 96 mol %, at least about 97 mol %, at least about 98 mol %, at least about 99 mol %, or at least about 99.5 mol %.

The term "isotopic enrichment factor" at a particular position normally occupied by hydrogen means the ratio between the abundance of deuterium at the position and the natural abundance of hydrogen at that position. By way of example, an isotopic enrichment factor of 3500 means that the amount of deuterium at the particular position is 3500 fold greater than natural abundance, or that 52.5% of the compounds have deuterium at the particular position (i.e., 52.5% deuterium incorporation at the given position).

When a particular position in a compound of the present disclosure is designated by name or structure as containing hydrogen or deuterium, it is to be understood that the position can contain hydrogen at its natural abundance or can be enriched in deuterium with an isotopic enrichment factor of, for example, at least 835 (13% deuterium incorporation), of at least 1670 (26% deuterium incorporation, of at least 3500 (52.5% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

"Substituted with deuterium" refers to the replacement of one or more hydrogen atoms with a corresponding number of deuterium atoms.

Mass Spectroscopy.

Different methods for obtaining a mass spectrometer signal are known in the art. In various implementations, mass spectrometric analysis includes ionizing one or more compounds to generate charged molecules or molecule fragments and measuring their mass-to-charge ratios (cf. Sparkman, O. D. (2000). Mass spectrometry desk reference. Pittsburgh: Global View Pub. ISBN 0-9660813-2-3). Such procedures can include the following steps: loading a mixture containing one or more compounds onto the MS instrument and vaporizing the one or more compounds; ionizing the components of the mixture, to form charged particles (ions); electromagnetically separating the ions according to their mass-to-charge ratio in an analyzer; detecting the ions (e.g., by a quantitative method); and transforming the ion signals into mass spectra.

The mass spectrometer can be operated, for example, in any of the following modes: (1) full scan, e.g., the mass spectrometer detects all ions between two distant points on the m/z scale (such as 0 and 10000); (2) Single Ion Monitoring (SIM) or Single Ion Recording (SIR), e.g., the mass spectrometer detects only ions which have a particular m/z value or which lie within a small m/z range (e.g., a range of 1 or 2 mass units); (3) Multiple Reaction Monitoring (MRM), e.g., in a mass spectrometer having multiple mass spectrometer units, at least two units are operated in the SIMI/SIR mode.

After separation and measurement of the intensities of the ions in the mass spectrometer, mass spectra are created, for example by plotting the intensities measured for the detected ions vs. their mass-to-charge ratio (m/z). Depending on the mode by which the mass spectrometer is operated (full scan, SIMI/SIR, or MRM), the mass spectra can include (1) the peaks corresponding to all ions (precursor and product ions) detected in the mass spectrometer between two distant points on the m/z scale; (2) the peaks corresponding to (a) all ions which have a particular m/z value or which lie within a very small mass m/z range and optionally (b) all product ions derived from the ions specified under (a); or (3) only one or more selected product/daughter ions (MRM channels).

For example, when the mass spectrometer is operated in MRM mode, one can create a single mass spectrum for a deuterated analog and corresponding target analyte. The single mass spectrum will contain one peak for each analog and, if present in the sample, one peak for the corresponding target analyte. Alternatively, multiple mass spectra can be created for each analog and each corresponding target analyte, where each of the multiple mass spectra only represents one analog or target analyte. Such single mass spectrum or multiple mass spectra can be created for each analog and corresponding target analyte (e.g., in a panel).

Mass spectra created using MRM channels and where peak intensities are plotted against time (such as retention time if the mass spectrometer is coupled to a SPE, chromatography, or electrophoresis device) are often described as mass chromatograms. Thus, the term mass spectra, as used herein, can also relate to mass chromatograms (e.g., where the MS operates in MRM mode).

Next, the MS signal intensities (or relative signal intensities) of the ions representative of each of the target analyte(s) and corresponding analog(s) are determined. The signal intensities of the ions in the mass spectra (e.g., the intensities of the peaks corresponding to these ions) can be determined on the basis of the peak height or peak area, for example on the basis of peak area such as by integrating the signal intensity of a specific ion with respect to time. The intensities of the ions signals in the mass spectrum/spectra can be normalized e.g., to 100%, to the most intense ion signal detected.

The mass spectrometer (as well as the mass spectrometers of any of the methods of the disclosure) can be essentially any instrument that includes an ionization source, an analyzer, and a detector suitable for producing mass spectra. The mass spectrometer may contain multiple mass spectrometer units (MSn where n=2, 3, 4 . . . ) and/or can be coupled to other instruments, such as a chromatography or electrophoresis device (e.g., a separation system, for example in LC/MS/MS).

The mass spectrometer can include an ion source such as an Electrospray ionization ("ESI") ion source; an Atmospheric Pressure Photo Ionization ("APPI") ion source; an Atmospheric Pressure Chemical Ionization ("APCI") ion source; a Matrix Assisted Laser Desorption Ionization ("MALDI") ion source; a Laser Desorption Ionization ("LDI") ion source; an Atmospheric Pressure Ionization ("API") ion source; a Desorption Ionization on Silicon ("DIOS") ion source; an Electron Impact ("EI") ion source; a Chemical Ionization ("CI") ion source; a Field Ionization ("FI") ion source; a Field Desorption ("FD") ion source; an Inductively Coupled Plasma ("ICP") ion source; a Fast Atom Bombardment ("FAB") ion source; a Liquid Secondary Ion Mass Spectrometry ("LSIMS") ion source; a Desorption Electrospray Ionization ("DESI") ion source; a Nickel-63 radioactive ion source; an Atmospheric Pressure Matrix Assisted Laser Desorption Ionization ion source; and a Thermo spray ion source.

The mass spectrometer can include a mass analyzer such as a quadrupole mass analyzer; a 2D or linear quadrupole mass analyzer; a Paul or 3D quadrupole mass analyzer; a 2D or linear quadrupole ion trap mass analyzer; a Paul or 3D quadrupole ion trap mass analyzer; a Penning trap mass analyzer; an ion trap mass analyzer; a magnetic sector mass analyzer; Ion Cyclotron Resonance ("ICR") mass analyzer; a Fourier Transform Ion Cyclotron Resonance ("FTICR") mass analyzer; an electrostatic or orbitrap mass analyzer; a Fourier Transform electrostatic or orbitrap mass analyzer; a Fourier Transform mass analyzer; a Time of Flight mass analyzer; an orthogonal acceleration Time of Flight mass analyzer; and a linear acceleration Time of Flight mass analyzer. The mass spectrometer can include an ion mobility analyzer.

The mass spectrometer can include an ionization source such as an Electrospray ionization ("ESI") ion source; an Atmospheric Pressure Photo Ionization ("APPI") ion source; an Atmospheric Pressure Chemical Ionization ("APCI") ion source; a Matrix Assisted Laser Desorption Ionization ("MALDI") ion source; a Laser Desorption Ionization ("LDI") ion source; an Atmospheric Pressure Ionization ("API") ion source; a Desorption Ionization on Silicon ("DIOS") ion source; an Electron Impact ("EI") ion source; a Chemical Ionization ("CI") ion source; a Field Ionization ("FI") ion source; a Field Desorption ("FD") ion source; an Inductively Coupled Plasma ("ICP") ion source; a Fast Atom Bombardment ("FAB") ion source; a Liquid Secondary Ion Mass Spectrometry ("LSIMS") ion source; a Desorption Electrospray Ionization ("DESI") ion source; a Nickel-63 radioactive ion source; an Atmospheric Pressure Matrix Assisted Laser Desorption Ionization ion source; and a Thermo spray ion source.

Pharmaceutically-Acceptable Salts.

The present disclosure provides the use of pharmaceutically-acceptable salts of any therapeutic compound described herein. Pharmaceutically-acceptable salts include, for example, acid-addition salts and base-addition salts. The acid that is added to the compound to form an acid-addition salt can be an organic acid or an inorganic acid. A base that is added to the compound to form a base-addition salt can be an organic base or an inorganic base. In some embodiments, a pharmaceutically-acceptable salt is a metal salt. In some embodiments, a pharmaceutically-acceptable salt is an ammonium salt.

Metal salts can arise from the addition of an inorganic base to a compound of the disclosure. The inorganic base consists of a metal cation paired with a basic counterion, such as, for example, hydroxide, carbonate, bicarbonate, or phosphate. The metal can be an alkali metal, alkaline earth metal, transition metal, or main group metal. In some embodiments, the metal is lithium, sodium, potassium, cesium, cerium, magnesium, manganese, iron, calcium, strontium, cobalt, titanium, aluminum, copper, cadmium, or zinc.

In some embodiments, a metal salt is a lithium salt, a sodium salt, a potassium salt, a cesium salt, a cerium salt, a magnesium salt, a manganese salt, an iron salt, a calcium salt, a strontium salt, a cobalt salt, a titanium salt, an aluminum salt, a copper salt, a cadmium salt, or a zinc salt.

Ammonium salts can arise from the addition of ammonia or an organic amine to a compound of the disclosure. In some embodiments, the organic amine is triethyl amine, diisopropyl amine, ethanol amine, diethanol amine, triethanol amine, morpholine, N-methylmorpholine, piperidine, N-methylpiperidine, N-ethylpiperidine, dibenzylamine, piperazine, pyridine, pyrazole, pipyrrazole, imidazole, pyrazine, or piperazine.

In some embodiments, an ammonium salt is a triethyl amine salt, a diisopropyl amine salt, an ethanol amine salt, a diethanol amine salt, a triethanol amine salt, a morpholine salt, an N-methylmorpholine salt, a piperidine salt, an N-methylpiperidine salt, an N-ethylpiperidine salt, a dibenzylamine salt, a piperazine salt, a pyridine salt, a pyrazole salt, a pipyrrazole salt, an imidazole salt, a pyrazine salt, or a piperazine salt.

Acid addition salts can arise from the addition of an acid to a compound of the disclosure. In some embodiments, the acid is organic. In some embodiments, the acid is inorganic. In some embodiments, the acid is hydrochloric acid, hydrobromic acid, hydroiodic acid, nitric acid, nitrous acid, sulfuric acid, sulfurous acid, a phosphoric acid, isonicotinic acid, lactic acid, salicylic acid, tartaric acid, ascorbic acid, gentisic acid, gluconic acid, glucuronic acid, saccharic acid, formic acid, benzoic acid, glutamic acid, pantothenic acid, acetic acid, propionic acid, butyric acid, fumaric acid, succinic acid, methanesulfonic acid, ethanesulfonic acid, benzenesulfonic acid, p-toluenesulfonic acid, citric acid, oxalic acid, or maleic acid. In some embodiments, the salt is a hydrochloride salt, a hydrobromide salt, a hydroiodide salt, a nitrate salt, a nitrite salt, a sulfate salt, a sulfite salt, a phosphate salt, isonicotinate salt, a lactate salt, a salicylate salt, a tartrate salt, an ascorbate salt, a gentisinate salt, a gluconate salt, a glucuronate salt, a saccharate salt, a formate salt, a benzoate salt, a glutamate salt, a pantothenate salt, an acetate salt, a propionate salt, a butyrate salt, a fumarate salt, a succinate salt, a methanesulfonate (mesylate) salt, an ethanesulfonate salt, a benzenesulfonate salt, a p-toluenesulfonate salt, a citrate salt, an oxalate salt, or a maleate salt.

Pharmaceutical Compositions.

A pharmaceutical composition of the disclosure can be used, for example, before, during, or after treatment of a subject with, for example, another pharmaceutical agent. Subjects can be, for example, elderly adults, adults, adolescents, pre-adolescents, children, toddlers, infants, neonates, and non-human animals. In some embodiments, a subject is a patient. A pharmaceutical composition of the disclosure can be a combination of any pharmaceutical compounds described herein with other chemical components, such as carriers, stabilizers, diluents, dispersing agents, suspending agents, thickening agents, and/or excipients. The pharmaceutical composition facilitates administration of the compound to an organism. Pharmaceutical compositions can be administered in therapeutically-effective amounts as pharmaceutical compositions by various forms and routes including, for example, intravenous, subcutaneous, intramuscular, oral, parenteral, ophthalmic, subcutaneous, transdermal, nasal, vaginal, and topical administration. A pharmaceutical composition can be administered in a local manner, for example, via injection of the compound directly into an organ, optionally in a depot or sustained release formulation or implant. Pharmaceutical compositions can be provided in the form of a rapid release formulation, in the form of an extended release formulation, or in the form of an intermediate release formulation. A rapid release form can provide an immediate release. An extended release formulation can provide a controlled release or a sustained delayed release.

For oral administration, pharmaceutical compositions can be formulated by combining the active compounds with pharmaceutically-acceptable carriers or excipients. Such carriers can be used to formulate liquids, gels, syrups, elixirs, slurries, or suspensions, for oral ingestion by a subject. Non-limiting examples of solvents used in an oral dissolvable formulation can include water, ethanol, isopropanol, saline, physiological saline, DMSO, dimethylformamide, potassium phosphate buffer, phosphate buffer saline (PBS), sodium phosphate buffer, 4-2-hydroxyethyl-1-piperazineethanesulfonic acid buffer (HEPES), 3-(N-morpholino)propanesulfonic acid buffer (MOPS), piperazine-N,N #-bis(2-ethanesulfonic acid) buffer (PIPES), and saline sodium citrate buffer (SSC). Non-limiting examples of co-solvents used in an oral dissolvable formulation can include sucrose, urea, cremaphor, DMSO, and potassium phosphate buffer.

Pharmaceutical preparations can be formulated for intravenous administration. The pharmaceutical compositions can be in a form suitable for parenteral injection as a sterile suspension, solution or emulsion in oily or aqueous vehicles, and can contain formulatory agents such as suspending, stabilizing and/or dispersing agents. Pharmaceutical formulations for parenteral administration include aqueous solutions of the active compounds in water-soluble form. Suspensions of the active compounds can be prepared as oily injection suspensions. Suitable lipophilic solvents or vehicles include fatty oils such as sesame oil, or synthetic fatty acid esters, such as ethyl oleate or triglycerides, or liposomes. The suspension can also contain suitable stabilizers or agents which increase the solubility of the compounds to allow for the preparation of highly concentrated solutions. Alternatively, the active ingredient can be in powder form for constitution with a suitable vehicle, e.g., sterile pyrogen-free water, before use.

The active compounds can be administered topically and can be formulated into a variety of topically administrable compositions, such as solutions, suspensions, lotions, gels, pastes, medicated sticks, balms, creams, and ointments. Such pharmaceutical compositions can contain solubilizers, stabilizers, tonicity enhancing agents, buffers and preservatives.

The compounds of the disclosure can be applied topically to the skin, or a body cavity, for example, oral, vaginal, bladder, cranial, spinal, thoracic, or pelvic cavity of a subject. The compounds of the disclosure can be applied to an accessible body cavity.

The compounds can also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, and PEG. In suppository forms of the compositions, a low-melting wax such as a mixture of fatty acid glycerides, optionally in combination with cocoa butter, can be melted.

In practicing the methods of treatment or use provided herein, therapeutically-effective amounts of the compounds described herein are administered in pharmaceutical compositions to a subject having a disease or condition to be treated. In some embodiments, the subject is a mammal such as a human. A therapeutically-effective amount can vary widely depending on the severity of the disease, the age and relative health of the subject, the potency of the compounds used, and other factors. The compounds can be used singly or in combination with one or more therapeutic agents as components of mixtures.

Pharmaceutical compositions can be formulated using one or more physiologically-acceptable carriers comprising excipients and auxiliaries, which facilitate processing of the active compounds into preparations that can be used pharmaceutically. Formulations can be modified depending upon the route of administration chosen. Pharmaceutical compositions comprising a compound described herein can be manufactured, for example, by mixing, dissolving, emulsifying, encapsulating, entrapping, or compression processes.

The pharmaceutical compositions can include at least one pharmaceutically-acceptable carrier, diluent, or excipient and compounds described herein as free-base or pharmaceutically-acceptable salt form. Pharmaceutical compositions can contain solubilizers, stabilizers, tonicity enhancing agents, buffers and preservatives.

Methods for the preparation of compositions comprising the compounds described herein include formulating the compounds with one or more inert, pharmaceutically-acceptable excipients or carriers to form a solid, semi-solid, or liquid composition. Solid compositions include, for example, powders, tablets, dispersible granules, capsules, and cachets. Liquid compositions include, for example, solutions in which a compound is dissolved, emulsions comprising a compound, or a solution containing liposomes, micelles, or nanoparticles comprising a compound as disclosed herein. Semi-solid compositions include, for example, gels, suspensions and creams. The compositions can be in liquid solutions or suspensions, solid forms suitable for solution or suspension in a liquid prior to use, or as emulsions. These compositions can also contain minor amounts of nontoxic, auxiliary substances, such as wetting or emulsifying agents, pH buffering agents, and other pharmaceutically-acceptable additives.

Non-limiting examples of dosage forms suitable for use in the present disclosure include liquid, powder, gel, nanosuspension, nanoparticle, microgel, aqueous or oily suspensions, emulsion, and any combination thereof. Non-limiting examples of pharmaceutically-acceptable excipients suitable for use in the present disclosure include binding agents, disintegrating agents, anti-adherents, anti-static agents, surfactants, anti-oxidants, coating agents, coloring agents, plasticizers, preservatives, suspending agents, emulsifying agents, anti-microbial agents, spheronization agents, and any combination thereof.

A composition of the disclosure can be, for example, an immediate release form or a controlled release formulation. An immediate release formulation can be formulated to allow the compounds to act rapidly. Non-limiting examples of immediate release formulations include readily dissolvable formulations. A controlled release formulation can be a pharmaceutical formulation that has been adapted such that release rates and release profiles of the active agent can be matched to physiological and chronotherapeutic requirements or, alternatively, has been formulated to effect release of an active agent at a programmed rate. Non-limiting examples of controlled release formulations include granules, delayed release granules, hydrogels (e.g., of synthetic or natural origin), other gelling agents (e.g., gel-forming dietary fibers), matrix-based formulations (e.g., formulations comprising a polymeric material having at least one active ingredient dispersed through), granules within a matrix, polymeric mixtures, and granular masses. In some, a controlled release formulation is a delayed release form. A delayed release form can be formulated to delay a compound's action for an extended period of time. A delayed release form can be formulated to delay the release of an effective dose of one or more compounds, for example, for about 4, about 8, about 12, about 16, or about 24 h. A controlled release formulation can be a sustained release form. A sustained release form can be formulated to sustain, for example, the compound's action over an extended period of time. A sustained release form can be formulated to provide an effective dose of any compound described herein (e.g., provide a physiologically-effective blood profile) over about 4, about 8, about 12, about 16 or about 24 h. Non-limiting examples of pharmaceutically-acceptable excipients can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), each of which is incorporated by reference in its entirety.

Multiple therapeutic agents can be administered in any order or simultaneously. In some embodiments, a compound of the disclosure is administered in combination with, before, or after treatment with another therapeutic agent. If simultaneously, the multiple therapeutic agents can be provided in a single, unified form, or in multiple forms, for example, as multiple separate pills. The agents can be packed together or separately, in a single package or in a plurality of packages. One or all of the therapeutic agents can be given in multiple doses. If not simultaneous, the timing between the multiple doses can vary to as much as about a month. Therapeutic agents described herein can be administered before, during, or after the occurrence of a disease or condition, and the timing of administering the composition containing a therapeutic agent can vary. For example, the compositions can be used as a prophylactic and can be administered continuously to subjects with a propensity to conditions or diseases in order to lessen a likelihood of the occurrence of the disease or condition. The compositions can be administered to a subject during or as soon as possible after the onset of the symptoms. The administration of the therapeutic agents can be initiated within the first 48 h of the onset of the symptoms, within the first 24 h of the onset of the symptoms, within the first 6 h of the onset of the symptoms, or within 3 h of the onset of the symptoms. The initial administration can be via any route practical, such as by any route described herein using any formulation described herein.

A compound can be administered as soon as is practical after the onset of a disease or condition is detected or suspected, and for a length of time necessary for the treatment of the disease, such as, for example, from about 1 month to about 3 months. In some embodiments, the length of time a compound can be administered can be about 1 day, about 2 days, about 3 days, about 4 days, about 5 days, about 6 days, about 1 week, about 2 weeks, about 3 weeks, about 4 weeks, about 1 month, about 5 weeks, about 6 weeks, about 7 weeks, about 8 weeks, about 2 months, about 9 weeks, about 10 weeks, about 11 weeks, about 12 weeks, about 3 months, about 13 weeks, about 14 weeks, about 15 weeks, about 16 weeks, about 4 months, about 17 weeks, about 18 weeks, about 19 weeks, about 20 weeks, about 5 months, about 21 weeks, about 22 weeks, about 23 weeks, about 24 weeks, about 6 months, about 7 months, about 8 months, about 9 months, about 10 months, about 11 months, about 1 year, about 13 months, about 14 months, about 15 months, about 16 months, about 17 months, about 18 months, about 19 months, about 20 months, about 21 months, about 22 months about 23 months, about 2 years, about 2.5 years, about 3 years, about 3.5 years, about 4 years, about 4.5 years, about 5 years, about 6 years, about 7 years, about 8 years, about 9 years, or about 10 years. The length of treatment can vary for each subject.

Pharmaceutical compositions described herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Non-limiting examples are packaged injectables, vials, or ampoules. Aqueous suspension compositions can be packaged in single-dose non-reclosable containers. Multiple-dose reclosable containers can be used, for example, in combination with or without a preservative. Formulations for injection can be presented in unit dosage form, for example, in ampoules, or in multi-dose containers with a preservative. Pharmaceutical compositions provided herein, can be administered in conjunction with other therapies, for example, chemotherapy, radiation, surgery, anti-inflammatory agents, and selected vitamins. The other agents can be administered prior to, after, or concomitantly with the pharmaceutical compositions. Depending on the intended mode of administration, the pharmaceutical compositions can be in the form of solid, semi-solid or liquid dosage forms, such as, for example, tablets, suppositories, pills, capsules, powders, liquids, suspensions, lotions, creams, or gels, for example, in unit dosage form suitable for single administration of a precise dosage. For solid compositions, nontoxic solid carriers include, for example, pharmaceutical grades of mannitol, lactose, starch, magnesium stearate, sodium saccharin, talc, cellulose, glucose, sucrose, and magnesium carbonate. Non-limiting examples of pharmaceutically active agents suitable for combination with compositions of the disclosure include anti-infectives, i.e., aminoglycosides, antiviral agents, antimicrobials, anticholinergics/antispasmotics, antidiabetic agents, antihypertensive agents, antineoplastics, cardiovascular agents, central nervous system agents, coagulation modifiers, hormones, immunologic agents, immunosuppressive agents, and ophthalmic preparations.

Compounds can be delivered via liposomal technology. The use of liposomes as drug carriers can increase the therapeutic index of the compounds. Liposomes are composed of natural phospholipids, and can contain mixed lipid chains with surfactant properties (e.g., egg phosphatidylethanolamine). A liposome design can employ surface ligands for attaching to unhealthy tissue. Non-limiting examples of liposomes include the multilamellar vesicle (MLV), the small unilamellar vesicle (SUV), and the large unilamellar vesicle (LUV). Liposomal physicochemical properties can be modulated to optimize penetration through biological barriers and retention at the site of administration, and to reduce a likelihood of developing premature degradation and toxicity to non-target tissues. Optimal liposomal properties depend on the administration route: large-sized liposomes show good retention upon local injection, small-sized liposomes are better suited to achieve passive targeting. PEGylation reduces the uptake of the liposomes by the liver and spleen, and increases the circulation time, resulting in increased localization at the inflamed site due to the enhanced permeability and retention (EPR) effect. Additionally, liposomal surfaces can be modified to achieve selective delivery of the encapsulated drug to specific target cells. Non-limiting examples of targeting ligands include monoclonal antibodies, vitamins, peptides, and polysaccharides specific for receptors concentrated on the surface of cells associated with the disease.

Non-limiting examples of dosage forms suitable for use in the disclosure include liquid, elixir, nanosuspension, aqueous or oily suspensions, drops, syrups, and any combination thereof. Non-limiting examples of pharmaceutically-acceptable excipients suitable for use in the disclosure include granulating agents, binding agents, lubricating agents, disintegrating agents, sweetening agents, glidants, anti-adherents, anti-static agents, surfactants, anti-oxidants, gums, coating agents, coloring agents, flavoring agents, coating agents, plasticizers, preservatives, suspending agents, emulsifying agents, plant cellulosic material and spheronization agents, and any combination thereof.

Compositions of the disclosure can be packaged as a kit. In some embodiments, a kit includes written instructions on the administration/use of the composition. The written material can be, for example, a label. The written material can suggest conditions methods of administration. The instructions provide the subject and the supervising physician with the best guidance for achieving the optimal clinical outcome from the administration of the therapy. The written material can be a label. In some embodiments, the label can be approved by a regulatory agency, for example the U.S. Food and Drug Administration (FDA), the European Medicines Agency (EMA), or other regulatory agencies.

Dosing.

Pharmaceutical compositions described herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Non-limiting examples are liquids in vials or ampoules. Aqueous suspension compositions can be packaged in single-dose non-reclosable containers. Multiple-dose reclosable containers can be used, for example, in combination with a preservative. Formulations for parenteral injection can be presented in unit dosage form, for example, in ampoules, or in multi-dose containers with a preservative.

A dose can be expressed in terms of an amount of the drug divided by the mass of the subject, for example, milligrams of drug per kilograms of subject body mass. A compound described herein can be present in a composition in a range of from about 1 mg to about 2000 mg; from about 100 mg to about 2000 mg; from about 10 mg to about 2000 mg; from about 5 mg to about 1000 mg, from about 10 mg to about 500 mg, from about 50 mg to about 250 mg, from about 100 mg to about 200 mg, from about 1 mg to about 50 mg, from about 50 mg to about 100 mg, from about 100 mg to about 150 mg, from about 150 mg to about 200 mg, from about 200 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 550 mg, from about 550 mg to about 600 mg, from about 600 mg to about 650 mg, from about 650 mg to about 700 mg, from about 700 mg to about 750 mg, from about 750 mg to about 800 mg, from about 800 mg to about 850 mg, from about 850 mg to about 900 mg, from about 900 mg to about 950 mg, or from about 950 mg to about 1000 mg.

In some embodiments, a compound is administered in an amount ranging from about 5 mg/kg to about 50 mg/kg, 250 mg/kg to about 2000 mg/kg, about 10 mg/kg to about 800 mg/kg, about 50 mg/kg to about 400 mg/kg, about 100 mg/kg to about 300 mg/kg, or about 150 mg/kg to about 200 mg/kg. In some embodiments, a compound described herein can be present in a composition in a range of from about 20 mg/kg to about 400 mg/kg. In some embodiments, a compound described herein can be present in a composition in a range of from about 20 mg/kg to about 240 mg/kg. In some embodiments, a compound described herein can be present in a composition in a range of from about 75 mg/kg to about 150 mg/kg. In some embodiments, a compound described herein can be present in a composition in a range of from about 75 mg/kg to about 150 mg/kg. In some embodiments, a compound described herein can be present in a composition in a range of from about 100 mg/kg to about 150 mg/kg.

In some embodiments, a compound described herein can be present in a composition in an amount of about 75 mg/kg. In some embodiments, a compound described herein can be present in a composition in an amount of about 100 mg/kg. In some embodiments, a compound described herein can be present in a composition in an amount of about 150 mg/kg. In some embodiments, a compound described herein can be present in a composition in an amount of about 200 mg/kg. In some embodiments, a compound described herein can be present in a composition in an amount of about 250 mg/kg. In some embodiments, a compound described herein can be present in a composition in an amount of about 400 mg/kg.

A compound described herein can be present in a composition in an amount of about 1 mg, about 2 mg, about 3 mg, about 4 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg, about 2050 mg, about 2100 mg, about 2150 mg, about 2200 mg, about 2250 mg, about 2300 mg, about 2350 mg, about 2400 mg, about 2450 mg, about 2500 mg, about 2550 mg, about 2600 mg, about 2650 mg, about 2700 mg, about 2750 mg, about 2800 mg, about 2850 mg, about 2900 mg, about 2950 mg, or about 3000 mg.

In some embodiments, a compound described herein can be present in a composition in an amount of about 100 mg, about 120 mg, about 140 mg, about 160 mg, about 180 mg, about 200 mg, about 220 mg, about 240 mg, about 260 mg, about 280 mg, or about 300 mg. In some embodiments, a compound described herein can be present in a composition in an amount of about 150 mg. In some embodiments, a compound described herein can be present in a composition in an amount of about 170 mg. In some embodiments, a compound described herein can be present in a composition in an amount of about 280 mg. In some embodiments, a compound described herein can be present in a composition in an amount of about 300 mg.

Pharmacodynamic and Pharmacokinetic Parameters.

Pharmacokinetic and pharmacodynamic data can be obtained by various experimental techniques. Appropriate pharmacokinetic and pharmacodynamic profile components describing a particular composition can vary due to variations in the metabolism of compound of the disclosure in different subjects. Pharmacokinetic and pharmacodynamic profiles can be based on the determination of the mean parameters of a group of subjects. The group of subjects includes any reasonable number of subjects suitable for determining a representative mean, for example, 5 subjects, 10 subjects, 15 subjects, 20 subjects, 25 subjects, 30 subjects, 35 subjects, or more. The mean is determined by calculating the average of all subject's measurements for each parameter measured.

A dose can be modulated to achieve a desired pharmacokinetic or pharmacodynamics profile, such as a desired or effective blood profile, as described herein. $SC_{150}$ is a measure of the effectiveness of a substance in activating DNA binding by a protein target. This quantitative measure indicates the concentration of the compound required to increase the DNA binding activity by 50% relative to DNA binding activity in the absence of the compound.

The outcome of treating a human subject with a therapy can be measured by calculating pharmacodynamic and pharmacokinetic parameters. Non-limiting examples of pharmacodynamic and pharmacokinetic parameters that can be used to determine the effect of treatment of a subject with a therapy of the disclosure include: a) the amount of drug administered, which can be represented as a dose D; b) the dosing interval, which can be represented as $\tau$; c) the apparent volume in which a drug is distributed, which can be represented as a volume of distribution $V_d$, where $V_d$ D $C_0$; d) the amount of drug in a given volume of tissue, which can be represented as concentration $C_0$ or $C_{ss}$, where $C_0$ or $C_{ss}$=D/Vd; e) the half-life of a drug $t_{1/2}$, where $t_{1/2}=\ln(2)\ k_e$; f) the rate at which a drug is removed from the body $k_e$, where $k_e\ \ln(2)\ t_{1/2}$=CL $V_d$; g) the rate of infusion required to balance the equation $K_{in}$, where $K_{in}=C_{ss}\cdot CL$; h) the integral of the concentration-time curve after administration of a single dose, which can be represented as $AUC_{0-\infty}$, wherein $\int_0^\infty C\ dt$, or in steady-state, which can be represented as $AUC\tau_{,ss}$, wherein $\int_t^{t+\tau} C\ dt$; i) the volume of tissue cleared of the drug per unit time, which can be represented as CL (clearance), wherein $CL=V_d\cdot k_e$=D/AUC; j) the systemically available fraction of a drug, which can be represented as f, where $$f = \frac{AUCpo.Div}{AUCiv.Dpo};$$

k) the peak tissue concentration of a drug after administration $C_{max}$; l) the time taken by a drug to reach $C_{max}$, $t_{max}$; m) the lowest concentration that a drug reaches before the next dose is administered $C_{min}$; and n) the peak trough fluctuation within one dosing interval at steady state, which can be represented as % PTF=100.

$$\frac{(Cmax, ss - Cmin, ss)}{Cav, ss}$$

where $$C_{av,ss} = \frac{AUC\tau, ss}{\tau}.$$

The pharmacokinetics parameters can be any parameters suitable for describing the tissue concentration profiles of a therapy of the disclosure. For example, the pharmacokinetics profile can be obtained at a time after dosing of, for example, about zero minutes, about 1 minute, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 16 minutes, about 17 minutes, about 18 minutes, about 19 minutes, about 20 minutes, about 21 minutes, about 22 minutes, about 23 minutes, about 24 minutes, about 25 minutes, about 26 minutes, about 27 minutes, about 28 minutes, about 29 minutes, about 30 minutes, about 31 minutes, about 32 minutes, about 33 minutes, about 34 minutes, about 35 minutes, about 36 minutes, about 37 minutes, about 38 minutes, about 39 minutes, about 40 minutes, about 41 minutes, about 42 minutes, about 43 minutes, about 44 minutes, about 45 minutes, about 46 minutes, about 47 minutes, about 48 minutes, about 49 minutes, about 50 minutes, about 51 minutes, about 52 minutes, about 53 minutes, about 54 minutes, about 55 minutes, about 56 minutes, about 57 minutes, about 58 minutes, about 59 minutes, about 60 minutes, about zero hours, about 0.5 hours, about 1 hour, about 1.5 hours, about 2 hours, about 2.5 hours, about 3 hours, about 3.5 hours, about 4 hours, about 4.5 hours, about 5 hours, about 5.5 hours, about 6 hours, about 6.5 hours, about 7 hours, about 7.5 hours, about 8 hours, about 8.5 hours, about 9 hours, about 9.5 hours, about 10 hours, about 10.5 hours, about 11 hours, about 11.5 hours, about 12 hours, about 12.5 hours, about 13 hours, about 13.5 hours, about 14 hours, about 14.5 hours, about 15 hours, about 15.5 hours, about 16 hours, about 16.5 hours, about 17 hours, about 17.5 hours, about 18 hours, about 18.5 hours, about 19 hours, about 19.5 hours, about 20 hours, about 20.5 hours, about 21 hours, about 21.5 hours, about 22 hours, about 22.5 hours, about 23 hours, about 23.5 hours, or about 24 hours.

The pharmacokinetic parameters can be any parameters suitable for describing a small molecule that binds to a non-wild type p53 protein and reconforms the non-wild type p53 protein to a conformation of p53 that exhibits anti-cancer activity. The $C_{max}$ can be, for example, not less than about 1 ng/mL; not less than about 2 ng/mL; not less than about 3 ng/mL; not less than about 4 ng/mL; not less than about 5 ng/mL; not less than about 6 ng/mL; not less than about 7 ng/mL; not less than about 8 ng/mL; not less than about 9 ng/mL; not less than about 10 ng/mL; not less than about 15 ng/mL; not less than about 20 ng/mL; not less than about 25 ng/mL; not less than about 50 ng/mL; not less than about 75 ng/mL; not less than about 100 ng/mL; not less than about 200 ng/mL; not than about 500 ng/mL; not than about 1,000 ng/mL; not than about 2,000 ng/mL; not less than about 3,000 ng/mL; not less than about 4,000 ng/mL; not less than about 5,000 ng/mL; not less than about 6,000 ng/mL; not less than about 7,000 ng/mL; not less than about 8,000 ng/mL; not less than about 9,000 ng/mL; not less than about 10,000 ng/mL; not less than about 12,500 ng/mL; not less than about 15,000 ng/mL; not less than about 17,500 ng/mL; not less than about 20,000 ng/mL; or any other $C_{max}$ appropriate for describing a pharmacokinetic profile of a compound described herein. The $C_{max}$ can be, for example, about 1 ng/mL to about 50,000 ng/mL; about 1 ng/mL to about 45,000 ng/mL; about 1 ng/mL to about 40,000 ng/mL; about 1 ng/mL to about 35,000 ng/mL; about 1 ng/mL to about 30,000 ng/mL; about 1 ng/mL to about 25,000 ng/mL; about 1 ng/mL to about 20,000 ng/mL; about 1 ng/mL to about 15,000 ng/mL; about 1 ng/mL to about 10,000 ng/mL; about 5,000 ng/mL to about 50,000 ng/mL; about 5,000 ng/mL to about 45,000 ng/mL; about 5,000 ng/mL to about 40,000 ng/mL; about 5,000 ng/mL to about 35,000 ng/mL; about 5,000 ng/mL to about 30,000 ng/mL; about 5,000 ng/mL to about 25,000 ng/mL; about 5,000 ng/mL to about 20,000 ng/mL; about 5,000 ng/mL to about 15,000 ng/mL; about 5,000 ng/mL to about 10,000 ng/mL; about 7,500 ng/mL to about 50,000 ng/mL; about 7,500 ng/mL to about 45,000 ng/mL; about 7,500 ng/mL to about 4,000 ng/mL; about 7,500 ng/mL to about 35,000 ng/mL; about 7,500 ng/mL to about 30,000 ng/mL; about 7,500 ng/mL to about 25,000 ng/mL; about 7,500 ng/mL to about 20,000 ng/mL; about 7,500 ng/mL to about 15,000 ng/mL; about 7,500 ng/mL to about 10,000 ng/mL; about 10,000 ng/mL to about 50,000 ng/mL; about 10,000 ng/mL to about 45,000 ng/mL; about 10,000 ng/mL to about 40,000 ng/mL; about 10,000 ng/mL to about 35,000 ng/mL; about 10,000 ng/mL to about 30,000 ng/mL; about 10,000 ng/mL to about 25,000 ng/mL; about 10,000 ng/mL to about 20,000 ng/mL; or about 10,000 ng/mL to about 15,000 ng/mL.

The $T_{max}$ of a compound described herein can be, for example, not greater than about 0.5 hours, not greater than about 1 hours, not greater than about 1.5 hours, not greater than about 2 hours, not greater than about 2.5 hours, not greater than about 3 hours, not greater than about 3.5 hours, not greater than about 4 hours, not greater than about 4.5 hours, not greater than about 5 hours, or any other $T_{max}$ appropriate for describing a pharmacokinetic profile of a compound described herein. The $T_{max}$ can be, for example, about 0.1 hours to about 24 hours; about 0.1 hours to about 0.5 hours; about 0.5 hours to about 1 hour; about 1 hour to about 1.5 hours; about 1.5 hours to about 2 hour; about 2 hours to about 2.5 hours; about 2.5 hours to about 3 hours; about 3 hours to about 3.5 hours; about 3.5 hours to about 4 hours; about 4 hours to about 4.5 hours; about 4.5 hours to about 5 hours; about 5 hours to about 5.5 hours; about 5.5 hours to about 6 hours; about 6 hours to about 6.5 hours; about 6.5 hours to about 7 hours; about 7 hours to about 7.5 hours; about 7.5 hours to about 8 hours; about 8 hours to about 8.5 hours; about 8.5 hours to about 9 hours; about 9 hours to about 9.5 hours; about 9.5 hours to about 10 hours; about 10 hours to about 10.5 hours; about 10.5 hours to about 11 hours; about 11 hours to about 11.5 hours; about 11.5 hours to about 12 hours; about 12 hours to about 12.5 hours; about 12.5 hours to about 13 hours; about 13 hours to about 13.5 hours; about 13.5 hours to about 14 hours; about 14 hours to about 14.5 hours; about 14.5 hours to about 15 hours; about 15 hours to about 15.5 hours; about 15.5 hours to about 16 hours; about 16 hours to about 16.5 hours; about 16.5 hours to about 17 hours; about 17 hours to about 17.5 hours; about 17.5 hours to about 18 hours; about 18 hours to about 18.5 hours; about 18.5 hours to about 19 hours; about 19 hours to about 19.5 hours; about 19.5 hours to about 20 hours; about 20 hours to about 20.5 hours; about 20.5 hours to about 21 hours; about 21 hours to about 21.5 hours; about 21.5 hours to about 22 hours; about 22 hours to about 22.5 hours; about 22.5 hours to about 23 hours; about 23 hours to about 23.5 hours; or about 23.5 hours to about 24 hours.

The $AUC_{(0\text{-}inf)}$ or $AUC_{(last)}$ of a compound described herein can be, for example, not less than about 50,000 ng·hr/mL, not less than about 55,000 ng·hr/mL, not less than about 60,000 ng·hr/mL, not less than about 65,000 ng·hr/mL, not less than about 70,000 ng·hr/mL, not less than about 75,000 ng·hr/mL, not less than about 80,000 ng·hr/mL, not less than about 85,000 ng·hr/mL, not less than about 90,000 ng·hr/mL, not less than about 95,000 ng·hr/mL, not less than about 100,000 ng·hr/mL, not less than about 105,000 ng·hr/mL, not less than about 110,000 ng·hr/mL, not less than about 115,000 ng·hr/mL, not less than about 120,000 ng·hr/mL, not less than about 125,000 ng·hr/mL, not less than about 130,000 ng·hr/mL, not less than about 135,000 ng·hr/mL, not less than about 140,000 ng·hr/mL, not less than about 145,000 ng·hr/mL, not less than about 150,000 ng·hr/mL, not less than about 155,000 ng·hr/mL, not less than about 160,000 ng·hr/mL, not less than about 165,000 ng·hr/mL, not less than about 170,000 ng·hr/mL, not less than about 175,000 ng·hr/mL, not less than about 180,000 ng·hr/mL, not less than about 185,000 ng·hr/mL, not less than about 190,000 ng·hr/mL, not less than about 195,000 ng·hr/mL, not less than about 200,000 ng·hr/mL, or any other $AUC_{(0\text{-}inf)}$ appropriate for describing a pharmacokinetic profile of a compound described herein. The $AUC_{(0\text{-}inf)}$ of a compound described herein can be, for example, about 1,000 ng·hr/mL to about 100,000 ng·hr/mL; about 40,000 ng·hr/mL to about 50,000 ng·hr/mL; about 50,000 ng·hr/mL to about 60,000 ng·hr/mL; about 60,000 ng·hr/mL to about 70,000 ng·hr/mL; about 70,000 ng·hr/mL to about 80,000 ng·hr/mL; about 80,000 ng·hr/mL to about 90,000 ng·hr/mL; about 90,000 ng·hr/mL to about 100,000 ng·hr/mL; about 100,000 ng·hr/mL to about 125,000 ng·hr/mL; about 125,000 ng·hr/mL to about 150,000 ng·hr/mL; about 150,000 ng·hr/mL to about 175,000 ng·hr/mL; about 175,000 ng·hr/mL to about 200,000 ng·hr/mL; about 50,000 ng·hr/mL to about 70,000 ng·hr/mL; about 50,000 ng·hr/mL to about 60,000 ng·hr/mL; about 50,000 ng·hr/mL to about 80,000 ng·hr/mL; about 50,000 ng·hr/mL to about 100,000 ng·hr/mL; about 50,000 ng·hr/mL to about 110,000 ng·hr/mL; about 50,000 ng·hr/mL to about 120,000 ng·hr/mL; about 50,000 ng·hr/mL to about 130,000 ng·hr/mL; about 50,000 ng·hr/mL to about 140,000 ng·hr/mL; about 50,000 ng·hr/mL to about 150,000 ng·hr/mL; about 60,000 ng·hr/mL to about 110,000 ng·hr/mL; about 60,000 ng·hr/mL to about 120,000 ng·hr/mL; about 60,000 ng·hr/mL to about 130,000 ng·hr/mL; about 60,000 ng·hr/mL to about 140,000 ng·hr/mL; about 60,000 ng·hr/mL to about 150,000 ng·hr/mL, about 100,000 ng·hr/mL to about 110,000 ng·hr/mL; about 100,000 ng·hr/mL to about 120,000 ng·hr/mL; about 100,000 ng·hr/mL to about 130,000 ng·hr/mL; about 100,000 ng·hr/mL to about 140,000 ng·hr/mL; or about 100,000 ng·hr/mL to about 150,000 ng·hr/mL.

EXAMPLES

Synthesis of alkynyl reagents. Reagents used in these examples can be prepared via methods described in U.S. Patent Publications US20220315564A1 and US20170240525A1, each of which is incorporated by reference in its entirety.

Generic Synthetic Methods

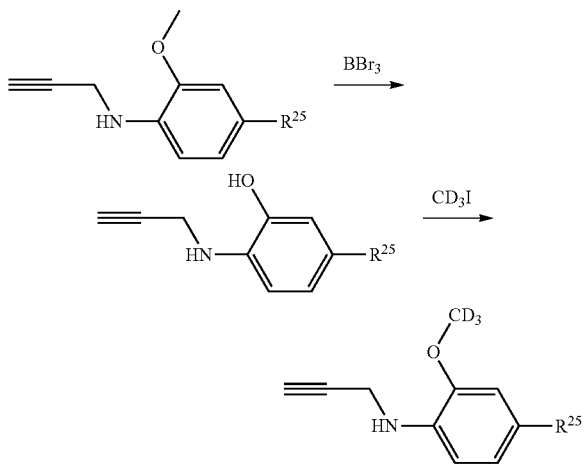

Propynes with deuterated methoxy groups were prepared by treating the corresponding phenols with deuterated methyl iodide.

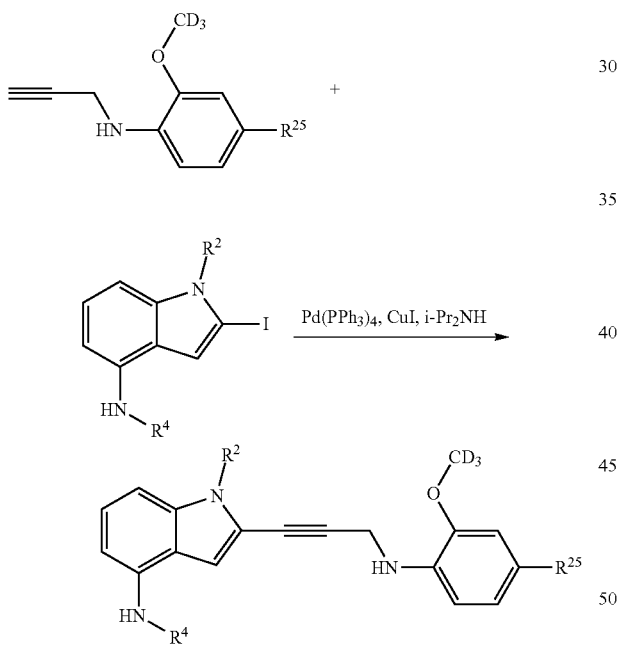

Coupling of a propyne with an indole iodide, such as in the presence of Pd(PPh$_3$)$_4$ and CuI and diisopropylamine provided the compounds of the disclosure.

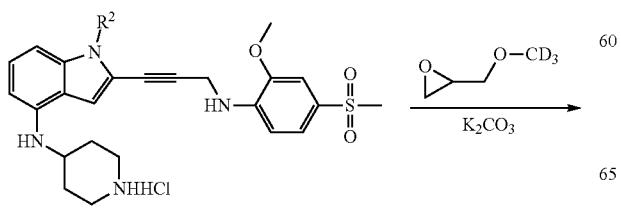

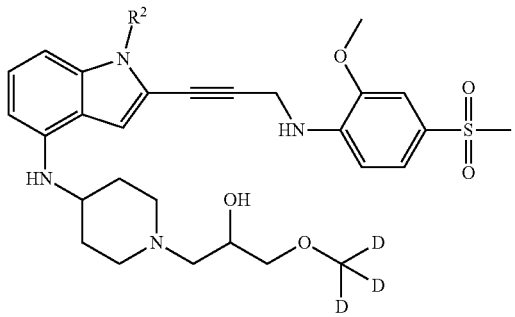

Modification of the piperidine group was achieved by treating compounds with deuterated oxirane, which yielded the deuterated methoxy alcohol.

The following examples contain detailed descriptions of the methods of preparation of compounds of Formulas I-II. These detailed descriptions fall within the scope, and serve to exemplify, the above described General Synthetic Procedures which form part of the disclosure.

These detailed descriptions are presented for illustrative purposes only and are not intended as a restriction on the scope of the disclosure. All parts are by weight and temperatures are in Degrees centigrade unless otherwise indicated.

Example 1: Synthesis of Compound 1 and Compound 2

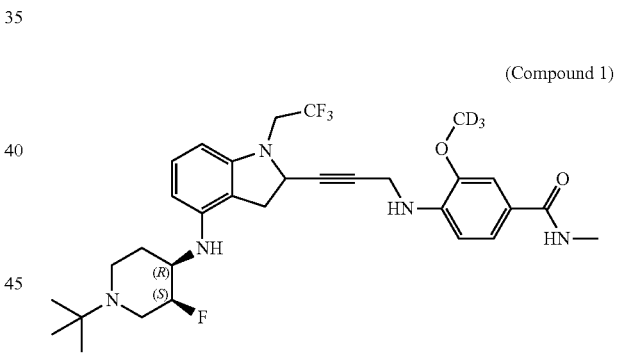

(Compound 1)

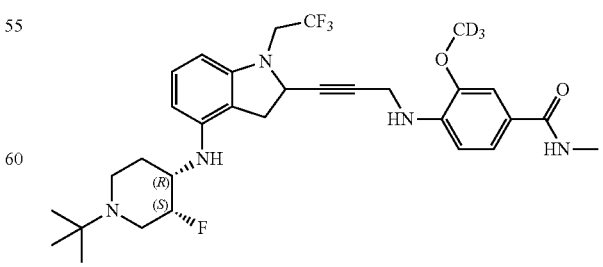

(Compound 2)

The compounds were prepared via the following synthetic scheme:
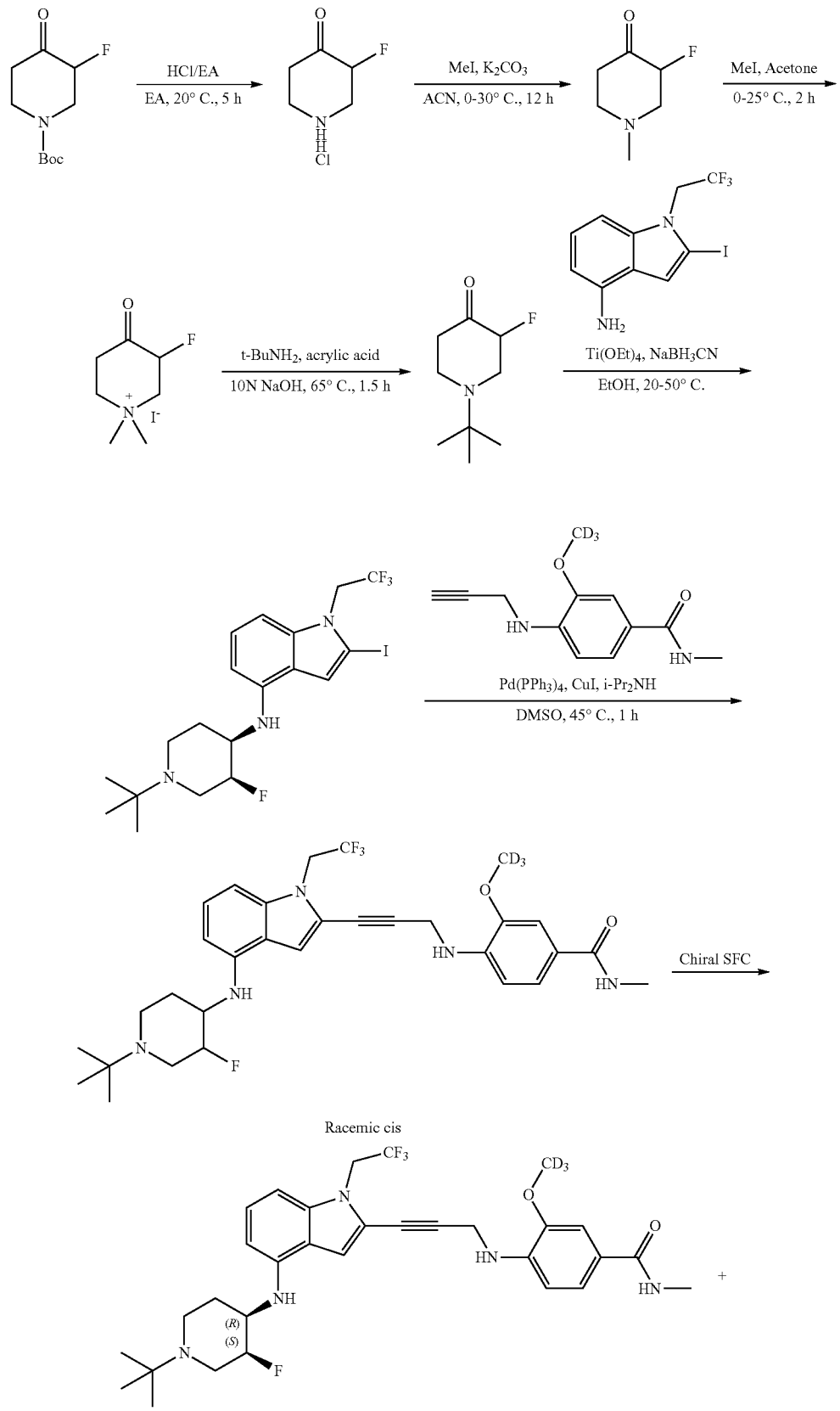

-continued

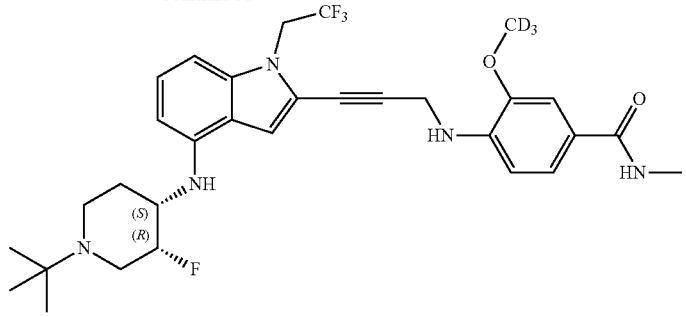

Step 1-3-fluoropiperidin-4-one hydrochloride: Tert-butyl 3-fluoro-4-oxo-piperidine-1-carboxylate (200 g, 920.7 mmol, 1 eq) was added to HCl/EtOAc (4N, 1500 mL) and the mixture was stirred at 20° C. for 5 hr. The mixture was filtered, the filter cake was collected to afford crude 3-fluoropiperidin-4-one as a light-yellow solid. (805 g, HCl salt).

Step 2-3-fluoro-1-methylpiperidin-4-one: To a mixture of crude 3-fluoropiperidin-4-one HCl (Step 1, 100 g, 651.1 mmol, 1 eq) and $K_2CO_3$ (270.0 g, 1.95 mol, 3 eq) in acetonitrile (1000 mL) was added methyl iodide (92.4 g, 651.1 mmol, 40.5 mL, 1 eq) at 0° C. The mixture was stirred at 30° C. for 12 hr. The mixture was diluted with 2000 mL of DCM and filtered. The filtrate was concentrated to afford crude 3-fluoro-1-methyl-piperidin-4-one as a yellow oil. The reaction was repeated five times to yield 600 g of the desired compound. $^1$H NMR: (400 MHz, DMSO-d6) δ=5.29-5.06 (m, 1H), 3.37-3.31 (m, 1H), 3.02-2.91 (m, 1H), 2.69-2.61 (m, 1H), 2.36-2.32 (m, 3H), 2.31-2.27 (m, 1H), 2.24-2.17 (m, 2H).

Step 3-3-fluoro-1,1-dimethyl-4-oxopiperidin-1-ium: To a solution of 3-fluoro-1-methyl-piperidin-4-one (Step 2, 147.0 g, 1.12 mol, 1 eq) in acetone (1100 mL) was added methyl iodide (159.1 g, 1.1 mol, 69.8 mL, 1 eq) at 0° C., and the mixture was stirred at 25° C. for 2 hr. The mixture was concentrated to afford crude 3-fluoro-1,1-dimethyl-piperidin-1-ium-4-one as a yellow solid. The reaction was repeated four times to yield a total of 1.25 kg of the desired compound.

Step 4-1-(tert-butyl)-3-fluoropiperidin-4-one: To a solution of acrylic acid (10 batches, 164.9 g, 2.29 mol, 157.07 mL, 5 eq) in $H_2O$ (460 mL) was added NaOH (10N, 217.4 mL, 4.75 eq) slowly, and then 3-fluoro-1,1-dimethyl-piperidin-1-ium-4-one (Step 3, 125 g, 457.7 mmol, 1 eq, I—) and tert-butylamine (669.5 g, 9.15 mol, 962.0 mL, 20 eq) were added. The mixture was warmed to 65° C. and stirred for 1.5 hr. The mixture was concentrated to remove excess tert-butylamine, and then extracted with DCM (3×100 mL). The organic layers were washed with brine (50 mL), dried over $Na_2SO_4$, filtered and concentrated. The residue was purified by column chromatography ($SiO_2$, DCM/EA=5/1) to afford 1-tert-butyl-3-fluoro-piperidin-4-one as a brown oil (total 440 g). $^1$H NMR: (400 MHz, DMSO-d6) δ=5.14-4.97 (m, 1H), 3.60-3.53 (m, 1H), 3.23-3.17 (m, 1H), 2.55-2.52 (m, 1H), 2.34-2.28 (m, 3H), 1.08 (s, 7H).

Step 5-rac-N-((3S,4R)-1-(tert-butyl)-3-fluoropiperidin-4-yl)-2-iodo-1-(2,2,2-trifluoroethyl)-1H-indol-4-amine: To a solution of 2-iodo-1-(2,2,2-trifluoroethyl)indol-4-ylamine (38 g, 100.9 mmol, 1 eq, HCl) and 1-tert-butyl-3-fluoro-piperidin-4-one (Step 4, 43.7 g, 252.3 mmol, 2.5 eq) in EtOH (760 mL) was added Ti(OEt)$_4$ (230.2 g, 1.01 mol, 209.3 mL, 10 eq) in one portion at 20° C. under $N_2$. The mixture was stirred at 50° C. for 16 hr. NaBH$_3$CN (126.8 g, 2.0 mol, 20 eq) was added at 50° C. and stirred for 2 hours under $N_2$. The mixture was added to EtOAc (4000 mL) and water (800 mL), then sat. NaHCO$_3$ was added to adjust the mixture to pH=9. The mixture was filtered through silica gel and extracted with EtOAc (2×1500 mL). The organic layers were washed with brine (1000 mL), dried over $Na_2SO_4$, filtered and concentrated to give the residue. The residue was purified by column chromatography ($SiO_2$, Petroleum ether/EtOAc/DCM=0/1/0 to 10/1/1) afford a crude material. The crude material was triturated with 150 mL of MTBE/PE=5/1 for 2 h and filtered. 24.5 g with 62% purity (cis): S1 was obtained. The filtrate was concentrated to afford ~70 g with 18% purity: L1. The 24.5 g crude S1 was purified by prep-HPLC (FA condition: column: Phenomenex luna C$_{18}$ (250*70 mm, 15 um); mobile phase: [water(FA)-ACN]; B %: 20%-50%, 20 min). The 70 g crude L1 was purified by prep-HPLC (FA condition: column: Phenomenex luna C$_{18}$ 250 mm*100 mm*10 mm; mobile phase: [water(FA)-ACN]; B %: 20%-50%, 25 min) to afford rac-N-((3S,4R)-1-(tert-butyl)-3-fluoropiperidin-4-yl)-2-iodo-1-(2,2,2-trifluoroethyl)-1H-indol-4-amine as a yellow solid (12.8 g, 24.3 mmol, 4.81% yield). LC-MS (ES+, m/z): 498.2 [(M+H)+].
$^1$H NMR: (400 MHz, DMSO-d$_6$) δ=7.25 (s, 2H), 6.94-6.88 (m, 1H), 6.86-6.79 (m, 1H), 6.24 (d, J=7.7 Hz, 2H), 5.34 (d, J=8.7 Hz, 2H), 5.08-4.94 (m, 4H), 4.90-4.73 (m, 1H), 3.67-3.47 (m, 1H), 3.29-3.17 (m, 2H), 3.01 (br d, J=9.3 Hz, 1H), 2.45-2.29 (m, 1H), 2.21 (br t, J=10.4 Hz, 2H), 1.91-1.77 (m, 2H), 1.77-1.69 (m, 2H), 1.04 (s, 9H).

Step 6-3-hydroxy-N-methyl-4-(prop-2-yn-1-ylamino) benzamide: BBr$_3$ (9.2 g, 36.7 mmol, 3.5 mL, 4 eq) was added slowly to a solution of 3-methoxy-N-methyl-4-(prop-2-ynylamino)benzamide (2.0 g, 9.2 mmol, 1 eq) in DCM (50 mL) at 0° C. under $N_2$. The mixture was stirred at 25° C. for 2 hr. The reaction was quenched with water (50 mL) slowly. The mixture was filtered, and the filter cake was discarded. The filtrate was extracted with DCM/THF=10/1 (3×50 mL). The organic layers were washed with brine (30 mL), dried over Na$_2$SO$_4$, filtered and concentrated to give the residue. The residue was purified by prep-HPLC (neutral condition: column: Welch Xtimate C$_{18}$ 250*70 mm*10 mm; mobile phase: [water(NH$_4$HCO$_3$)-ACN]; B %: 5%-30%, 20 min) to afford 3-hydroxy-N-methyl-4-(prop-2-ynylamino)benzamide as a yellow solid (0.65 g, 3.02 mmol, 33% yield, 95% purity) LC-MS (ES+, m/z): 205.2 [(M+H)+].

Step 7-N-methyl-4-(prop-2-ynylamino)-3-(trideuteriomethoxy)benzamide: To a solution of 3-hydroxy-N-methyl-4-(prop-2-ynylamino)benzamide (Step 6, 550.0 mg, 2.7 mmol, 1 eq) in DMF (6 mL) were added $K_2CO_3$ (744.4 mg, 5.4 mmol, 2 eq) and trideuterio(iodo)methane (429.4 mg, 3.0 mmol, 184.3 mL, 1.1 eq), and the mixture was stirred at 25° C. After 2 hr, the mixture was filtered. The filtrate was purified by prep-HPLC (neutral condition: column: Waters Xbridge BEH C18 250*50 mm*10 mm; mobile phase: [water($NH_4HCO_3$)-ACN]; B %: 15%-45%, 10 min) to afford N-methyl-4-(prop-2-ynylamino)-3-(trideuteriomethoxy) benzamide as a yellow solid (260.0 mg, 1.1 mmol, 39.3% yield) LC-MS (ES+, m/z): 222.2 [(M+H)+].

Step 8-4-[3-[4-[[(3S,4R)-1-tert-butyl-3-fluoro-4-piperidyl]amino]-1-(2,2,2-trifluoroethyl)indol-2-yl]prop-2-ynylamino]-N-methyl-3-(trideuteriomethoxy) benzamide: To a solution of N-methyl-4-(prop-2-ynylamino)-3-(trideuteriomethoxy)benzamide (Step 7, 117.4 mg, 477.6 mmol, 90% purity, 1 eq) in DMSO (4 mL) were added i-$Pr_2NH$ (483.3 mg, 4.8 mmol, 674.93 mL, 10 eq), CuI (9.1 mg, 47.8 mmol, 0.1 eq), rac-N-[(3S,4R)-1-tert-butyl-3-fluoro-4-piperidyl]-2-iodo-1-(2,2,2-trifluoroethyl)indol-4-ylamine (Step 5, 0.25 g, 477.6 mmol, 95% purity, 1 eq) and $Pd(PPh_3)_4$ (27.6 mg, 23.9 mmol, 0.05 eq). The mixture was stirred at 45° C. for 1 hr. The mixture was diluted with EtOAc (70 mL) and sat. EDTA solution (80 mL) was added and the mixture was stirred for 1 h. The mixture was extracted with EtOAc (2×80 mL), the organic layers were washed with brine (40 mL), dried over $Na_2SO_4$, filtered and concentrated to give a residue. The residue was purified by prep-HPLC (neutral condition: column: $C_{18}$ (250*50 mm*10 mm); mobile phase: [water ($NH_4HCO_3$)-ACN]; B %: 50%-70%, 10 min) to afford rac-4-[3-[4-[[(3S,4R)-1-tert-butyl-3-fluoro-4-piperidyl]amino]-1-(2,2,2-trifluoroethyl)indol-2-yl]prop-2-ynylamino]-N-methyl-3-(trideuteriomethoxy)benzamide as a yellow solid (0.175 g, 292.49 mmol, 61.25% yield) LC-MS: (ES+, m/z): 591.4 [(M+H)+].

Step 7-4-[3-[4-[[(3S,4R)-1-tert-butyl-3-fluoro-4-piperidyl]amino]-1-(2,2,2-trifluoroethyl)indol-2-yl]prop-2-ynylamino]-N-methyl-3-(trideuteriomethoxy) benzamide (Compound 1) & 4-[3-[4-[[(3R,4S)-1-tert-butyl-3-fluoro-4-piperidyl]amino]-1-(2,2,2-trifluoroethyl)indol-2-yl]prop-2-ynylamino]-N-methyl-3-(trideuteriomethoxy) benzamide (Compound 2): Chiral SFC separation (column: DAICEL CHIRALCEL OJ (250 mm*30 mm, 10 mm); mobile phase: [0.1% $NH_3H_2O$ ETOH]; B %: 43%-43%, 12 min) was used to afford 4-[3-[4-[[(3S,4R)-1-tert-butyl-3-fluoro-4-piperidyl]amino]-1-(2,2,2-trifluoroethyl)indol-2-yl]prop-2-ynylamino]-N-methyl-3-(trideuteriomethoxy) benzamide as a yellow solid (Compound 1) [(78.0 mg, 132.0 mmol, 46.9% yield). LC-MS (ES+, m/z): 591.4 [(M+H)+]. $^1H$ NMR: (400 MHz, DMSO-$d_6$) δ=8.13-8.06 (m, 2H), 7.45-7.39 (m, 2H), 7.34 (d, J=1.7 Hz, 2H), 7.15 (s, 2H), 7.00 (t, J=8.0 Hz, 2H), 6.78-6.70 (m, 4H), 6.23 (d, J=7.8 Hz, 2H), 5.98 (t, J=6.4 Hz, 2H), 5.40 (br d, J=8.7 Hz, 2H), 4.97-4.87 (m, 2H), 4.87-4.71 (m, 1H), 4.31 (d, J=6.2 Hz, 4H), 3.63-3.48 (m, 2H), 3.27-3.17 (m, 2H), 3.01 (br d, J=11.2 Hz, 2H), 2.75 (d, J=4.4 Hz, 3H), 2.43-2.29 (m, 1H), 2.20 (br t, J=11.0 Hz, 2H), 1.89-1.76 (m, 2H), 1.76-1.67 (m, 2H), 1.03 (s, 19H) and 4-[3-[4-[[(3R,4S)-1-tert-butyl-3-fluoro-4-piperidyl]amino]-1-(2,2,2trifluoroethyl) indol-2-yl]prop-2-ynylamino]-N-methyl-3-(trideuteriomethoxy) benzamide (Compound 2) as a yellow solid (80.0 mg, 135.0 mmol, 48.0% yield). LC-MS (ES+, m/z): 591.4 [(M+H)+]. $^1H$ NMR: (400 MHz, DMSO-d6) δ=8.09 (br d, J=4.5 Hz, 2H), 7.44-7.39 (m, 2H), 7.34 (d, J=1.7 Hz, 2H), 7.15 (s, 2H), 7.00 (t, J=8.0 Hz, 2H), 6.78-6.70 (m, 4H), 6.23 (d, J=7.7 Hz, 2H), 5.97 (t, J=6.3 Hz, 2H), 5.40 (br d, J=8.6 Hz, 2H), 4.88 (br s, 2H), 4.87-4.71 (m, 1H), 4.31 (d, J=6.3 Hz, 4H), 3.62-3.47 (m, 2H), 3.21 (br t, J=10.8 Hz, 2H), 3.00 (br d, J=9.4 Hz, 1H), 2.75 (d, J=4.4 Hz, 6H), 2.43-2.30 (m, 1H), 2.20 (br t, J=10.8 Hz, 2H), 1.89-1.76 (m, 2H), 1.76-1.67 (m, 2H), 1.02 (s, 9H).

Example 2: Synthesis of 4-[3-[4-[[(3S,4R)-3-fluoro-1-methyl-4-piperidyl]amino]-1-(2,2,2-trifluoroethyl)indol-2-yl]prop-2-ynylamino]-N-methyl-3-(trideuteriomethoxy)benzamide (Compound 3)

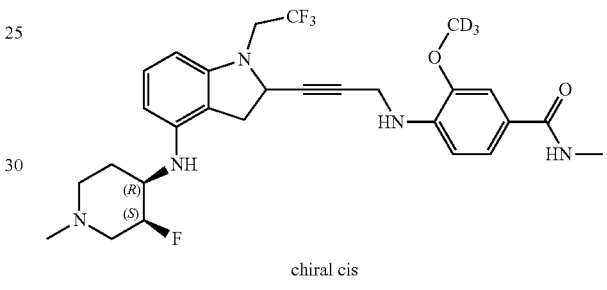

chiral cis

To a solution of N-methyl-4-(prop-2-ynylamino)-3-(trideuteriomethoxy)benzamide (Ex. 1, Step 7, 77.0 mg, 313.0 mmol, 90% purity, 1 eq) in DMSO (1 mL) were added i-$Pr_2NH$ (316.8 mg, 3.13 mmol, 442.39 mL, 10 eq), CuI (6.0 mg, 31.3 mmol, 0.1 eq), N-[(3S,4R)-3-fluoro-1-methyl-4-piperidyl]-2-iodo-1-(2,2,2-trifluoroethyl)indol-4-ylamine (150.0 mg, 313.03 mmol, 95% purity, 1 eq) [prepared by a method similar to that described in Example 1 Step 5] and $Pd(PPh_3)_4$ (18.1 mg, 15.7 mmol, 0.05 eq). The mixture was stirred at 45° C. for 1 hr. The mixture was diluted with EtOAc (40 mL) and sat. EDTA solution (40 mL) was added. The mixture was stirred for 1 h, then extracted with EtOAc (2×40 mL). The organic layers were washed with brine (20 mL), dried over $Na_2SO_4$, filtered and concentrated. The residue was purified by prep-HPLC (neutral condition: column: Waters Xbridge Prep OBD C18 150*40 mm*10 mm; mobile phase: [water($NH_4HCO_3$)-ACN]; B %: 35%-65%, 8 min) to afford 4-[3-[4-[[(3S,4R)-3-fluoro-1-methyl-4-piperidyl]amino]-1-(2,2,2-trifluoroethyl)indol-2-yl]prop-2-ynylamino]-N-methyl-3-(trideuteriomethoxy)benzamide (Compound 3) as a yellow solid (65.0 mg, 117.5 mmol, 37.6% yield) LC-MS: (ES+, m/z): 549.3 [(M+H)+]. $^1H$ NMR: (400 MHz, DMSO-d6) δ=8.14-8.05 (m, 2H), 7.46-7.38 (m, 2H), 7.34 (d, J=1.8 Hz, 2H), 7.17 (s, 2H), 7.00 (t, J=8.0 Hz, 2H), 6.80-6.69 (m, 4H), 6.24 (d, J=7.9 Hz, 2H), 5.98 (t, J=6.3 Hz, 2H), 5.49 (d, J=8.6 Hz, 2H), 4.98-4.88 (m, 2H), 4.87-4.70 (m, 1H), 4.31 (d, J=6.3 Hz, 2H), 3.64-3.45 (m, 1H), 3.09-2.96 (m, 2H), 2.83-2.71 (m, 4H), 2.32-2.15 (m, 4H), 2.12-2.01 (m, 1H), 1.98-1.86 (m, 2H), 1.75-1.59 (m, 1H).

Example 3: Synthesis of rac-N-[(3S,4R)-3-fluoro-1-(trideuteriomethyl)-4-piperidyl]-2-[3-[4-methylsulfon yl-2-(trideuteriomethoxy)anilino]prop-1-ynyl]-1-(2,2,2-trifluoroethyl)indol-4-ylamine (Compound 4)

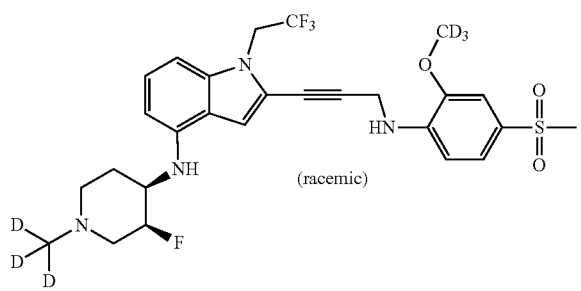 [SMILES: [2H]C([2H])([2H])Oc1cc(S(C)(=O)=O)ccc1NCC#Cc1cc2c(N[C@@H]3CCN(C([2H])([2H])[2H])C[C@@H]3F)cccc2n1CC(F)(F)F]

(racemic)

Step 1-tert-butyl 3-fluoro-4-[[2-iodo-1-(2,2,2-trifluoroethyl)indol-4-yl]amino]piperidine-1-carboxylate: To a solution of 2-iodo-1-(2,2,2-trifluoroethyl)indol-4-ylamine (15 g, 39.70 mmol, 1 eq) and tert-butyl 3-fluoro-4-oxo-piperidine-1-carboxylate (43.12 g, 198.48 mmol, 5 eq) in DCE (150 mL) and AcOH (450 mL) was added sodium triacetoxyborohydride in three equal portions (every half an hour) (12.62 g, 59.54 mmol, 1.5 eq) and the mixture was stirred at 25° C. for 0.5 hr. The mixture was poured into H₂O (1 L) at 0° C., and basified with saturated aqueous Na₂CO₃, pH=8, then extracted with DCM (500 mL×3). The combined organic layers were washed with brine (500 mL), dried over Na₂SO₄, filtered and concentrated under reduced pressure to give tert-butyl 3-fluoro-4-[[2-iodo-1-(2,2,2-trifluoroethyl)indol-4-yl]amino]piperidine-1-carboxylate (30 g, crude).

Step 2-tert-butyl (3S,4R)-3-fluoro-4-[[2-iodo-1-(2,2,2-trifluoroethyl)indol-4-yl]amino]piperidine-1-carboxylate: The residue from step 1 [cis:trans=3.5:1] was purified by prep-HPLC (FA condition; column: Xtimate C₁₈ 10 m 250 mm*80 mm; mobile phase: [water(10 mM NH₄HCO₃)-ACN]; B %: 55%-75%, 22 min) to give the cis form, tert-butyl (3S,4R)-3-fluoro-4-[[2-iodo-1-(2,2,2-trifluoroethyl)indol-4-yl]amino]piperidine-1-carboxylate (11 g, 20.32 mmol, 36.67% yield).

Step 3-N-[(3S,4R)-3-fluoro-4-piperidyl]-2-iodo-1-(2,2,2-trifluoroethyl)indol-4-ylamine: To a solution of tert-butyl (3S,4R)-3-fluoro-4-[[2-iodo-1-(2,2,2-trifluoroethyl)indol-4-yl]amino]piperidine-1-carboxylate (Step 2, 3.5 g, 6.47 mmol, 1 eq) in DCM (6 mL) was added TFA (3 mL). The mixture was stirred at 25° C. for 10 min. The reaction was quenched by addition of Na₂CO₃ aq to adjust to pH=8, and the mixture was extracted with DCM (100 mL×3). The combined organic layers were washed with brine (50 mL×2), dried over [Na₂SO₄], filtered and concentrated under reduced pressure to give a residue (2.3 g, crude) used in the next step directly. LC-MS (ES⁺, m/z): 442.0; [(M+H)⁺] ¹H NMR (400 MHz, DMSO-d₆) δ=7.25-7.28 (s, 1H), 6.88-6.94 (t, 1H), 6.80-6.85 (d, 1H), 6.22-6.27 (d, 1H), 5.37-5.42 (d, 1H), 4.95-5.04 (q, 2H), 4.62-4.79 (d, 1H), 3.60-3.73 (m, 1H), 3.08-3.14 (t, 1H), 2.93-3.00 (d, 1H), 2.69-2.85 (t, 1H), 2.56 (dd, J=38.8 Hz, J=14 Hz 1H), 1.61-1.78 (m, 2H).

Step 4-N-[(3S,4R)-3-fluoro-1-(trideuteriomethyl)-4-piperidyl]-2-iodo-1-(2,2,2-trifluoroethyl)indol-4-ylamine: To a solution of N-[(3S,4R)-3-fluoro-4-piperidyl]-2-iodo-1-(2,2,2-trifluoroethyl)indol-4-ylamine (Step 3, 500.00 mg, 1.13 mmol, 1.0 eq) in DMF (5 mL) were added Cs₂CO₃ (1.11 g, 3.40 mmol, 3 eq) and trideuterio(iodo)methane (160.85 mg, 1.13 mmol, 69.04 μL, 1 eq). The mixture was stirred at 25° C. for 16 hr, then trideuterio(iodo)methane (80.43 mg, 566.63 mmol, 34.52 mL, 0.5 eq) was added. The mixture was stirred at 25° C. for 14 h under N₂ atmosphere. The reaction mixture was quenched by addition H₂O (70 mL) and extracted with EtOAc (50 mL×3). The combined organic layers were washed with brine 20 mL (10 mL×2), dried over Na₂SO₄, filtered and concentrated under reduced pressure to give a residue. The residue was purified by column chromatography (SiO₂, DCM/MeOH=1/0 to 50/1) to give N-[(3S,4R)-3-fluoro-1-(trideuteriomethyl)-4-piperidyl]-2-iodo-1-(2,2,2-trifluoroethyl)indol-4-ylamine (380.00 mg, 646.81 mmol, 57.08% yield, 78.00% purity) LC-MS (ES⁺, n/z): 459.0 [(M+H)⁺].

Step 5-rac-N-[(3S,4R)-3-fluoro-1-(trideuteriomethyl)-4-piperidyl]-2-[3-[4-methylsulfon yl-2-(trideuteriomethoxy)anilino]prop-1-ynyl]-1-(2,2,2-trifluoroethyl)indol-4-ylamine (Compound 4): To a solution of 4-methylsulfonyl-N-prop-2-ynyl-2-(trideuteriomethoxy)aniline [prepared similar to that described in Ex 6, Step 2] (74.24 mg, 306.38 mmol, 1.2 eq) in DMSO (3 mL) were added i-Pr₂NH (258.36 mg, 2.55 mmol, 360.83 mL, 10 eq), N-[(3R,4S)-3-fluoro-1-(trideuteriomethyl)-4-piperidyl]-2-iodo-1-(2,2,2-trifluoroethyl)indol-4-ylamine (Step 4, 150 mg, 255.32 mmol, 1 eq), CuI (9.73 mg, 51.06 mmol, 0.2 eq) and Pd(PPh₃)₄ (14.75 mg, 12.77 mmol, 0.05 eq). The mixture was degassed and purged with N₂ 3 times. The mixture was stirred at 50° C. for 1 hr. The reaction was quenched by addition of EDTA 40 mL, and extracted with EtOAc (30 mL×3). The combined organic layers were washed with brine (10 mL×2), dried over Na₂SO₄, filtered and concentrated under reduced pressure to give a residue. The residue was purified by prep-TLC (SiO₂, DCM: MeOH=10:1) and the residue was repurified by prep-HPLC (FA condition; column: Phenomenex Luna C₁₈ 200*40 mm*10 mm; mobile phase: [water(0.2% FA)-ACN]; B %: 20%-60%, 10 min) to give rac-N-[(3S,4R)-3-fluoro-1-(trideuteriomethyl)-4-piperidyl]-2-[3-[4-methylsulfon yl-2-(trideuteriomethoxy)anilino]prop-1-ynyl]-1-(2,2,2-trifluoroethyl)indol-4-ylamine (Compound 4) (180 mg, 314.33 mmol, 93.26% yield, 100% purity) LC-MS (ES⁺, m/z): 573.1 [(M+H)⁺] ¹H NMR (400 MHz, DMSO-d₆) δ=7.36-7.41 (d, 1H), 7.23-7.26 (s, 1H), 7.16-7.20 (s, 1H), 6.97-7.04 (t, 1H), 6.87-6.91 (d, 1H), 6.71-6.77 (d, 1H), 6.46-6.52 (t, 1H), 6.20-6.27 (d, 1H), 5.46-5.53 (d, 1H), 4.73-4.98 (m, 3H), 4.32-4.39 (d, 2H), 3.58-3.62 (m, 1H), 3.09 (s, 3H), 3.00-3.04 (m, 1H), 2.81 (d, J=10.15 Hz, 1H), 2.17-2.26 (m, 1H), 2.08-2.14 (t, 1H), 1.87-1.96 (m, 1H), 1.67-1.72 (d, 1H).

Example 4: Synthesis of 4-[3-[4-[[(3S,4R)-3-fluoro-1-methyl-4-piperidyl]amino]-1-(2,2,2-trifluoroethyl)indol-2-yl]prop-2-ynylamino]-3-methoxy-N-(trideuteriomethyl)benzamide (Compound 5)

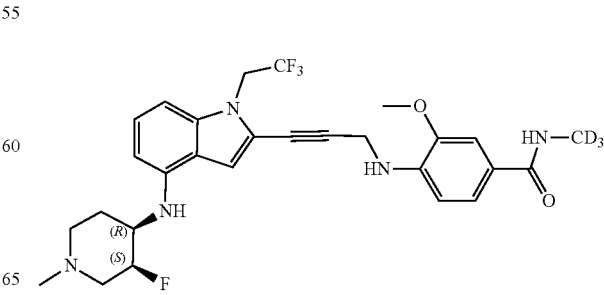

Step 1-t tert-butyl N-[2-methoxy-4-(trideuteriomethylcarbamoyl)phenyl]-N-prop-2-ynyl-carbamate: To a mixture of trideuteriomethanamine hydrochloride (101.65 mg, 1.44 mmol, 1.1 eq) and 4-[tert-butoxycarbonyl(prop-2-ynyl)amino]-3-methoxy-benzoic acid (400 mg, 1.31 mmol, 1.0 eq) in DMF (4 mL) were added HOBt (531.07 mg, 3.93 mmol, 3.0 eq), EDCI (753.43 mg, 3.93 mmol, 3.0 eq), TEA (1.06 g, 10.48 mmol, 1.46 mL, 8.0 eq) in one portion at 25° C. and stirred for 2 hours. The aqueous phase was extracted with EtOAc (3×30 mL) and water (30 mL). The combined organic phase was washed with brine (3×30 mL), dried with anhydrous $Na_2SO_4$, filtered and concentrated in vacuo. The crude material was purified by pre-TLC ($SiO_2$, DCM/MeOH=10:1) to afford the desired compound (360 mg, 1.12 mmol, 85.50% yield) as a white oil. LC-MS ($ES^+$, m/z): 266.2 [(M-55)$^{+*}$].

Step 2-tert-butyl N-[3-[4-[[(3S,4R)-3-fluoro-1-methyl-4-piperidyl]amino]-1-(2,2,2-trifluoroethyl)indol-2-yl]prop-2-ynyl]-N-[2-methoxy-4-(trideuteriomethylcarbamoyl)phenyl]carbamate (1-2): To a mixture of N-[(3S,4R)-3-fluoro-1-methyl-4-piperidyl]-2-iodo-1-(2,2,2-trifluoroethyl)indol-4-ylamine (Ex. 2, 120 mg, 263.60 mmol, 1.0 eq) and tert-butyl N-[2-methoxy-4-(trideuteriomethylcarbamoyl)phenyl]-N-prop-2-ynyl-carbamate (Step 1, 84.72 mg, 263.60 mmol, 1.0 eq) in DMSO (3 mL) were added CuI (5.02 mg, 26.36 mmol, 0.1 eq), N-isopropylpropan-2-amine (266.74 mg, 2640.00 mmol, 10.0 eq), and Pd(PPh$_3$)$_4$ (15.23 mg, 13.18 mmol, 0.1 eq) in one portion at 25° C. under $N_2$ and the reaction was stirred for 1 hr. The mixture was poured into EDTA (sat.) (30 mL) and stirred for 120 min. The aqueous phase was extracted with EtOAc (3×30 mL) and the combined organic phase was washed with brine (3×30 mL), dried with anhydrous $Na_2SO_4$, filtered and concentrated in vacuo. The crude material was purified by pre-TLC ($SiO_2$, DCM/MeOH=10:1) to afford the desired compound (150 mg, 231.23 mmol, 87.72% yield) as a white oil.

Step 3-4-[3-[4-[[(3S,4R)-3-fluoro-1-methyl-4-piperidyl]amino]-1-(2,2,2-trifluoroethyl)indol-2-yl]prop-2-ynylamino]-3-methoxy-N-(trideuteriomethyl)benzamide (Compound 5).

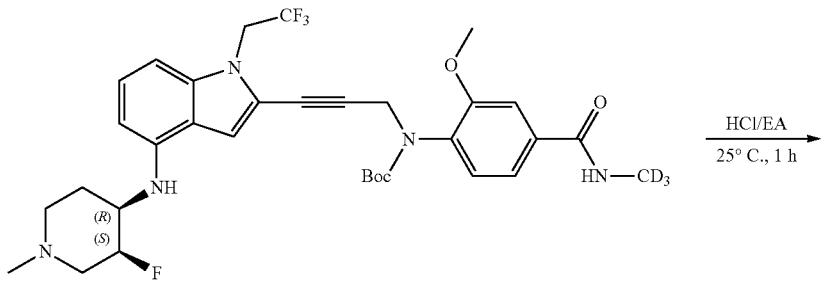

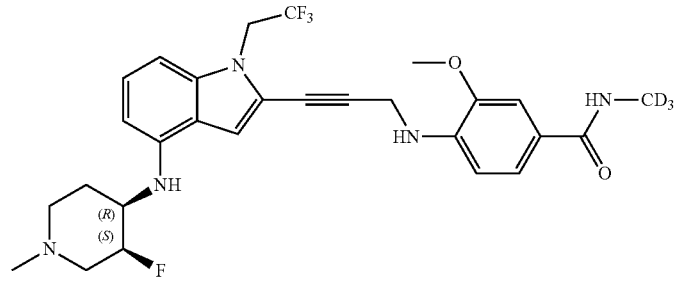

HCl/EtOAc (4 M, 2 mL, 34.6 eq) was added to tert-butyl N-[3-[4-[[(3S,4R)-3-fluoro-1-methyl-4-piperidyl]amino]-1-(2,2,2-trifluoroethyl)indol-2-yl]prop-2-ynyl]-N-[2-methoxy-4-(trideuteriomethylcarbamoyl)phenyl]carbamate (Step 2, 150 mg, 231.23 mmol, 1.0 eq) in one portion at 25° C. and stirred for 1 hr. The mixture was poured into NaHCO$_3$(sat.) (10 mL). The aqueous phase was extracted with EtOAc (3×20 mL). The combined organic phase was washed with brine (3×20 mL), dried with anhydrous Na$_2$SO$_4$, filtered and concentrated in vacuo. The crude material was purified by pre-HPLC, column: Welch Xtimate C$_{18}$ 150*25 mm*5 mm; mobile phase: [water (0.04% HCl)-ACN]; B %: 30%-55%, 10 min] to afford Compound 5 (27.1 mg, 48.55 mmol, 21.00% yield, 98.1% purity) as a yellow solid. LC-MS (ES$^+$, m/z): 549.3 [(M+H)$^+$]. $^1$H NMR (400 MHz, DMSO-d$_6$) δ=8.06 (s, 1H), 7.42 (dd, J=8.19, 1.59 Hz, 1H), 7.35 (d, J=1.71 Hz, 1H), 7.16 (s, 1H), 7.00 (t, J=7.94 Hz, 1H), 6.80-6.65 (m, 2H), 6.24 (d, J=7.70 Hz, 1H), 5.97 (t, J=6.36 Hz, 1H), 5.48 (d, J=8.68 Hz, 1H), 4.99-4.64 (m, 3H), 4.31 (d, J=6.12 Hz, 2H), 3.84 (s, 3H), 3.65-3.45 (m, 1H), 3.02 (t, J=10.33 Hz, 1H), 2.80 (d, J=11.13 Hz, 1H), 2.30-2.15 (m, 4H), 2.09 (t, J=11.08 Hz, 1H), 1.92 (d, J=12.10, 3.78 Hz, 1H), 1.69 (d, J=9.90 Hz, 1H).

Example 5: Synthesis of 4-[3-[4-[[(3S,4R)-3-fluoro-1-methyl-4-piperidyl]amino]-1-(2,2,2-trifluoroethyl)indol-2-yl]prop-2-ynylamino]-3-(trideuteriomethoxy)-N-(trideuteriomethyl)benzamide (Compound 6)

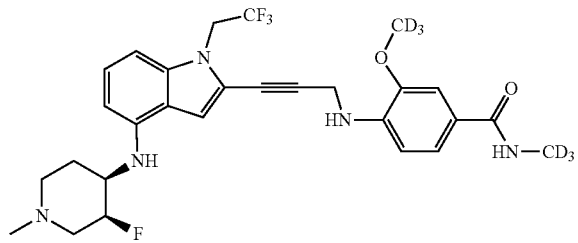 [SMILES: [2H]C([2H])([2H])NC(=O)c1ccc(NCC#Cc2cc3c(N[C@@H]4CCN(C)C[C@@H]4F)cccc3n2CC(F)(F)F)c(OC([2H])([2H])[2H])c1]

Step 1-4-[tert-butoxycarbonyl(prop-2-ynyl)amino]-3-methoxy-benzoic acid: To a mixture of methyl 4-[tert-butoxycarbonyl(prop-2-ynyl)amino]-3-methoxy-benzoate (2 g, 6.26 mmol, 1.0 eq) in MeOH (15 mL) and H$_2$O (5 mL) was added NaOH (751.47 mg, 18.79 mmol, 3.0 eq) in one portion at 20° C. and stirred for 4 hours. HCl (5 M) was added to the solution to adjust to pH=5. The aqueous phase was extracted with EtOAc (3×30 mL). The combined organic phase was washed with brine (3×30 mL), dried with anhydrous Na$_2$SO$_4$, filtered and concentrated in vacuo. The crude material was purified by pre-TLC (SiO$_2$, DCM/MeOH=10:1) to afford the acid (1.8 g, 5.90 mmol, 94.13% yield) as a white solid.

Step 2-tert-butyl N-[2-methoxy-4-(trideuteriomethylcarbamoyl)phenyl]-N-prop-2-ynyl-carbamate: To a mixture of trideuteriomethanamine hydrochloride (457.42 mg, 6.48 mmol, 1.1 eq) and 4-[tert-butoxycarbonyl(prop-2-ynyl)amino]-3-methoxy-benzoic acid (Step 1, 1.8 g, 5.90 mmol, 1.0 eq) in DMF (25 mL) were added HOBt (2.39 g, 17.69 mmol, 3.0 eq), EDCI (3.39 g, 17.69 mmol, 3.0 eq), TEA (4.77 g, 47.16 mmol, 6.56 mL, 8.0 eq) in one portion at 25° C., and the reaction was stirred for 2 hr. The aqueous phase was extracted with EtOAc (3×50 mL) and water (50 mL). The combined organic phase was washed with brine (3×50 mL), dried with anhydrous Na$_2$SO$_4$, filtered and concentrated in vacuo. The residue was purified by silica gel chromatography (column height: 250 mm, diameter: 100 mm, 100-200 mesh silica gel, petroleum ether/EtOAc=80:20 to 70:30) to afford the deuterated amide (1.7 g, 5.29 mmol, 89.72% yield) as a white oil.

Step 3-3-methoxy-4-(prop-2-ynylamino)-N-(trideuteriomethyl)benzamide: To a mixture of tert-butyl N-[2-methoxy-4-(trideuteriomethylcarbamoyl)phenyl]-N-prop-2-ynyl-carbamate (Step 2, 1.85 g, 5.76 mmol, 1.0 eq) in DCM (20 mL) was added TFA (6.16 g, 54.02 mmol, 4 mL, 9.4 eq) in one portion at 25° C. and stirred for 2 hr. The mixture was cooled to 0° C. The residue was poured into NaOH (2 M) to pH=8. The aqueous phase was extracted with EtOAc (3×30 mL). The combined organic phase was washed with brine (3×30 mL), dried with anhydrous Na$_2$SO$_4$, filtered and concentrated in vacuo to afford 3-methoxy-4-(prop-2-ynylamino)-N-(trideuteriomethyl)benzamide (1.1 g, crude) as a yellow solid.

Step 4-3-hydroxy-4-(prop-2-ynylamino)-N-(trideuteriomethyl)benzamide: To a mixture of 3-methoxy-4-(prop-2-ynylamino)-N-(trideuteriomethyl)benzamide (Step 3, 1.1 g, 4.97 mmol, 1.0 eq) in DCM (15 mL) was added BBr$_3$ (1.87 g, 7.46 mmol, 718.51 mL, 1.5 eq) in one portion at 0° C. and stirred for 1 hr. The residue was poured into ice-water (10 mL) and stirred for 20 min. Then the solution was added into NaHCO$_3$(sat.) (10 mL). The aqueous phase was extracted with DCM (3×20 mL) and water (20 mL). The combined water phase was lyophilized. The dried crude was purified by pre-HPLC [column: Phenomen [ex Luna C$_{18}$ 200*40 mm*10 mm; mobile phase: [water(0.2% FA)-ACN]; B %: 1%-50%, 8 min] to afford the hydroxy compound (400 mg, 1.93 mmol, 38.82% yield) as a white solid. LC-MS (ES$^+$, m/z): 208.2 [(M+1)$^+$].

Step 5-4-(prop-2-ynylamino)-3-(trideuteriomethoxy)-N-(trideuteriomethyl)benzamide: To a mixture of 3-hydroxy-4-(prop-2-ynylamino)-N-(trideuteriomethyl)benzamide (Step 4, 350 mg, 1.69 mmol, 1.0 eq) in DMF (6 mL) were added K$_2$CO$_3$ (466.81 mg, 3.38 mmol, 2.0 eq), trideuterio(iodo)methane (293.77 mg, 2.03 mmol, 126.08 mL, 1.2 eq) in one portion at 25° C. and stirred for 1 hr. The aqueous phase was extracted with ethyl acetate (3×20 mL) and water (30 mL). The combined organic phase was washed with brine (3×20 mL), dried with anhydrous Na$_2$SO$_4$, filtered and concentrated in vacuo. The crude material was purified by pre-TLC to afford the deuterated methoxy compound (320 mg, 1.43 mmol, 84.48% yield) as a white oil.

Step 6-4-[3-[4-[[(3S,4R)-3-fluoro-1-methyl-4-piperidyl]amino]-1-(2,2,2-trifluoroethyl)indol-2-yl]prop-2-ynylamino]-3-(trideuteriomethoxy)-N-(trideuteriomethyl)benzamide (Compound 6): To a mixture of N-[(3S,4R)-3-fluoro-1-methyl-4-piperidyl]-2-iodo-1-(2,2,2-trifluoroethyl)indol-4-ylamine (Ex. 2, 250 mg, 549.17 mmol, 1.0 eq) and 4-(prop-2-ynylamino)-3-(trideuteriomethoxy)-N-(trideuteriomethyl)benzamide (Step 5, 184.76 mg, 823.76 mmol, 1.5 eq) in DMSO (5 mL) were added CuI (10.46 mg, 54.92 mmol, 0.1 eq), N-isopropylpropan-2-amine (555.71 mg, 5.49 mmol, 776.13 mL, 10.0 eq), Pd(PPh$_3$)$_4$ (31.73 mg, 27.46 mmol, 0.1 eq) in one portion at 25° C. under N$_2$ and stirred for 3 hr. The residue was poured into EDTA (sat.) (30 mL) and stirred for 120 min. The aqueous phase was extracted with ethyl acetate (3×30 mL). The combined organic phase was washed with brine (3×30 mL), dried with anhydrous Na$_2$SO$_4$, filtered and concentrated in vacuo. The crude material was purified by pre-HPLC [column: Waters Xbridge Prep OBD C$_{18}$ 150*40 mm*10 mm; mobile phase: [water (0.05% NH$_3$H$_2$O+10 mM NH$_4$HCO$_3$)-ACN]; B %:

35%-60%, 8 min] to afford Compound 6 (109.85 mg, 199.15 mmol, 36.26% yield, 100% purity) as a white solid. LC-MS (ES+, m/z): 552.3 [(M+1)+]. ¹H NMR (400 MHz, DMSO-d6) δ=8.07 (s, 1H), 7.41 (d, J=7.28 Hz, 1H), 7.34 (s, 1H), 7.16 (s, 1H), 7.00 (s, 1H), 6.74 (s, 2H), 6.23 (d, J=5.52 Hz, 1H), 5.99 (s, 1H), 5.50 (d, J=7.28 Hz, 1H), 5.02-4.69 (m, 3H), 4.31 (s, 2H), 3.66-3.46 (m, 1H), 3.02 (s, 1H), 2.80 (d, J=8.60 Hz, 1H), 2.26 (d, J=12.35 Hz, 1H), 2.08 (s, 1H), 1.92 (d, J=11.03 Hz, 1H), 1.70 (s, 1H). ¹H NMR (400 MHz, METHANOL-d₄) δ=7.43 (dd, J=8.31, 1.96 Hz, 1H) 7.36 (d, J=1.96 Hz, 1H) 7.07 (t, J=8.00 Hz, 1H) 6.89 (s, 1H) 6.92-6.88 (m, 1H) 6.83 (d, J=8.20 Hz, 1H) 6.72 (d, J=8.32 Hz, 1H) 6.34 (d, J=7.70 Hz, 1H) 4.91-4.78 (s, 1H) 4.73 (q, J=8.88 Hz, 2H) 4.35 (s, 2H) 3.73-3.55 (m, 1H) 3.25-3.11 (m, 1H) 2.97-2.89 (m, 1H) 2.39 (d, J=13.20 Hz, 1H) 2.31 (s, 3H) 2.29-2.20 (m, 1H) 2.01-1.88 (m, 2H).

Example 6: Synthesis of 3-methoxy-1-[4-(2-{4-[4-(methylsulfonyl)-2-(trideuteriomethoxy)phenyl]-1-butynyl}-1-(2,2,2-trifluoroethyl)-1H-indol-4-ylamino)-1-piperidyl]-2-propanol (Compound 7)

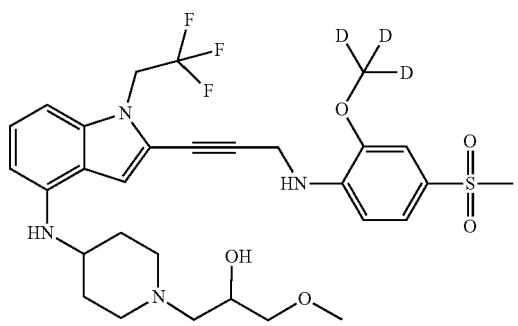 [SMILES: [2H]C([2H])([2H])Oc1cc(S(C)(=O)=O)ccc1NCC#Cc1cc2c(NC3CCN(CC(O)COC)CC3)cccc2n1CC(F)(F)F]

The compound was prepared via the following synthetic scheme:

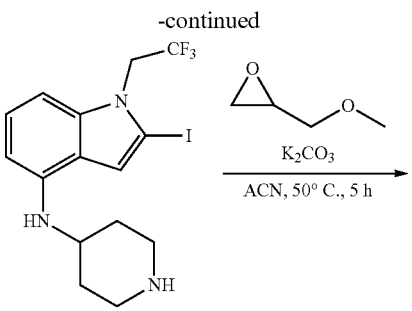

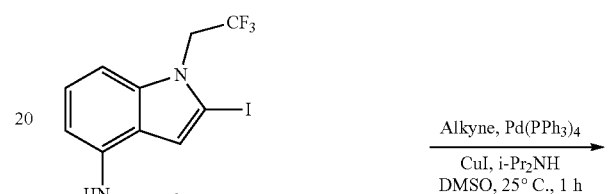

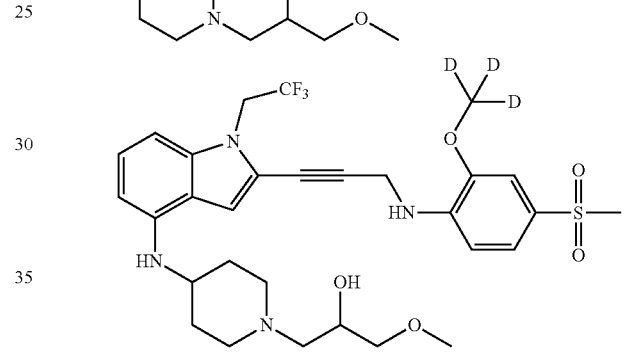

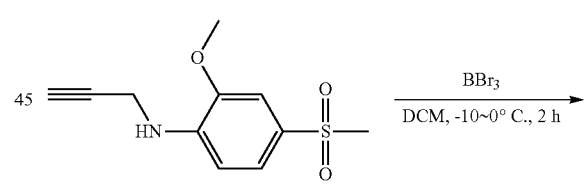

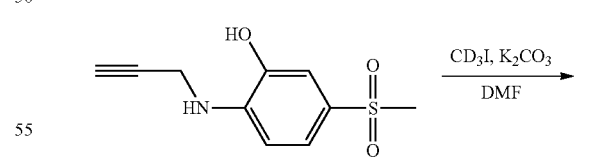

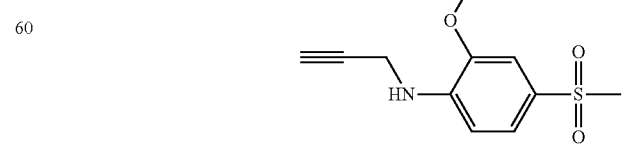

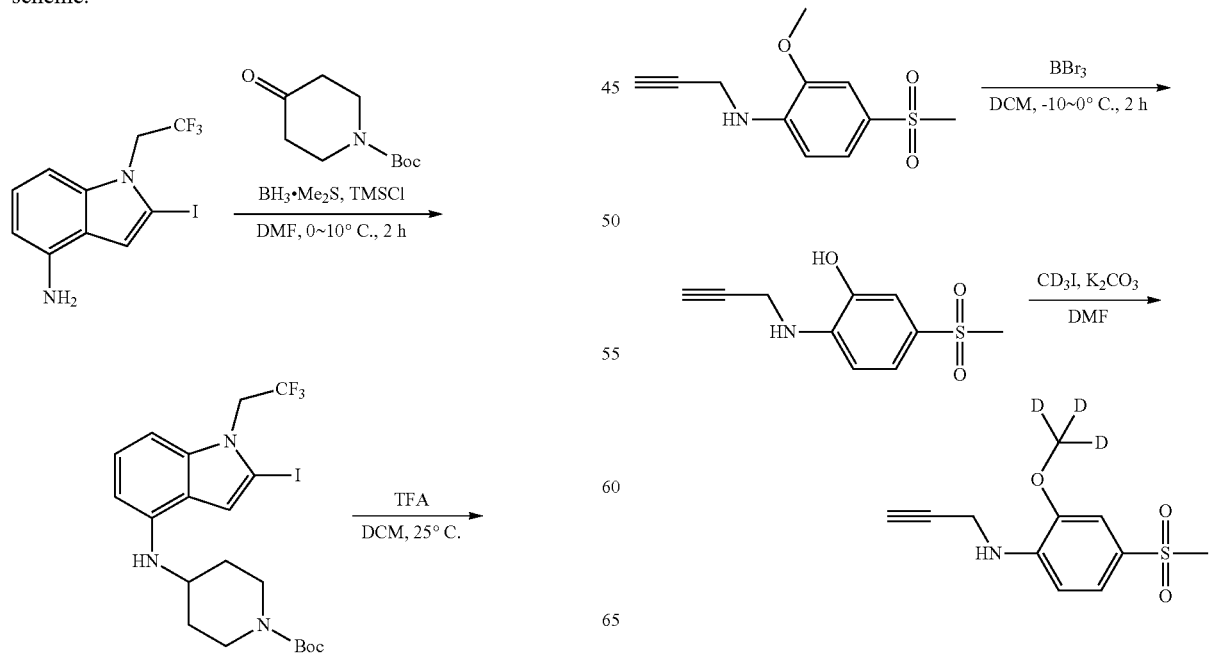

Step 1: Preparation of 4-methylsulfonyl-N-prop-2-ynyl-2-(hydroxy)aniline: 4-Methylsulfonyl-N-prop-2-ynyl-2-hydroxyaniline was prepared from 4-methylsulfonyl-N-prop-2-ynyl-2-methoxyaniline by a method similar to that described in Ex. 1, step 6.

Step 2: Preparation of 4-methylsulfonyl-N-prop-2-ynyl-2-(trideuteriomethoxy)aniline: To a mixture of 4-methylsulfonyl-N-prop-2-ynyl-2-(hydroxy)aniline (Step 1, 0.15 g, 665.89 mmol, 1 eq) in DMF (5 mL), were added $K_2CO_3$ (184.06 mg, 1.33 mmol, 2 eq) and trideuterio(iodo)methane (96.52 mg, 665.89 mmol, 41.43 mL, 1 eq). The mixture was stirred at 50° C. for 1 hr. The mixture was diluted with $H_2O$ 100 mL, then extracted with EtOAc (50 mL×2). The combined organic layers were washed with $H_2O$ (100 mL×2) and saturated salt solution (100 mL×2) in turn. The organic layer was then dried over anhydrous $Na_2SO_4$, filtered and concentrated under reduced pressure to give a residue. The residue was purified by prep-TLC ($SiO_2$, PE:EA=1:1) to yield the alkyne, 4-methylsulfonyl-N-prop-2-ynyl-2-(trideuteriomethoxy)aniline as a yellow oil. (0.13 g, 536.51 mmol, 80.57% yield).

Step 3: Preparation of 1-{4-[2-Iodo-1-(2,2,2-trifluoroethyl)-1H-indol-4-ylamino]-1-piperidyl}-3-methoxy-2-propanol: To a mixture of N-4-piperidyl[2-iodo-1-(2,2,2-trifluoroethyl)-1H-indol-4-yl]amine (prepared by a method similar to that described in Ex. 1 step 5, 5 g×2, 1 eq) in ACN (100 mL), were added $K_2CO_3$ (3 eq) and 2-(methoxymethyl)oxirane (5 eq). The mixture was stirred at 50° C. for 5 hr. The mixture was diluted with $H_2O$ (500 mL) then extracted with EtOAc (200 mL×2). The combined organic layers were washed with $H_2O$ (500 mL×2) and saturated salt solution (500 mL×2), in turn, then dried over anhydrous $Na_2SO_4$, filtered and concentrated under reduced pressure to give a residue. The residue was purified by column chromatography ($SiO_2$, petroleum ether/EtOAc=1/1 to 0:1). 1-{4-[2-Iodo-1-(2,2,2-trifluoroethyl)-1H-indol-4-ylamino]-1-piperidyl}-3-methoxy-2-propanol (10 g, 19.56 mmol) (82.77% yield) was obtained as a red solid.

Step 4: Preparation of 3-methoxy-1-[4-(2-{4-[4-(methylsulfonyl)-2-(trideuteriomethoxy)phenyl]-1-butynyl}-1-(2,2,2-trifluoroethyl)-1H-indol-4-ylamino)-1-piperidyl]-2-propanol (Compound 7): To a mixture of 4-methylsulfonyl-N-prop-2-ynyl-2-(trideuteriomethoxy)aniline (Step 2, 56.87 mg, 234.69 mmol, 1.5 eq) in DMSO (3 mL), were added i-$Pr_2NH$ (158.32 mg, 1.56 mmol, 221.12 mL, 10 eq), and CuI (5.96 mg, 31.29 mmol, 0.2 eq). 1-{4-[2-Iodo-1-(2,2,2-trifluoroethyl)-1H-indol-4-ylamino]-1-piperidyl}-3-methoxy-2-propanol (80 mg, 156.46 mmol, 1 eq) and $Pd(PPh_3)_4$ (18.08 mg, 15.65 mmol, 0.1 eq) were then added and the mixture was stirred at 25° C. for 1 hr under $N_2$. The reaction mixture was quenched by addition of EDTA saturated solution (50 mL) and EtOAc (25 mL) at 25° C. The resulting mixture was extracted with EtOAc (50 mL×2), washed with $H_2O$ (100 mL×2) and saturated salt solution (100 mL×2), in turn. The organic layers were dried over anhydrous $Na_2SO_4$, filtered and concentrated under reduced pressure to give a residue. The residue was purified by prep-TLC ($SiO_2$, DCM: MeOH=10:1), then further purified by prep-HPLC (FA condition; column: Waters Atlantis T3 150*30*5 mm; mobile phase: [water(0.225% FA)-ACN]; B %: 25%-50%, 13 min). 3-Methoxy-1-[4-(2-{4-[4-(methylsulfonyl)-2-(trideuteriomethoxy)phenyl]-1-butynyl}-1-(2,2,2-trifluoroethyl)-1H-indol-4-ylamino)-1-piperidyl]-2-propanol (Compound 7) (23.8 mg, 37.85 mmol, 24.19% yield, 99.5% purity) was obtained as a white solid. LC-MS (ES$^+$, m/z): 626.2 [(M+1)$^+$].

Example 7: Synthesis of 3-(trideuteriomethoxy)-1-[4-(2-{4-[2-methoxy-4-(methylsulfonyl)phenyl]-1-butynyl}-1-(2,2,2-trifluoroethyl)-1H-indol-4-ylamino)-1-piperidyl]-2-propanol (Compound 8)

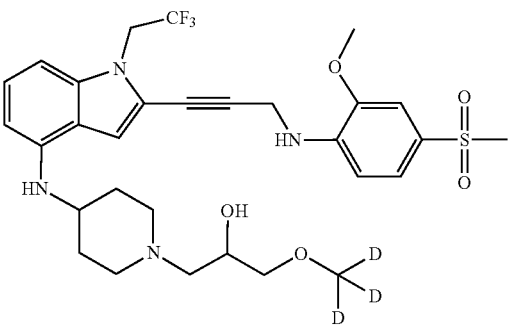 [SMILES: [2H]C([2H])([2H])OCC(O)CN1CCC(Nc2cccc3c2cc(C#CCNc2ccc(S(C)(=O)=O)cc2OC)n3CC(F)(F)F)CC1]

Step 1: Preparation of 2-[(trideuterio)methoxymethyl]oxirane: To a solution of (2-oxiranyl)methanol (300 mg, 4.05 mmol, 267.86 mL, 1 eq) in DMF (2 mL) were added NaOH (161.99 mg, 4.05 mmol, 1 eq), $CD_3I$ (587.04 mg, 4.05 mmol, 251.95 mL, 1 eq). The reaction was stirred at 25° C. for 2 h. The crude 2-[(trideuterio)methoxymethyl]oxirane was used directly in the next step.

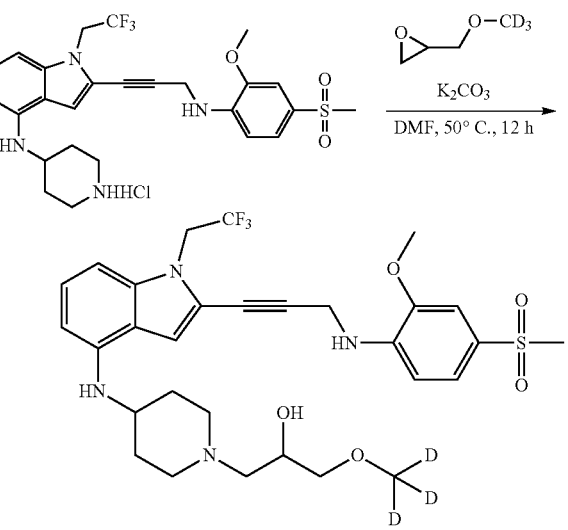

Step 2: Preparation of 3-(trideuteriomethoxy)-1-[4-(2-{4-[2-methoxy-4-(methylsulfonyl)phenyl]-1-butynyl}-1-(2,2,2-trifluoroethyl)-1H-indol-4-ylamino)-1-piperidyl]-2-propanol (Compound 8): To a mixture of N-4-piperidyl(2-{4-[2-methoxy-4-(methylsulfonyl)phenyl]-1-butynyl}-1-(2,2,2-trifluoroethyl)-1H-indol-4-yl)amine (200 mg, 374.12 mmol, 1 eq) in DMF (3 mL) were added 2-[(trideuterio)methoxymethyl]oxirane (Step 1, 102.27 mg, 1.12 mmol, 3 eq), and $K_2CO_3$ (103.41 mg, 748.23 mmol, 2 eq) at 25° C. The mixture was heated to 50° C. and stirred for 12 h. The reaction was quenched by sat. $NH_4Cl$ (20 mL) and then extracted with EtOAc (20 mL×3). The combined organic phase was washed with brine (20 mL×3), dried over anhydrous $Na_2SO_4$, filtered and concentrated. The residue was purified by TLC (DCM:MeOH=10:1, Rf=0.5), then repurified by prep-HPLC (column: Luna C18 100*30 5 m; mobile phase: [water(0.225% FA)-ACN]; B %: 10%-40%, 15 min). The desired compound was obtained as light yellow solid (11.6 mg, 18.09 mmol, 4.84% yield, 97.606% purity). LC-MS (ES+, m/z): 626.2 [(M+1)+].

Example 8: Synthesis of (1-trideuteriomethyl-4-piperidyl)(2-{4-[2-methoxy-4-(methylsulfonyl)phenyl]-1-butynyl}-1-(2,2,2-trifluoroethyl)-1H-indol-4-yl)amine (Compound 9)

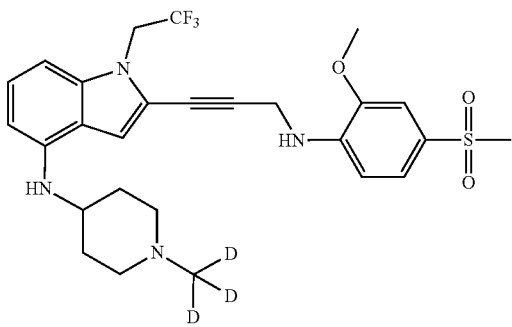 [SMILES: [2H]C([2H])([2H])N1CCC(Nc2cccc3c2cc(C#CCNc2ccc(S(C)(=O)=O)cc2OC)n3CC(F)(F)F)CC1]

The compound was prepared via the following synthetic scheme.

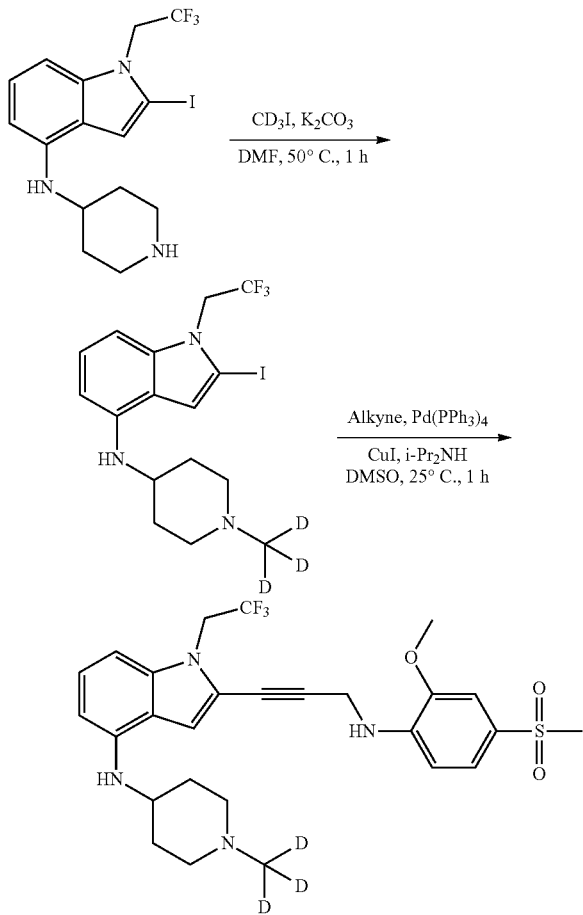

Step 1: Preparation of 1-(trideuteriomethyl)-4-piperidy[2-iodo-1-(2,2,2-trifluoroethyl)-1H-indol-4-yl]amine: To a mixture of N-4-piperidyl[2-iodo-1-(2,2,2-trifluoroethyl)-1H-indol-4-yl]amine (Example 6 Step 3, 0.2 g, 472.57 mmol, 1 eq) in DMF (5 mL), were added $K_2CO_3$ (130.63 mg, 945.15 mmol, 2 eq) and trideuterio(iodo)methane (82.20 mg, 567.09 mmol, 35.28 mL, 1.2 eq). The mixture was stirred at 50° C. for 1 hr. The reaction mixture was diluted with $H_2O$ (50 mL), then extracted with EtOAc (25 mL×2). The combined organic layers were washed with $H_2O$ (100 mL×2) and saturated salt solution (100 mL×2) in turn, then dried over anhydrous $Na_2SO_4$, filtered and concentrated under reduced pressure to give a residue. The residue was purified by prep-TLC ($SiO_2$, DCM: MeOH=10:1). The desired compound (70 mg, 159.00 mmol, 33.64% yield) was obtained as a yellow solid.

Step 2: Preparation of (1-trideuteriomethyl-4-piperidyl) (2-{4-[2-methoxy-4-(methylsulfonyl)phenyl]-1-butynyl}-1-(2,2,2-trifluoroethyl)-1H-indol-4-yl)amine (Compound 9): To a mixture of 2-methoxy-4-methylsulfonyl-N-prop-2-ynyl-aniline (40.76 mg, 170.35 mmol, 1.5 eq) in DMSO (3 mL), were added i-$Pr_2NH$ (114.92 mg, 1.14 mmol, 160.50 mL, 10 eq), and CuI (4.33 mg, 22.71 mmol, 0.2 eq). To this resulting mixture, were added the indole from Step 1 (50 mg, 113.57 mmol, 1 eq) and $Pd(PPh_3)_4$ (13.12 mg, 11.36 mmol, 0.1 eq).

The mixture was stirred at 25° C. for 1 hr under $N_2$. The reaction was quenched by addition of EDTA saturated solution(50 mL) and EtOAc (25 mL) at 25° C., then extracted with EtOAc (25 mL×2), washed with $H_2O$ (50 mL×2) and saturated salt solution (50 mL×2) in turn. The resulting organic phase was dried over anhydrous $Na_2SO_4$, filtered and concentrated under reduced pressure to give a residue. The residue was purified by prep-TLC ($SiO_2$, DCM: MeOH=10:1). The residue was purified by prep-HPLC (neutral condition; column: Waters Xbridge 150*25 5 m; mobile phase: [water (10 mM $NH_4HCO_3$)-CAN]; B %: 40%-70%, 10 min). The desired compound (24.6 mg, 44.06 mmol, 98.8% purity) was obtained as a white solid. LC-MS (ES+, m/z): 552.2 [(M+1)+].

Example 9: Synthesis of Rac-N-((3R,4S)-3-fluoro-1-methylpiperidin-4-yl)-2-(3-((2-(methoxy-d3)-4-(methylsulfonyl)phenyl)amino)prop-1-yn-1-yl)-1-(2,2,2-trifluoroethyl)-1H-indol-4-amine (Compound 10)

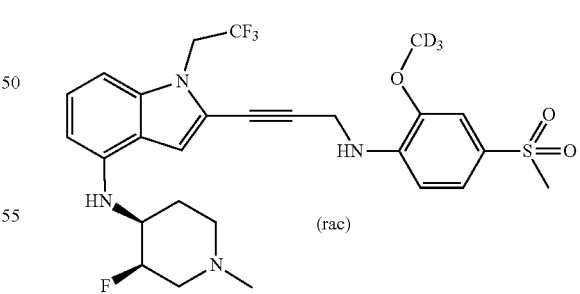

To a mixture of 4-methylsulfonyl-N-prop-2-ynyl-2-(trideuteriomethoxy)aniline (95.81 mg, 395.40 mmol, 1.2 eq) in DMSO (2 mL) was DIPEA (333.42 mg, 3.30 mmol, 465.68 mL, 10 eq) and CuI (62.75 mg, 329.50 mmol, 1 eq). To the resulting mixture, were added rac-N-[(3S,4R)-3-fluoro-1-methyl-4-piperidyl]-2-iodo-1-(2,2,2-trifluoroethyl)indol-4-ylamine (Ex. 2, 150 mg, 329.50 mmol, 1 eq) and $Pd(PPh_3)_4$ (38.08 mg, 32.95 mmol, 0.1 eq). The reaction was stirred at 25° C. for 1 hr under $N_2$. The reaction was diluted with 30 mL EtOAc and poured to 50 mL sat. EDTA, then stirred at 25° C. for 1 h. The mixture was extracted with EtOAc (40 mL×3). The combined organic layers were washed with brine (40 mL×3), dried over $Na_2SO_4$, filtered and concentrated under reduced pressure to give a residue. The residue was purified by prep-HPLC (column: Kromasil 150*25 mm*10 mm; mobile phase: [water(0.04% $NH_3H_2O$+10 mM $NH_4HCO_3$)-ACN]; B %: 30%-60%, 20 min). Rac-N-((3R,4S)-3-fluoro-1-methylpiperidin-4-yl)-2-(3-((2-(methoxy-d3)-4-(methylsulfonyl)phenyl)amino)prop-1-yn-1-yl)-1-(2,2,2-trifluoroethyl)-1H-indol-4-amine (Compound 10) (67.7 mg, 118.85 mmol, 36.07% yield, 100% purity) was obtained as a light yellow solid. LC-MS (ES+, m/z): 571.2 [(M+1)+].

Example 10: Synthesis of [(3S,4R)-3-Fluoro-1-methyl-4-piperidyl](2-{4-[2-methoxy-4-(methylsulfonyl)phenyl]-1-butynyl}-1-(2,2,2-trifluoroethyl)-1H-indol-4-yl)amine (Compound 11)

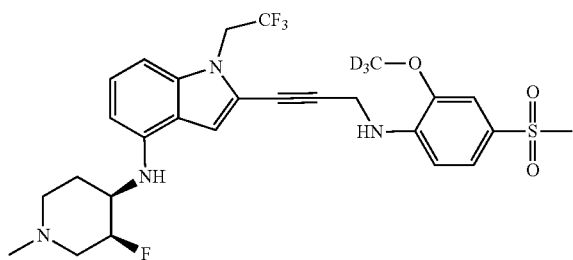

The titled compound was prepared via the following synthetic scheme.

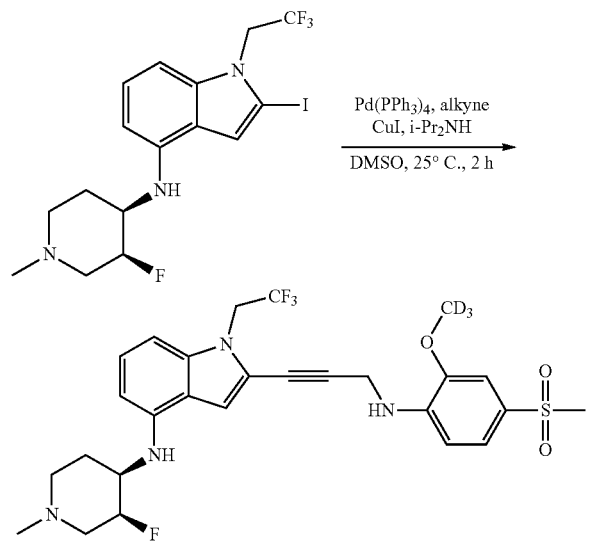

Specifically, to a solution of the alkyne, 4-methylsulfonyl-N-prop-2-ynyl-2-(trideuteriomethoxy)aniline (150.10 mg, 619.47 mmol, 1.2 eq) in DMSO (3 mL) were added i-$Pr_2NH$ (783.55 mg, 7.74 mmol, 1.09 mL, 15 eq), [(3S,4R)-3-fluoro-1-methyl-4-piperidyl][2-iodo-1-(2,2,2-trifluoroethyl)-1H-indol-4-yl]amine (250 mg, 516.22 mmol, 1 eq), CuI (19.66 mg, 103.24 mmol, 0.2 eq) and Pd(PPh3)4 (59.65 mg, 51.62 mmol, 0.1 eq). The reaction was stirred at 25° C. for 2 h under $N_2$. The reaction was poured into EDTA (Sat., aq., 20 mL). The mixture was extracted with EtOAc 60 mL (20 mL×3). The combined organic layers were washed with brine 60 mL (20 mL×3), dried over anhydrous $Na_2SO_4$, filtered and concentrated under reduced pressure. The residue was purified by column chromatography (SiO2, Petroleum ether/Ethyl acetate=1/1 to EtOAc:MeOH:TEA=10:1:0.5) and then repurified by prep-HPLC (column: Waters Xbridge Prep OBD C18 150*40 mm*10 mm; mobile phase: [water(10 mM $NH_4HCO_3$)-ACN]; B %: 45%-65%, 8 min) to afford the desired compound (110.1 mg, 192.70 mmol, 37.33% yield, 99.7% purity) as a pink solid. LC-MS (ES+, m/z): 571.2 [(M+1)+].

Example 11: Characterization of Compounds of the Disclosure

Samples are analyzed using mass spectrometry. The detected mass-to-charge ratio (m/z) and relative abundance of m/z values are used to determine the percentage of deuterated and non-deuterated compounds in a sample.

Example 12: In Vitro DNA Binding Activity Assay

The ability of a compound of the disclosure to stabilize p53 Y220C and increase the DNA binding activity of p53 Y220C was measured by a homogeneous time-resolved fluorescence (HTRF) assay. Recombinant His-tagged p53 Y220C used in the HTRF assay was expressed in the bacterium E. coli. The recombinant protein was a truncation mutant containing only amino acids 94-312 of p53, which encompassed the DNA binding domain (DBD) of p53 (SEQ ID NO.: 1). The His-tagged p53 Y220C was tested for DNA binding ability with a consensus sequence of DNA (DNA duplex with a sequence of 5 ¢-ATTAGGCATGTCTAGG-CATGTCTAGG-3 ¢; SEQ ID NO.: 2). SEQ ID NO.: 2 was then conjugated with a biotin label and used in the activity assay.

The binding of the recombinant His-tagged p53 Y220C protein and the biotin-labeled consensus DNA was measured using fluorescence resonance energy transfer (FRET). For the FRET assay, the binding between the p53 mutant and the DNA sequence was measured by detecting the fluorescence of the interaction between an anti-His antibody conjugated to allophycocyanin (APC) and streptavidin conjugated to europium to detect the biotin-labeled DNA.

The test compounds were prepared as 4.5 mM stock solutions in dimethyl sulfoxide (DMSO). The compounds of the disclosure were used to test the stabilization of p53 Y220C and increase in DNA binding activity of p53 Y220C. The stock solutions were then serially diluted 3-fold in DMSO, and 1.2 µL of the diluted solutions was added to each well of a 384-well polypropylene black plate. 30 µL of a 181 nM solution of the recombinant His-tagged p53 Y220C protein and 12.1 nM of APC conjugated anti-His tag antibody in ice-cold Assay Buffer 1 (50 mM Tris-HCl, pH 7.4; 75 mM KCl; 0.75 mM DTT; and 0.2 mg/mL bovine serum albumin (BSA) was added to each well containing the test compounds.

As a background control, 30 mL of Assay Buffer 1 containing 12.1 nM of APC anti-His antibody was also added into a second set of serially-diluted compound plates. The test and control samples were spun at 1200 rpm for 1 minute and incubated at room temperature for 15 minutes. The samples were then further incubated at either 27° C. or 29° C. for 60 min. Five microliters of 311 nM biotin labeled consensus DNA (SEQ ID NO.: 2) and 13.03 nM europium-conjugated streptavidin in Assay Buffer 2 (50 mM Tris-HCl, pH 7.4; 75 mM KCl; and 0.2 mg/mL BSA) were added to each well for both the test and control plates. The plates were spun at 1200 rpm for 1 minute and incubated at room temperature for 20 minutes. The assay signals were monitored by reading excitation at 340 nm, and emission fluorescence at 615 nm and 665 nm on a plate reader.

Normalized time-resolved fluorescence resonance energy transfer (TR-FRET) assay signal (Rn) was calculated by the formula: Rn=[(A-Ba-CD)/(D-Bd)](Dc-Bd) where A was the fluorescence intensity of the sample at 665 nm; D was the fluorescence intensity of the sample at 615 nm; Ba and Bd were plate background readings at 665 nm and 615 nm, respectively; and Dc was the fluorescence intensity of 1.8 nM Eu-SA in the assay buffer at 615 nm.

The cross-talk factor (C) was determined by the following formula: C=(Ac—Ba)/(Dc-Bd) where Ac was the fluorescence intensity of 1.8 nM Eu-labeled anti-FLAG antibody in the assay buffer at 665 nm. The percentage of activation of protein DNA binding in the presence of a compound of the disclosure compared to the absence of the compound was denoted by a $SC_{150}$ value, which indicated the concentration of the compound required to increase the DNA binding activity by 50%. The $SC_{150}$ values were calculated using either Prism™ or ActivityBase™.

TABLE 1

| +++ = 0 nM < $SC_{150}$ < 10 nM; ++ = 10 nM < $SC_{150}$ < 50 nM | |
|---|---|
| Compound | $SC_{150}$ |
| 4 | +++ |
| 5 | ++ |
| 6 | +++ |
| 7 | ++ |
| 8 | ++ |
| 9 | ++ |
| 10 | +++ |
| 11 | +++ |

Example 13: Pharmacokinetic Analysis

The pharmacokinetics (PK) of a deuterated compound and a comparator compound were measured following a 2-phase single oral (PO) administration to male cynomolgus monkeys. Compound and metabolite levels were monitored for up to 48 hours following dosing.

A group of 3 non-naïve male cynomolgus monkeys were used in this 2-phase study with a 5-day washout period between each phase. Animals in Phases 1 or 2 were administered the compounds by single oral administration at 25 mg/kg. The vehicle used for the oral studies was 2% (w/v) hydroxypropylcellulose (HPC) w/v in water ["vehicle"]. Administration was PO in fasted (overnight) animals. The fasted time was at least 12 hours prior to dosing, but the total fasted time did not exceed 20 hours. The body weights of the animals were in the range from 2.28 to 3.32 kg for males on the dosing day of Phase 1. All animals received a single oral gavage administration in each Phase.

Compound formulations were prepared in accordance with the following procedure: 257.0 mg of Compound C (4-[3-[4-[[(3S,4R)-3-fluoro-1-methyl-4-piperidyl]amino]-1-(2,2,2-trifluoroethyl)indol-2-yl]prop-2-ynylamino]-N-methyl-3-(methoxy)benzamide) was added to a pre-calibrated beaker, manually mixed with 1 mL of vehicle, stirred for 5 min to generate homogenous opaque suspension. An additional 40 mL of vehicle was added with manual mixing, and stirred for 5 min to generate a homogenous opaque suspension. An additional 9.218 mL of vehicle was added, and stirred overnight to generate a homogenous opaque suspension. 260.3 mg of Compound 3 (4-[3-[4-[[(3S,4R)-3-fluoro-1-methyl-4-piperidyl]amino]-1-(2,2,2-trifluoroethyl)indol-2-yl]prop-2-ynylamino]-N-methyl-3-(trideuteriomethoxy)benzamide) was added to a pre-calibrated beaker, manually mixed test article with 49.978 mL of vehicle, stirred for 30 min to generate a homogenous opaque suspension. Formulations were stored at room temperature for up to 15 days after preparation.

The detailed dosing and sampling regimens are described in the following table.

TABLE 2

| Group No. | No. of animals | CPD | Dose (mg/kg) | Dose Volume (mL/kg) | Target Dose Conc. (mg/mL) |
|---|---|---|---|---|---|
| 1 | 3 Male | C | 25 | 5 | 5 |
| 2 | 3 Male | 3 | 25 | 5 | 5 |

The concentrations of the compounds in all dosing solutions were determined by UPLC-UV [ACQUITY UPLC, ACQUITY UPLC BEH C8 1.7 m 2.1×100 mm Column, Mobile phase A: 0.1% FA & 2 mM $HCOONH_4$ in water/ACN (v:v, 95:5), Mobile phase B: 0.1% FA & 2 mM $HCOONH_4$ in ACN/water (v:v, 95:5)]. Three aliquots were taken from the bottom, middle and top regions of PO dosing solutions.

Plasma samples were collected at 0.25, 0.5, 1, 2, 4, 8, 12, 24 and 48 hours post-dose in Phases 1 and 2. Blank Plasma: Whole blood was collected from available stock animal into commercially available tubes containing $K_2$-EDTA on wet ice and processed for plasma. The plasma was pooled to serve as blank monkey plasma. PK plasma: Approximately 0.5 mL of blood was collected at each time point via peripheral vessel from each study animal. The actual time for each sample collection was recorded. The deviations on sampling time were less than 1 minute for the time points pre-dose through 1 hour post-dose, and less than 5% of the nominal time for time points after 1 hour post-dose. All blood samples were transferred into commercial tube (Jiangsu Kangjian medical supplies Co., Ltd.) containing K2-EDTA (0.85-1.15 mg) and placed on wet ice until processed for plasma. Plasma samples were prepared within 1 hour of collection by centrifuging the blood samples at approximately 2-8° C., 3200×g for 10 minutes. Plasma samples of about 0.1 mL×2 aliquots (one for BA, and the other one for back up) for each time point were transferred into labeled polypropylene micro-centrifuge tubes and stored frozen in a freezer set to be maintained at −60° C. or lower until LC-MS/MS analysis. Concentrations of the compounds and metabolite in plasma samples were determined by a liquid chromatography tandem mass spectrometry (LC-MS/MS) method [Triple Quad 6500 Plus, ESI (+) ionization mode, MRM detection mode]. The plasma concentration of the compounds and metabolites in study animals was subjected to a non-compartmental pharmacokinetic analysis by using the Phoenix WinNonlin software (version 6.3 or above, Pharsight). The linear/log trapezoidal rule was applied in obtaining the PK parameters. Individual plasma concentration values that were below the lower limit of quantitation (LLOQ) were excluded from the PK parameter calculation. The nominal dose levels and nominal sampling times were used in the calculation of all pharmacokinetic parameters.

Following oral administration of the compounds at 25 mg/kg in male cynomolgus monkeys, the area under the plasma concentration-time curve from time zero to the last quantifiable concentration (AUC$_{0-24}$) values of the comparator Compound C and Compound 3 were 66942±25843, and 107359±29193 ng h/mL, respectively. This shows an increase in AUC of about 60% over Compound C. Additionally, the C$_{max}$ values of the comparator Compound C and Compound 3 were 5667±3003, and 10017±4175 ng/mL, respectively, while T$_{max}$ of the comparator Compound C and Compound 3 was 2.67±1.15 h, and 2.00 h, respectively. The mean PK parameters of the compounds are summarized below.

TABLE 3

| Phase No. | 1 | | 2 | |
|---|---|---|---|---|
| Administered compound | Compound C | | Compound 3 | |
| Nominal dose (mg/kg) | 25 | | 25 | |
| Analyte | Compound C | | Compound 3 | |
| PK Parameters | Mean | SD | Mean | SD |
| Cmax (ng/mL) | 5667 | 3003 | 10017 | 4175 |
| Tmax (h) | 2.67 | 1.15 | 2.00 | 0.00 |
| T1/2 (h) | 6.73 | 0.455 | 6.37 | 0.248 |
| AUC0-24 (ng · h/mL) | 66942 | 25843 | 107359 | 29193 |
| AUC0-last (ng · h/mL) | 74174 | 27701 | 117710 | 32103 |
| AUC0-inf (ng · h/mL) | 74827 | 28047 | 118439 | 32430 |
| AUCExtra (%) | 0.845 | 0.190 | 0.599 | 0.109 |

The mean PK parameters of the parent compounds and two glucuronidation metabolites are summarized in TABLE 4. Compound 3 showed a reduction in both glucuronidation metabolites [70% and 10%].

TABLE 4

| Compound Biotransformation | | | | |
|---|---|---|---|---|
| Compound (Dose) | Compound C (25 mg/kg) | | Compound 3 (25 mg/kg) | |
| Analyte | AUC$_{0-24}$ | % of total analyte area | AUC$_{0-24}$ (% Rel. to Cpd C value) | % of total analyte area |
| Parent | 66.9 | 26.4 | 107 (160%) | 42.0 |
| O-Demethylation/ Glucuronidation | 111 | 44.8 | 78.3 (70%) | 30.7 |
| O-Demethylation/Glucuronidation/ N-Oxidation | 69.4 | 27.4 | 63.5 (91%) | 24.9 |

Embodiments

The following non-limiting embodiments provide illustrative examples of the present disclosure, but do not limit the scope of the disclosure.

Embodiment 1. A Compound of Formula L:

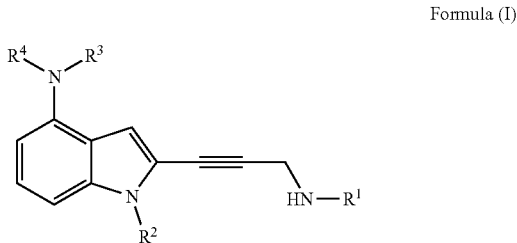

Formula (I)

wherein:
R$^1$ is selected from aryl, heteroaryl, and heterocyclyl, each of which is independently unsubstituted or substituted with one, two or three substituents selected from hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, —P(O)R$^{21}$, and an ester group;
R$^2$ is alkyl, alkenyl, alkynyl, aryl, heteroaryl, or heterocyclyl, each of which is independently unsubstituted or substituted with one, two or three substituents selected from a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, —P(O)R$^{21}$, and an ester group; or hydrogen, —C(O)R$^{21}$, —C(O)OR$^{21}$, —C(O)NR$^{21}$R$^{22}$, —OR$^{21}$, —SR$^{21}$, —NR$^{21}$R$^{22}$, —NR$^{21}$C(O)R$^{22}$, or —OC(O)R$^{21}$;
R$^3$ is H;
R$^4$ is heterocyclyl substituted with one, two or three substituents selected from a halogen group, a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group —P(O)R$^{21}$, and an ester group; and
each R$^{21}$ and R$^{22}$ is independently hydrido, alkyl, alkenyl, alkynyl, aryl, heteroaryl, or heterocyclyl, each of which is independently unsubstituted or substituted with one, two or three substituents selected from a halogen group, a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, and an ester group; and
wherein the compound comprises at least one deuterium or deuterio [D] group;
wherein each position designated specifically as D, deuterio or deuterium has at least about 10% deuterium incorporation;
or a pharmaceutically-acceptable salt thereof.

Embodiment 2. The compound of Embodiment 1, wherein $R^1$ is aryl substituted with one, two or three substituents selected from alkylsulfonyl, alkoxy, alkylaminocarbonyl, deuterated alkoxy and (deuterated alkyl)aminocarbonyl.

Embodiment 3. The compound of Embodiment 2, wherein $R^1$ is phenyl substituted with one, two or three substituents selected from $C_{1-4}$ alkylsulfonyl, $C_{1-4}$ alkoxy, $C_{1-4}$ alkylaminocarbonyl, deuterated $C_{1-4}$ alkoxy and (deuterated $C_{1-4}$ alkyl)aminocarbonyl.

Embodiment 4. The compound of Embodiment 3, wherein $R^1$ is phenyl substituted with one, two or three substituents selected from methylsulfonyl, methoxy, methylaminocarbonyl, trideuteriomethoxy or (trideuteriomethyl)aminocarbonyl.

Embodiment 5. The compound of Embodiment 1, wherein $R^2$ is alkyl, unsubstituted or substituted with halo.

Embodiment 6. The compound of Embodiment 5, wherein $R^2$ is $C_{1-4}$ haloalkyl.

Embodiment 7. The compound of Embodiment 6, wherein $R^2$ is 1,1,1-trifluoroethyl.

Embodiment 8. The compound of Embodiment 1, wherein $R^4$ is 4-piperidinyl unsubstituted or substituted with one, two or three substituents selected from halo, $C_{1-4}$ alkyl, and $C_{1-4}$ alkoxy-(hydroxy)-$C_{1-4}$ alkyl.

Embodiment 9. The compound of Embodiment 8, wherein $R^4$ is 4-piperidinyl substituted with fluoro and one or two additional substituents selected from methyl, trideuteriomethyl, tert-butyl, 2-hydroxy-methoxypropyl and 2-hydroxy-trideuteriomethoxypropyl.

Embodiment 10. The compound of Embodiment 1, of the formula

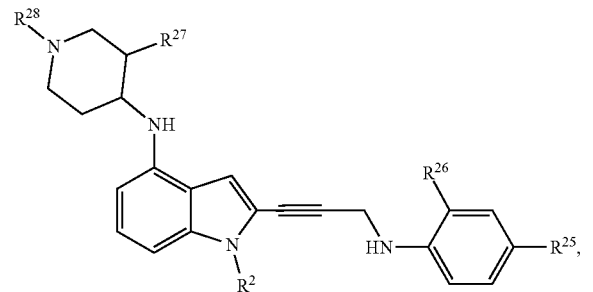

wherein:
$R^2$ is $C_1$-$C_4$ haloalkyl,
$R^{25}$ is selected from hydrido, a hydroxyl group, sulfhydryl group, halogen, amino group, nitro group, nitroso group, cyano group, azido group, sulfoxide group, alkyl sulfonyl group, sulfonamide group, carboxyl group, carboxaldehyde group, imine group, alkyl group, halo-alkyl group, alkenyl group, halo-alkenyl group, alkynyl group, halo-alkynyl group, alkoxy group, deuterated alkoxy group, aryl group, aryloxy group, aralkyl group, arylalkoxy group, heterocyclyl group, acyl group, acyloxy group, carbamate group, amide group, deuterated alkyl amide group, ureido group, epoxy group, —P(O)$R^{21}$, and an ester group;

$R^{26}$ is selected from hydrido, a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, alkenyl group, halo-alkenyl group, alkynyl group, halo-alkynyl group, alkoxy group, deuterated alkoxy group, aryl group, aryloxy group, aralkyl group, arylalkoxy group, heterocyclyl group, acyl group, acyloxy group, carbamate group, amide group, deuterated amide group, ureido group, epoxy group, —P(O)$R^{21}$, and an ester group;

$R^{27}$ is selected from hydrido, substituted with a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, —P(O)$R^{21}$, and an ester group;

$R^{28}$ is selected from hydrido, a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, deuterated alkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, —P(O)$R^{21}$, and an ester group;

provided one or more of $R^{25}$, $R^{26}$, $R^{27}$ or $R^{28}$ is a deuterated group;
or a pharmaceutically-acceptable salt thereof.

Embodiment 11. The compound of Embodiment 10, wherein:
$R^2$ is 1,1,1-trifluoroethyl;
$R^{25}$ is selected from $C_1$-$C_4$ alkylaminocarbonyl, deuterated $C_1$-$C_4$ alkylaminocarbonyl or $C_1$-$C_4$ alkylsulfonyl;
$R^{26}$ is $C_1$-$C_4$ alkoxy, or deuterated $C_1$-$C_4$ alkoxy;
$R^{27}$ is hydrido, or fluoro; and
$R^{28}$ is selected from $C_1$-$C_4$ alkyl, deuterated $C_1$-$C_4$ alkyl, optionally hydroxy substituted $C_1$-$C_4$ alkoxy-$C_1$-$C_4$ alkyl, or optionally hydroxy substituted deuterated $C_1$-$C_4$ alkoxy-$C_1$-$C_4$ alkyl.

Embodiment 12. The compound of Embodiment 11, wherein:
$R^{25}$ is methylsuflonyl, methylaminocarbonyl, or trideuteriomethylaminocarbonyl;
$R^{26}$ is methoxy, or trideuteriomethoxy; and
$R^{28}$ is selected from methyl, tert-butyl, deuterated methyl, 2-hydroxy-1-methoxypropyl, or 1-trideuteriomethoxy-2-hydroxypropyl.

Embodiment 13. The compound of Embodiment 10, wherein the compound has the formula:
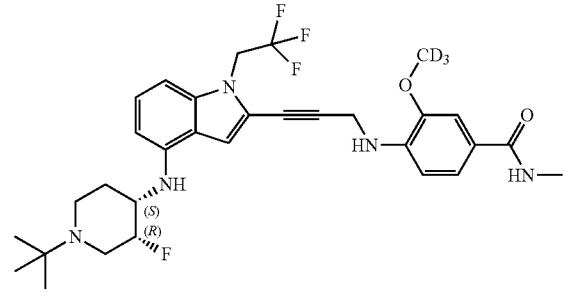
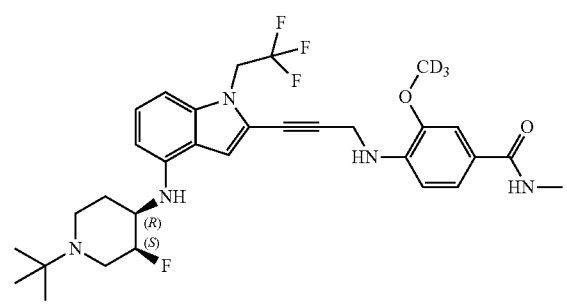
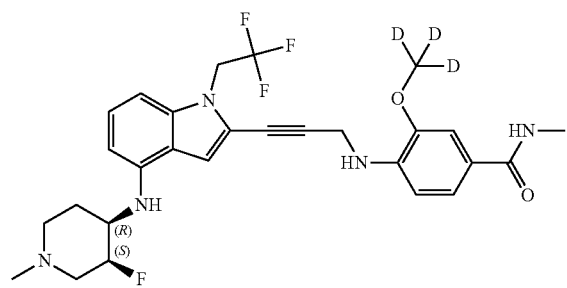
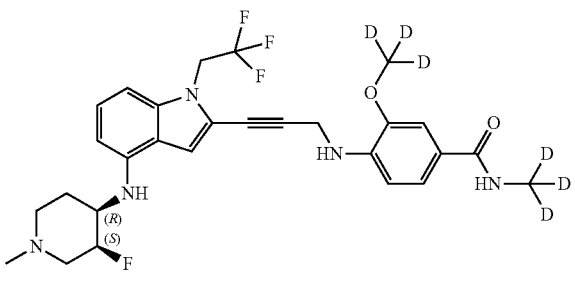
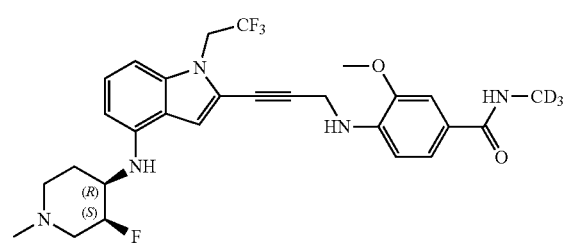
-continued
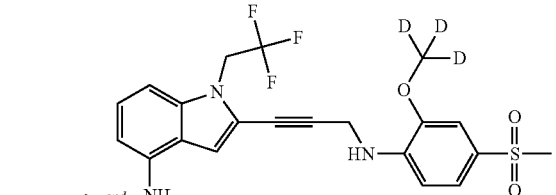
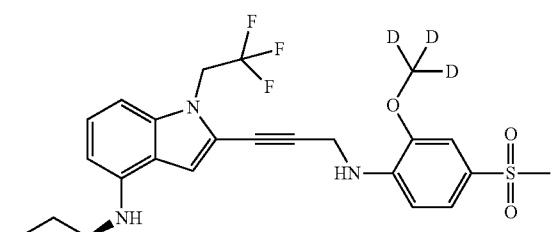
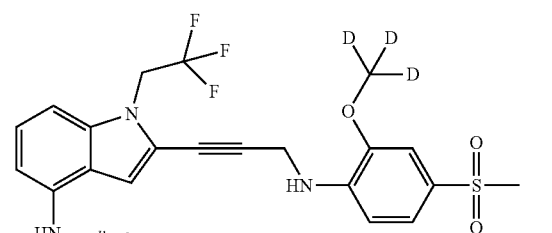
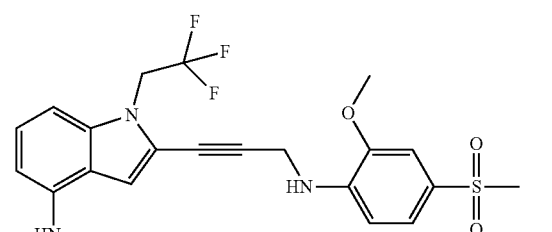
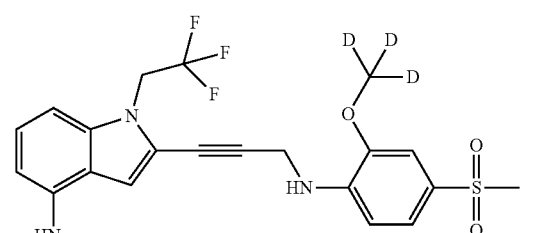

-continued

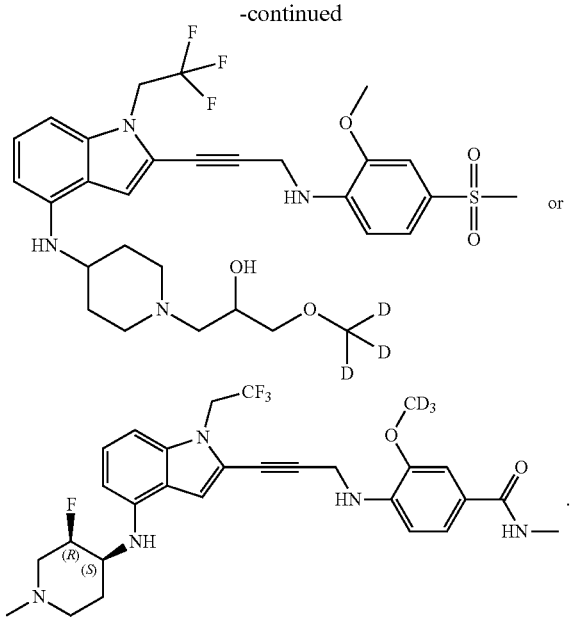

Embodiment 14. A method of inducing apoptosis in a cell, the method comprising contacting the cell with a therapeutically-effective amount of a compound that binds a p53 mutant, wherein the compound is a compound of any one of Embodiments 1-13.

Embodiment 15. The method of Embodiment 14, wherein the compound increases the ability of the p53 mutant to bind to DNA.

Embodiment 16. The method of Embodiment 14, wherein the p53 mutant is p53 Y220C.

Embodiment 17. The method of Embodiment 14, wherein the compound induces a conformational change in the p53 mutant.

Embodiment 18. The method of Embodiment 14, wherein the compound increases a stability of a biologically-active conformation of the p53 mutant relative to a stability of the biologically-active conformation of the p53 mutant in an absence of the compound.

Embodiment 19. A method of treating a cancer, the method comprising administering to a subject in need thereof a therapeutically-effective amount of a compound of any one of Embodiments 1-13, wherein the compound has an $SC_{150}$ value for p53 Y220C of less than 1 mM as measured by a homogeneous time-resolved fluorescence (HTRF) assay.

Embodiment 20. The method of Embodiment 19, wherein the administering is intravenous.

Embodiment 21. The method of Embodiment 19, wherein the administering is oral.

Embodiment 22. The method of Embodiment 9, wherein the administering is intratumoral.

Embodiment 23. The method of Embodiment 19, wherein the therapeutically-effective amount is from about 20 mg/kg to about 400 mg/kg.

Embodiment 24. The method of Embodiment 19, wherein the cancer is breast cancer.

Embodiment 25. The method of Embodiment 19, wherein the cancer is lung cancer.

Embodiment 26. The method of Embodiment 19, wherein the compound increases a stability of a biologically-active conformation of the p53 mutant relative to a stability of the biologically-active conformation of the p53 mutant in an absence of the compound.

Embodiment 27. The method of Embodiment 19, wherein the compound has an $SC_{150}$ value of less than about 50 nM.

Embodiment A1. A composition comprising a population of molecules, wherein the population of molecules has a mass of at least 1 μg, wherein at least 10% of the molecules in the population of molecules each independently comprise a deuterium atom, wherein each molecule is a compound of formula I:

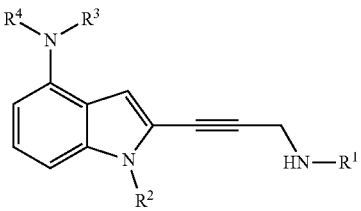

Formula I wherein:
$R^1$ is selected from aryl, heteroaryl, and heterocyclyl, each of which is independently unsubstituted or substituted with one, two or three substituents selected from hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, —P(O)$R^{21}$, and an ester group;

$R^2$ is selected from hydrido, —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, —OC(O)$R^{21}$, alkyl, alkenyl, alkynyl, aryl, heteroaryl, or heterocyclyl, each of which is independently unsubstituted or substituted with one, two or three substituents selected from a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, —P(O)$R^{21}$, and an ester group;

$R^3$ is H;
$R^4$ is heterocyclyl substituted with one, two or three substituents selected from a halogen group, a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, —P(O)$R^{21}$, and an ester group; and each $R^{21}$ and $R^{22}$ is independently hydrido, alkyl, alkenyl, alkynyl, aryl, heteroaryl, or heterocyclyl, each of which is independently unsubstituted or substituted with one, two or three substituents selected from a halogen group, a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, and an ester group; and wherein the compound is optionally substituted with at least one deuterio [D] group;
or a pharmaceutically-acceptable salt thereof.

Embodiment A2. The composition of embodiment A1, wherein at least 50% of the molecules in the population of molecules each independently comprise a deuterium atom.

Embodiment A3. The composition of embodiment A1, wherein at least 90% of the molecules in the population of molecules each independently comprise a deuterium atom.

Embodiment A4. The composition of embodiment A1, wherein at least 95% of the molecules in the population of molecules each independently comprise a deuterium atom.

Embodiment A5. The composition of embodiment A1, wherein at least 99% of the molecules in the population of molecules each independently comprise a deuterium atom.

Embodiment A6. The composition of embodiment A1, wherein at least 10% of the molecules in the population of molecules each independently comprise a deuterium atom at a common position.

Embodiment A7. The composition of embodiment A1, wherein at least 50% of the molecules in the population of molecules each independently comprise a deuterium atom at a common position.

Embodiment A8. The composition of embodiment A1, wherein at least 90% of the molecules in the population of molecules each independently comprise a deuterium atom at a common position.

Embodiment A9. The composition of embodiment A1, wherein at least 95% of the molecules in the population of molecules each independently comprise a deuterium atom at a common position.

Embodiment A10. The composition of embodiment A1, wherein at least 99% of the molecules in the population of molecules each independently comprise a deuterium atom at a common position.

Embodiment A11. The composition of embodiment A1, wherein at least 10% of the molecules in the population of molecules each independently comprise a $CD_3$ group at a common position.

Embodiment A12. The composition of embodiment A1, wherein at least 50% of the molecules in the population of molecules each independently comprise a $CD_3$ group at a common position.

Embodiment A13. The composition of embodiment A1, wherein at least 90% of the molecules in the population of molecules each independently comprise a $CD_3$ group at a common position.

Embodiment A14. The composition of embodiment A1, wherein at least 95% of the molecules in the population of molecules each independently comprise a $CD_3$ group at a common position.

Embodiment A15. The composition of embodiment A1, wherein at least 99% of the molecules in the population of molecules each independently comprise a $CD_3$ group at a common position.

Embodiment A16. The composition of embodiment A1, wherein the population of molecules has a mass of at least 1 mg.

Embodiment A17. The composition of embodiment A1, wherein the population of molecules has a mass of at least 100 mg.

Embodiment A18. The composition of embodiment A1, wherein the population of molecules has a mass of at least 1 kg.

Embodiment A19. The composition of embodiment A1, wherein the population of molecules has a mass of at least 100 kg.

Embodiment A20. The composition of embodiment A1, wherein the population of molecules has a mass that is therapeutically effective for treatment of a cancer.

Embodiment B1. A composition comprising a population of molecules, wherein the population of molecules has a mass of at least 1 µg, wherein if, in a mass spectrometry experiment, a mass spectrum of the population is obtained, the mass spectrometry experiment determines that at least 10% of the molecules in the population of molecules each independently comprise a deuterium atom, wherein each molecule is a compound of formula I:

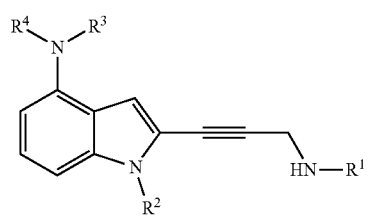

Formula I wherein:
$R^1$ is selected from aryl, heteroaryl, and heterocyclyl, each of which is independently unsubstituted or substituted with one, two or three substituents selected from hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, —P(O)$R^{21}$, and an ester group;

$R^2$ is alkyl, alkenyl, alkynyl, aryl, heteroaryl, or heterocyclyl, each of which is independently unsubstituted or substituted with one, two or three substituents selected from a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, —P(O)$R^{21}$, and an ester group; or hydrogen, —C(O)R²¹, —C(O)OR²¹, —C(O)NR²¹R²², —OR²¹, —SR²¹, —NR²¹R²², —NR²¹C(O)R²², or —OC(O)R²¹;

R³ is H;

R⁴ is heterocyclyl substituted with one, two or three substituents selected from a halogen group, a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, —P(O)R²¹, and an ester group; and each R²¹ and R²² is independently hydrido, alkyl, alkenyl, alkynyl, aryl, heteroaryl, or heterocyclyl, each of which is independently unsubstituted or substituted with one, two or three substituents selected from a halogen group, a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, and an ester group; and wherein the compound is optionally comprises at least one deuterio [D] group; or a pharmaceutically-acceptable salt thereof.

Embodiment B2. The composition of embodiment B1, wherein the mass spectrometry experiment determines at least 50% of the molecules in the population of molecules each independently comprise a deuterium atom.

Embodiment B3. The composition of embodiment B1, wherein the mass spectrometry experiment determines at least 90% of the molecules in the population of molecules each independently comprise a deuterium atom.

Embodiment B4. The composition of embodiment B1, wherein the mass spectrometry experiment determines at least 95% of the molecules in the population of molecules each independently comprise a deuterium atom.

Embodiment B5. The composition of embodiment B1, wherein the mass spectrometry experiment determines at least 99% of the molecules in the population of molecules each independently comprise a deuterium atom.

Embodiment B6. The composition of embodiment B1, wherein the mass spectrometry experiment determines at least 10% of the molecules in the population of molecules each independently comprise three deuterium atoms.

Embodiment B7. The composition of embodiment B1, wherein the mass spectrometry experiment determines at least 50% of the molecules in the population of molecules each independently comprise three deuterium atoms.

Embodiment B8. The composition of embodiment B1, wherein the mass spectrometry experiment determines at least 90% of the molecules in the population of molecules each independently comprise three deuterium atoms.

Embodiment B9. The composition of embodiment B1, wherein the mass spectrometry experiment determines at least 95% of the molecules in the population of molecules each independently comprise three deuterium atoms.

Embodiment B10. The composition of embodiment B1, wherein the mass spectrometry experiment determines at least 99% of the molecules in the population of molecules each independently comprise three deuterium atoms.

Embodiment B11. The composition of embodiment B1, wherein the population of molecules has a mass of at least 1 mg.

Embodiment B12. The composition of embodiment B1, wherein the population of molecules has a mass of at least 100 mg.

Embodiment B13. The composition of embodiment B1, wherein the population of molecules has a mass of at least 1 kg.

Embodiment B14. The composition of embodiment B1, wherein the population of molecules has a mass of at least 100 kg.

Embodiment B15. The composition of embodiment B1, wherein the population of molecules has a mass that is therapeutically effective for treatment of a cancer.

Embodiment B16. The composition of embodiment B1, wherein if a ¹H nuclear magnetic resonance experiment is performed on a 500 MHz NMR instrument using a sample of the population of molecules in CDCl₃ to provide a result, and the result is compared to a ¹H nuclear magnetic resonance spectrum obtained on the 500 MHz NMR instrument of an analogous population of molecules that contains a natural isotopic abundance of deuterium in CDCl₃, then the nuclear magnetic resonance experiment indicates that at least 10% of the molecules in the population of molecules each independently comprise a CD₃ group at a common position.

Embodiment B17. The composition of embodiment B16, wherein the nuclear magnetic resonance experiment indicates that at least 50% of the molecules in the population of molecules each independently comprise a CD₃ group at a common position.

Embodiment B18. The composition of embodiment B16, wherein the nuclear magnetic resonance experiment indicates that at least 90% of the molecules in the population of molecules each independently comprise a CD₃ group at a common position.

Embodiment B19. The composition of embodiment B16, wherein the nuclear magnetic resonance experiment indicates that at least 95% of the molecules in the population of molecules each independently comprise a CD₃ group at a common position.

Embodiment B20. The composition of embodiment B16, wherein the nuclear magnetic resonance experiment indicates that at least 99% of the molecules in the population of molecules each independently comprise a CD₃ group at a common position.

Embodiment C1. A composition comprising a population of molecules, wherein the population of molecules has a mass of at least 1 µg, wherein if, in a mass spectrometry experiment, a mass spectrum of the population is obtained, the mass spectrometry experiment identifies a molecular ion having a mass of 549.3±0.5, wherein each molecule is:

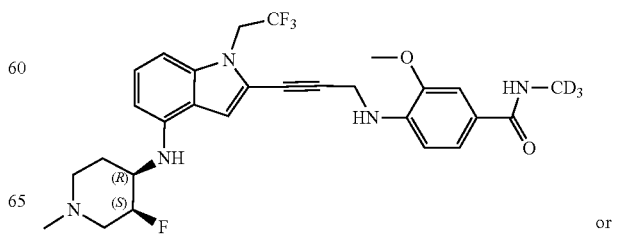

or

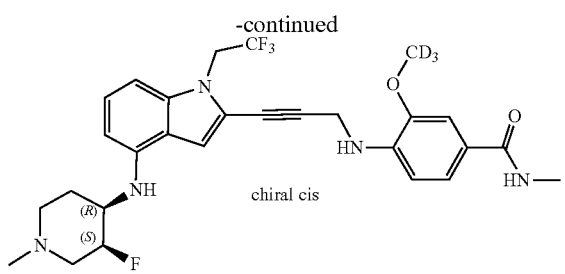

or a pharmaceutically-acceptable salt thereof.

Embodiment C2. The composition of embodiment $C_1$, wherein the population of molecules has a mass of at least 1 mg.

Embodiment C3. The composition of embodiment $C_1$, wherein the population of molecules has a mass of at least 100 mg.

Embodiment C4. The composition of embodiment $C_1$, wherein the population of molecules has a mass of at least 1 kg.

Embodiment C5. The composition of embodiment $C_1$, wherein the population of molecules has a mass of at least 100 kg.

Embodiment C6. The composition of embodiment $C_1$, wherein the population of molecules has a mass that is therapeutically effective for treatment of a cancer.

Embodiment C7. The composition of embodiment $C_1$, wherein if a $^1$H nuclear magnetic resonance experiment is performed on a 500 MHz NMR instrument using a sample of the population of molecules in $CDCl_3$ to provide a result, and the result is compared to a $^1$H nuclear magnetic resonance spectrum obtained on the 500 MHz NMR instrument of an analogous population of molecules that contains a natural isotopic abundance of deuterium in $CDCl_3$, then the nuclear magnetic resonance experiment indicates that the molecular ion represents a structure having a $CD_3$ group.

Embodiment D1. A method of treating a cancer, the method comprising administering to a subject in need thereof a therapeutically-effective amount of a pharmaceutical composition, wherein the pharmaceutical composition comprises a population of molecules, wherein at least 10% of the molecules in the population of molecules each independently comprise a deuterium atom, wherein each molecule in the population of molecules is a compound that binds to a non-wild type p53 protein and reconforms the non-wild type p53 protein to a conformation of p53 that exhibits anti-cancer activity.

Embodiment D2. The method of embodiment D1, wherein the non-wild type p53 protein comprises a mutation at Y220C.

Embodiment D3. The method of embodiment D1, wherein the compound selectively binds the non-wild type p53 protein compared to a wild-type p53 protein.

Embodiment D4. The method of embodiment D1, wherein at least 50% of the molecules in the population of molecules each independently comprise a deuterium atom.

Embodiment D5. The method of embodiment D1, wherein at least 90% of the molecules in the population of molecules each independently comprise a deuterium atom.

Embodiment D6. The method of embodiment D1, wherein at least 95% of the molecules in the population of molecules each independently comprise a deuterium atom.

Embodiment D7. The method of embodiment D1, wherein at least 99% of the molecules in the population of molecules each independently comprise a deuterium atom.

Embodiment D8. The method of embodiment D1, wherein at least 10% of the molecules in the population of molecules each independently comprise a deuterium atom at a common position.

Embodiment D9. The method of embodiment D1, wherein at least 50% of the molecules in the population of molecules each independently comprise a deuterium atom at a common position.

Embodiment D10. The method of embodiment D1, wherein at least 90% of the molecules in the population of molecules each independently comprise a deuterium atom at a common position.

Embodiment D11. The method of embodiment D1, wherein at least 95% of the molecules in the population of molecules each independently comprise a deuterium atom at a common position.

Embodiment D12. The method of embodiment D1, wherein at least 99% of the molecules in the population of molecules each independently comprise a deuterium atom at a common position.

Embodiment D13. The method of embodiment D1, wherein at least 10% of the molecules in the population of molecules each independently comprise a $CD_3$ group at a common position.

Embodiment D14. The method of embodiment D1, wherein at least 50% of the molecules in the population of molecules each independently comprise a $CD_3$ group at a common position.

Embodiment D15. The method of embodiment D1, wherein at least 90% of the molecules in the population of molecules each independently comprise a $CD_3$ group at a common position.

Embodiment D16. The method of embodiment D1, wherein at least 95% of the molecules in the population of molecules each independently comprise a $CD_3$ group at a common position.

Embodiment D17. The method of embodiment D1, wherein at least 99% of the molecules in the population of molecules each independently comprise a $CD_3$ group at a common position.

Embodiment E1. A method of treating a cancer, the method comprising administering to a subject in need thereof a therapeutically-effective amount of a pharmaceutical composition, wherein the pharmaceutical composition comprises a population of molecules, wherein if, in a mass spectrometry experiment, a mass spectrum of the population is obtained, the mass spectrometry experiment determines that at least 10% of the molecules in the population of molecules each independently comprise a deuterium atom, wherein each molecule in the population of molecules is a compound that binds to a non-wild type p53 protein and reconforms the non-wild type p53 protein to a conformation of p53 that exhibits anti-cancer activity.

Embodiment E2. The method of embodiment E1, wherein the non-wild type p53 protein comprises a mutation at Y220C.

Embodiment E3. The method of embodiment E1, wherein the compound selectively binds the non-wild type p53 protein compared to a wild-type p53 protein.

Embodiment E4. The method of embodiment E1, wherein the mass spectrometry experiment determines at least 50% of the molecules in the population of molecules each independently comprise a deuterium atom.

Embodiment E5. The method of embodiment E1, wherein the mass spectrometry experiment determines at least 90% of the molecules in the population of molecules each independently comprise a deuterium atom.

Embodiment E6. The method of embodiment E1, wherein the mass spectrometry experiment determines at least 95% of the molecules in the population of molecules each independently comprise a deuterium atom.

Embodiment E7. The method of embodiment E1, wherein the mass spectrometry experiment determines at least 99% of the molecules in the population of molecules each independently comprise a deuterium atom.

Embodiment E8. The method of embodiment E1, wherein the mass spectrometry experiment determines at least 10% of the molecules in the population of molecules each independently comprise three deuterium atoms.

Embodiment E9. The method of embodiment E1, wherein the mass spectrometry experiment determines at least 50% of the molecules in the population of molecules each independently comprise three deuterium atoms.

Embodiment E10. The method of embodiment E1, wherein the mass spectrometry experiment determines at least 90% of the molecules in the population of molecules each independently comprise three deuterium atoms.

Embodiment E11. The method of embodiment E1, wherein the mass spectrometry experiment determines at least 95% of the molecules in the population of molecules each independently comprise three deuterium atoms.

Embodiment E12. The method of embodiment E1, wherein the mass spectrometry experiment determines at least 99% of the molecules in the population of molecules each independently comprise three deuterium atoms.

Embodiment E13. The method of embodiment E1, wherein the cancer is ovarian cancer.

Embodiment E14. The method of embodiment E1, wherein the cancer is breast cancer.

Embodiment E15. The method of embodiment E1, wherein the cancer is pancreatic cancer.

Embodiment E16. The method of embodiment E1, wherein the cancer is lung cancer.

Embodiment E17. The method of embodiment E1, wherein the therapeutically-effective amount of the pharmaceutical composition comprises from about 500 mg to about 2000 mg of the compound.

Embodiment E18. The method of embodiment E1, wherein the therapeutically-effective amount of the pharmaceutical composition comprises about 600 mg of the compound.

Embodiment E19. Embodiment E18. The method of embodiment E1, wherein the therapeutically-effective amount of the pharmaceutical composition comprises about 1200 mg of the compound.

Embodiment E20. Embodiment E18. The method of embodiment E1, wherein the therapeutically-effective amount of the pharmaceutical composition comprises about 2000 mg of the compound.

Embodiment F1. A method of treating a cancer, the method comprising administering to a subject in need thereof a therapeutically-effective amount of a pharmaceutical composition, wherein the pharmaceutical composition comprises a population of molecules, wherein if, in a mass spectrometry experiment, a mass spectrum of the population is obtained, the mass spectrometry experiment identifies a molecular ion having a mass of 548.58±0.5, wherein each molecule in the population of molecules is a compound that binds to a non-wild type p53 protein and reconforms the non-wild type p53 protein to a conformation of p53 that exhibits anti-cancer activity.

Embodiment F2. The method of embodiment F1, wherein if a $^1$H nuclear magnetic resonance experiment is performed on a 500 MHz NMR instrument using a sample of the population of molecules in $CDCl_3$ to provide a result, and the result is compared to a $^1$H nuclear magnetic resonance spectrum obtained on the 500 MHz NMR instrument of an analogous population of molecules that contains a natural isotopic abundance of deuterium in $CDCl_3$, then the nuclear magnetic resonance experiment indicates that the molecular ion represents a structure having a $CD_3$ group.

---

What is claimed is:

1. A composition comprising a population of molecules, wherein the population of molecules has a mass of at least 1 μg, wherein at least 10% of the molecules in the population of molecules each independently comprise a deuterium atom, wherein each molecule is a compound of Formula (I):

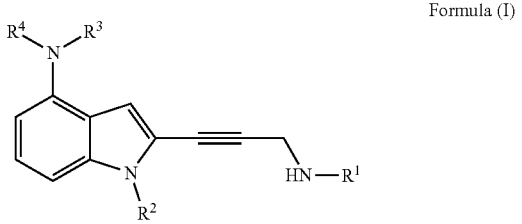

Formula (I)

wherein:
- $R^1$ is selected from aryl, heteroaryl, and heterocyclyl, each of which is independently unsubstituted or substituted with one, two or three substituents selected from hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, and an ester group;
- $R^2$ is selected from hydrogen, —C(O)R$^{21}$, —C(O)OR$^{21}$, —C(O)NR$^{21}$R$^{22}$, —OR$^{21}$, —SR$^{21}$, —NR$^{21}$R$^{22}$, —NR$^{21}$C(O)R$^{22}$, —OC(O)R$^{21}$, alkyl, alkenyl, alkynyl, aryl, heteroaryl, and heterocyclyl, each of which is independently unsubstituted or substituted with one, two or three substituents selected from a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, and an ester group;
- $R^3$ is H;
- $R^4$ is heterocyclyl substituted with one, two or three substituents selected from a halogen group, a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, and an ester group; and
- each $R^{21}$ and $R^{22}$ is independently hydrido, alkyl, alkenyl, aryl, heteroaryl, or heterocyclyl, each of which is independently unsubstituted or substituted with one, two or three substituents selected from a halogen group, a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, and an ester group;

or a pharmaceutically-acceptable salt thereof.

2. The composition of claim 1, wherein $R^1$ is aryl substituted with one, two or three substituents selected from alkylsulfonyl, alkoxy, alkylaminocarbonyl, deuterated alkoxy and (deuterated alkyl)aminocarbonyl.

3. The composition of claim 2, wherein $R^1$ is phenyl substituted with one, two or three substituents selected from $C_{1-4}$ alkylsulfonyl, $C_{1-4}$ alkoxy, $C_{1-4}$ alkylaminocarbonyl, deuterated $C_{1-4}$ alkoxy and (deuterated $C_{1-4}$ alkyl)aminocarbonyl.

4. The composition of claim 3, wherein $R^1$ is phenyl substituted with one, two or three substituents selected from methylsulfonyl, methoxy, methylaminocarbonyl, trideuteriomethoxy, and (trideuteriomethyl)aminocarbonyl.

5. The composition of claim 1, wherein $R^2$ is alkyl that is unsubstituted or substituted with halo.

6. The composition of claim 5, wherein $R^2$ is $C_{1-4}$ haloalkyl.

7. The composition of claim 6, wherein $R^2$ is 1,1,1-trifluoroethyl.

8. The composition of claim 1, wherein $R^4$ is 4-piperidinyl that is unsubstituted or substituted with one, two or three substituents selected from halo, $C_{1-4}$ alkyl, and $C_{1-4}$ alkoxy-(hydroxy)-$C_{1-4}$ alkyl.

9. The composition of claim 8, wherein $R^4$ is 4-piperidinyl substituted with fluoro and one or two additional substituents selected from methyl, trideuteriomethyl, tert-butyl, 2-hydroxy-methoxypropyl and 2-hydroxy-trideuteriomethoxypropyl.

10. The composition of claim 1, wherein each molecule is a compound of Formula (II):

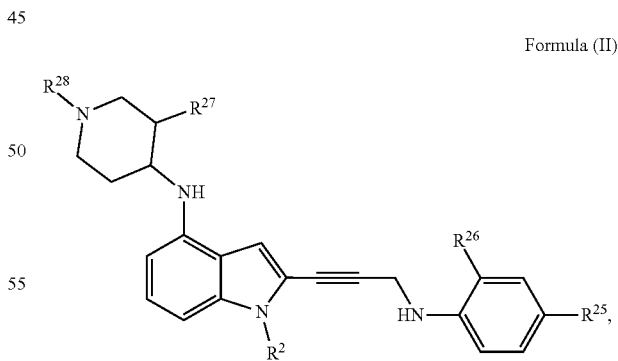

Formula (II)

wherein:
- $R^2$ is $C_1$-$C_4$ haloalkyl,
- $R^{25}$ is selected from hydrogen, a hydroxyl group, sulfhydryl group, halogen, amino group, nitro group, nitroso group, cyano group, azido group, sulfoxide group, alkyl sulfonyl group, sulfonamide group, carboxyl group, carboxaldehyde group, imine group, alkyl group, halo-alkyl group, alkenyl group, halo-alkenyl group, alkynyl group, halo-alkynyl group, alkoxy group, deuterated alkoxy group, aryl group, aryloxy group, aralkyl group, arylalkoxy group, heterocyclyl group, acyl group, acyloxy group, carbamate group, amide group, deuterated alkyl amide group, ureido group, epoxy group, and an ester group;

$R^{26}$ is selected from hydrogen, a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, alkenyl group, halo-alkenyl group, alkynyl group, halo-alkynyl group, alkoxy group, deuterated alkoxy group, aryl group, aryloxy group, aralkyl group, arylalkoxy group, heterocyclyl group, acyl group, acyloxy group, carbamate group, amide group, deuterated amide group, ureido group, epoxy group, and an ester group;

$R^{27}$ is selected from hydrogen, a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, and an ester group;

$R^{28}$ is selected from hydrogen, a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, deuterated alkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, and an ester group;

provided one or more of $R^{25}$, $R^{26}$, $R^{27}$ or $R^{28}$ is a deuterated group;

or a pharmaceutically-acceptable salt thereof.

11. The composition of claim 10, wherein:

$R^2$ is 1,1,1-trifluoroethyl;

$R^{25}$ is selected from $C_1$-$C_4$ alkylaminocarbonyl, deuterated $C_1$-$C_4$ alkylaminocarbonyl or $C_1$-$C_4$ alkylsulfonyl;

$R^{26}$ is $C_1$-$C_4$ alkoxy, or deuterated $C_1$-$C_4$ alkoxy;

$R^{27}$ is hydrogen or fluoro; and $R^{28}$ is selected from $C_1$-$C_4$ alkyl, $C_1$-$C_4$ alkoxy-$C_1$-$C_4$ alkyl optionally substituted with hydroxy, and deuterated $C_1$-$C_4$ alkoxy-$C_1$-$C_4$ alky optionally substituted with hydroxy.

12. The composition of claim 11, wherein:

$R^{25}$ is methylsuflonyl, methylaminocarbonyl, or trideuteriomethylaminocarbonyl;

$R^{26}$ is methoxy or trideuteriomethoxy; and $R^{28}$ is selected from methyl, tert-butyl, deuterated methyl, 2-hydroxy-1-methoxypropyl, and 1-trideuteriomethoxy-2-hydroxypropyl.

13. The composition of claim 10, wherein the compound has the formula:

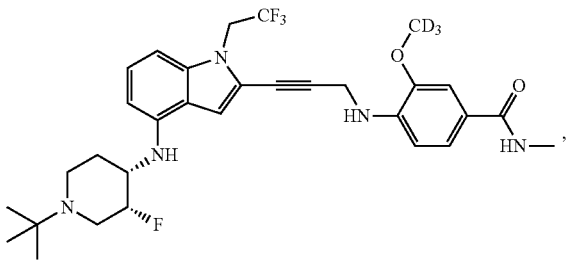

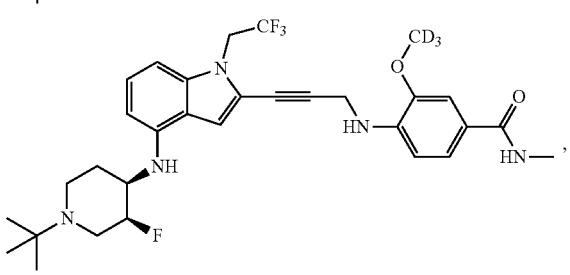

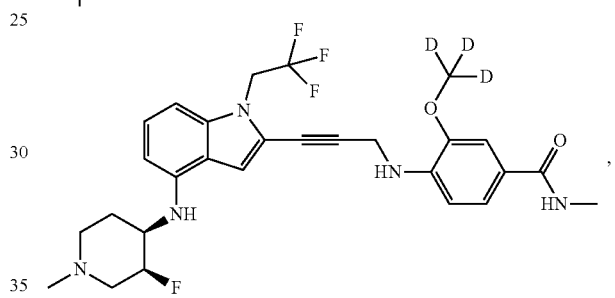

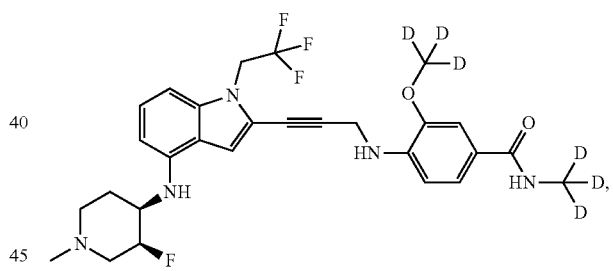

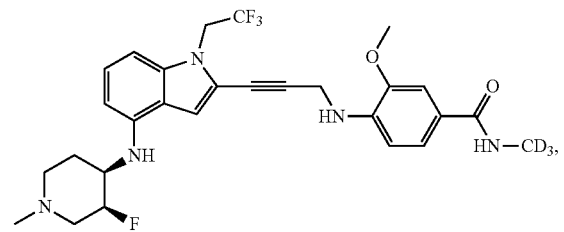

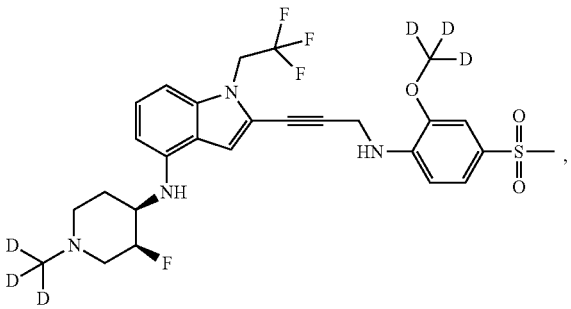

-continued
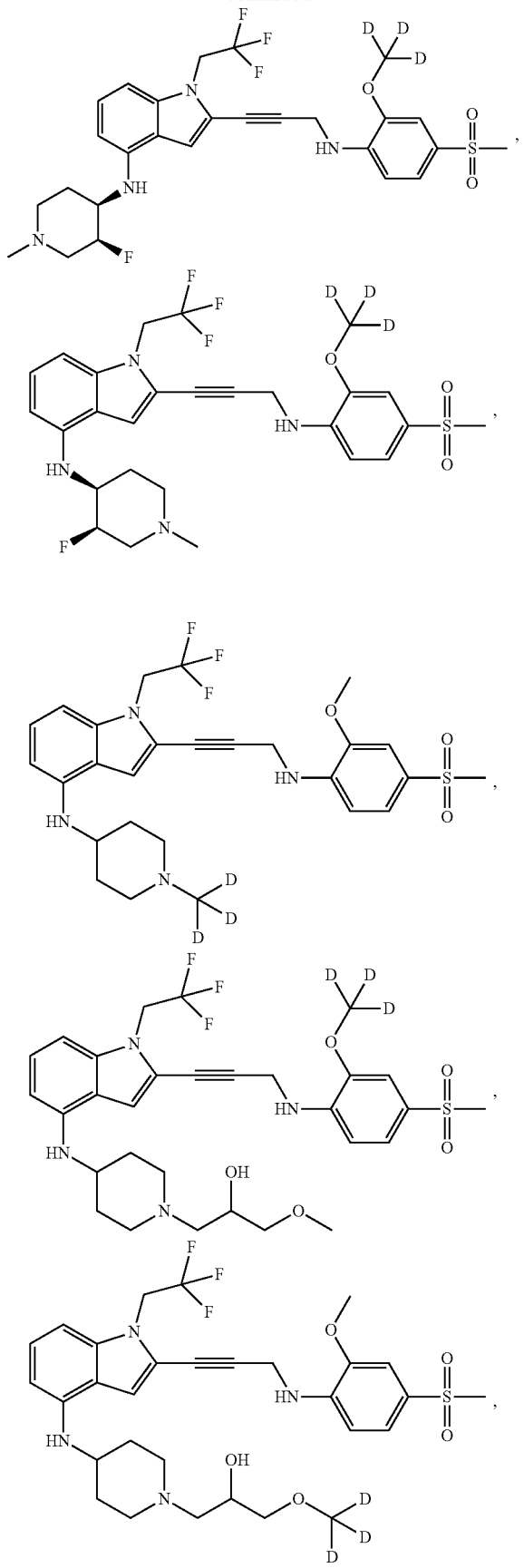
-continued
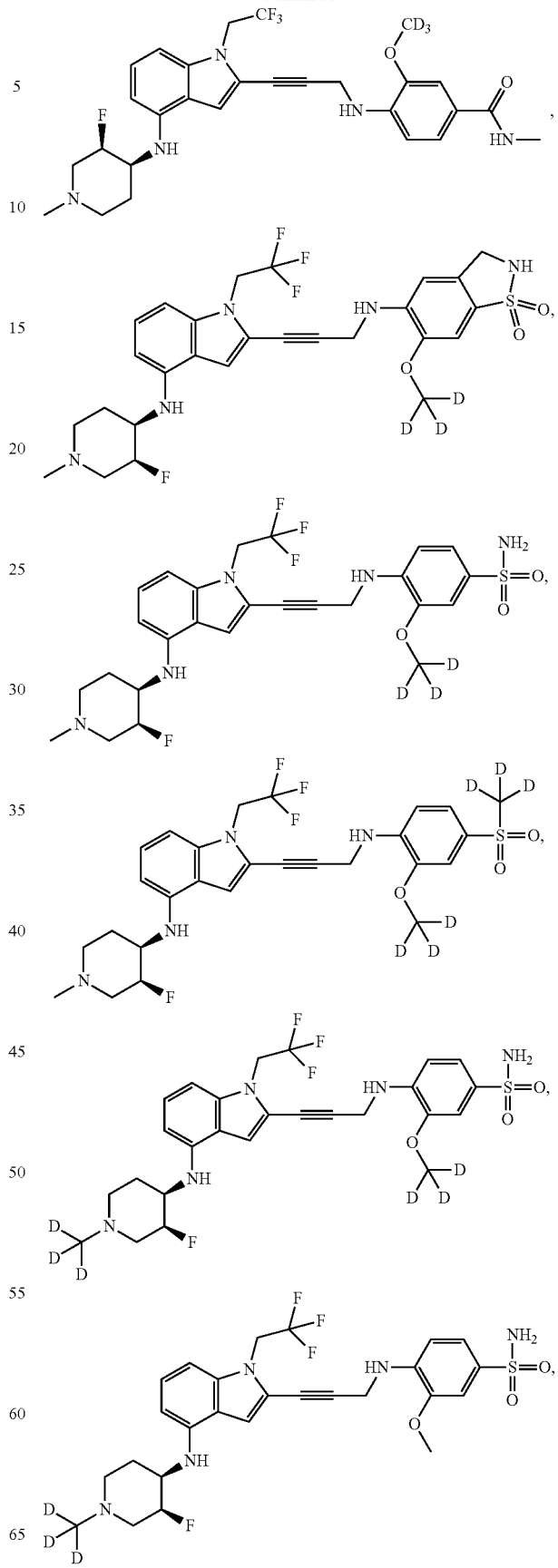

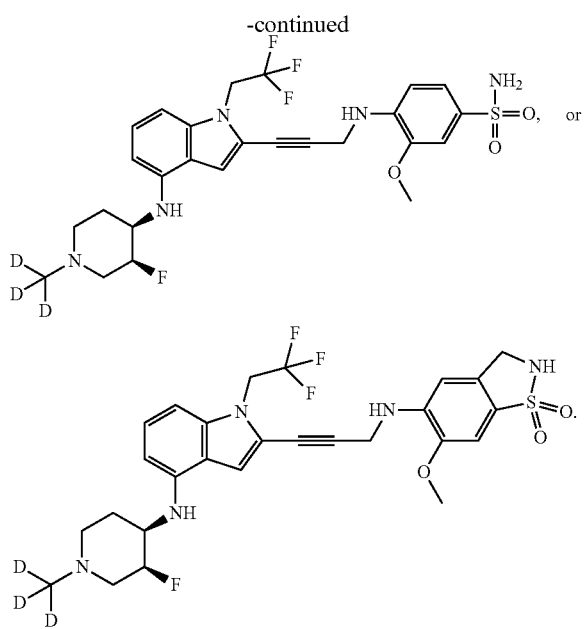

14. The composition of claim 1, wherein at least about 25% of the molecules in the population of molecules each independently comprise a deuterium atom.

15. The composition of claim 1, wherein at least about 95% of the molecules in the population of molecules each independently comprise a deuterium atom.

16. The composition of claim 1, wherein at least about 97% of the molecules in the population of molecules each independently comprise a deuterium atom.

17. A method of inducing apoptosis in a cell, the method comprising contacting the cell with a therapeutically-effective amount of the composition of claim 1.

18. The method of claim 17, wherein the compound of Formula (I) increases the ability of a p53 mutant to bind to DNA.

19. The method of claim 18, wherein the p53 mutant is p53 Y220C.

20. The method of claim 18, wherein the compound of Formula (I) induces a conformational change in the p53 mutant.

21. The method of claim 18, wherein the compound of Formula (I) increases a stability of a biologically-active conformation of the p53 mutant relative to a stability of the biologically-active conformation of the p53 mutant in an absence of the compound of Formula (I).

22. A method of treating a cancer, the method comprising administering to a subject in need thereof a therapeutically-effective amount of a composition of claim 1, wherein the compound of Formula (I) has an $SC_{150}$ value for p53 Y220C of less than 1 mM as measured by a homogeneous time-resolved fluorescence (HTRF) assay.

23. The method of claim 22, wherein the administering is intravenous.

24. The method of claim 22, wherein the administering is oral.

25. The method of claim 22, wherein the administering is intratumoral.

26. The method of claim 22, wherein the therapeutically-effective amount is from about 20 mg/kg to about 400 mg/kg.

27. The method of claim 22, wherein the cancer is breast cancer.

28. The method of claim 22, wherein the cancer is lung cancer.

29. The method of claim 22, wherein the compound of Formula (I) increases a stability of a biologically-active conformation of p53 Y220C relative to a stability of the biologically-active conformation of p53 Y220C in an absence of the compound of Formula (I).

30. The method of claim 22, wherein the compound of Formula (I) has an $SC_{150}$ value of less than about 50 nM.

31. A composition comprising a population of molecules, wherein the population of molecules has a mass of at least 1 μg, wherein at least 10% of the molecules in the population of molecules are a compound with a structure, wherein the structure is selected from:

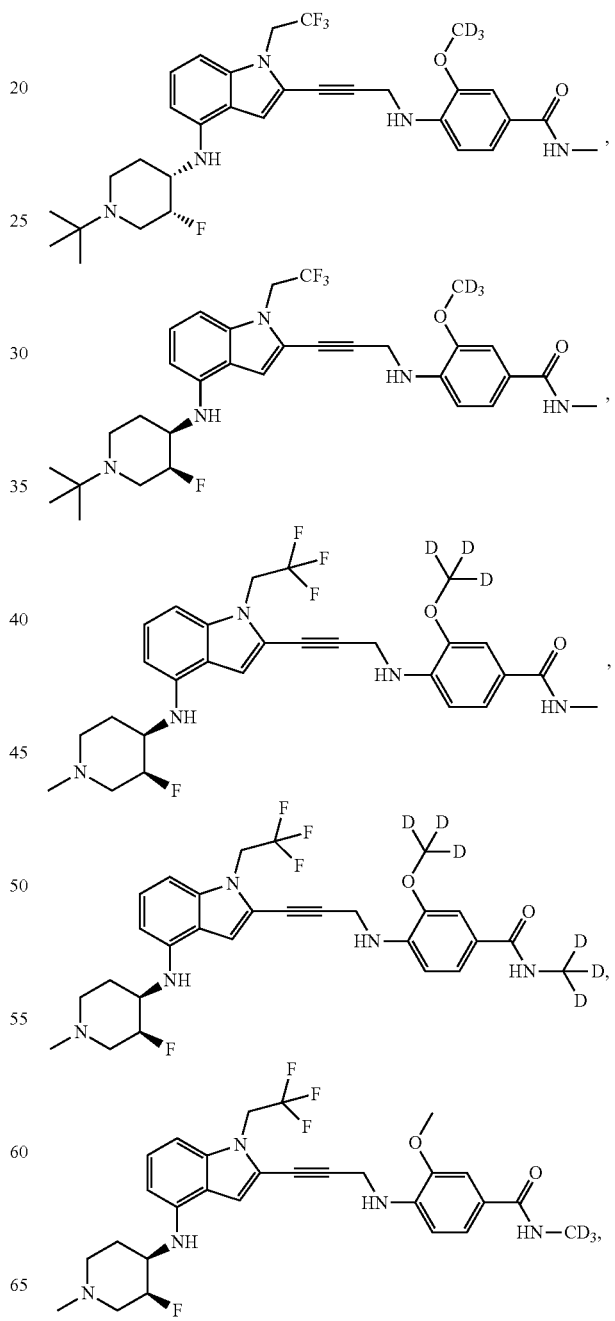

85
-continued
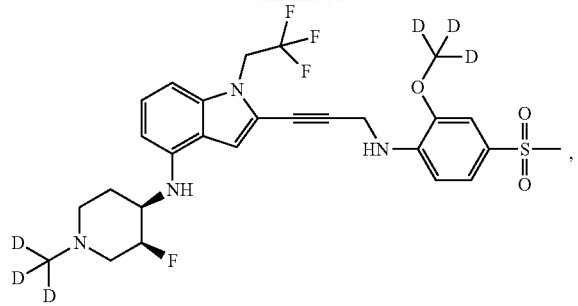
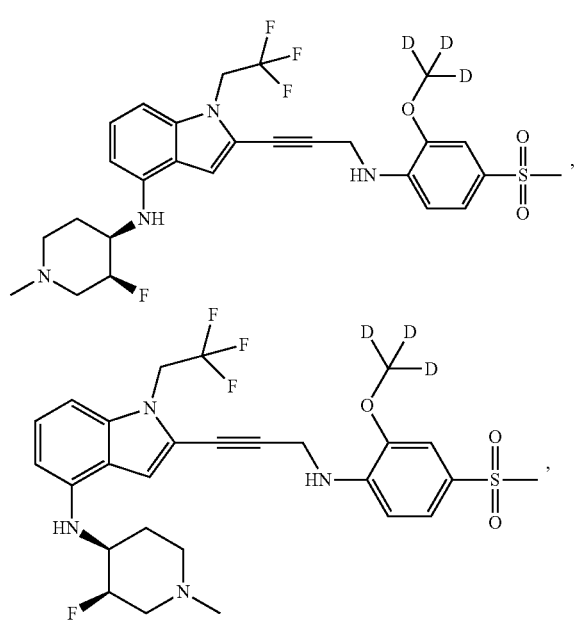
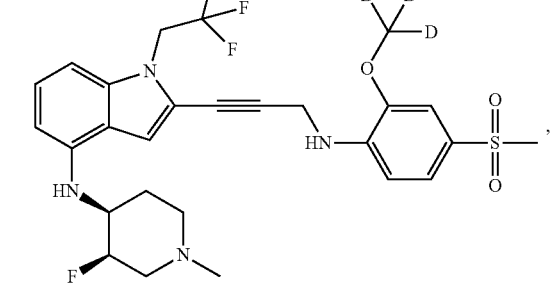
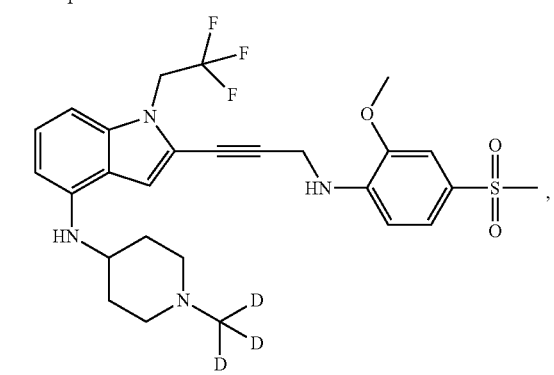
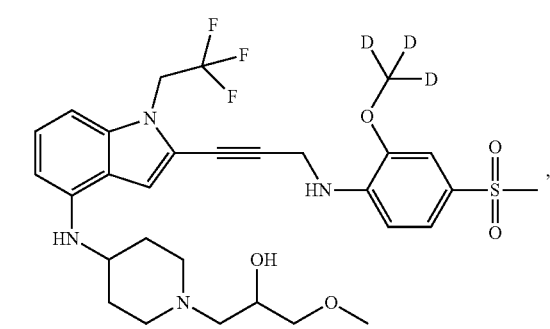
86
-continued
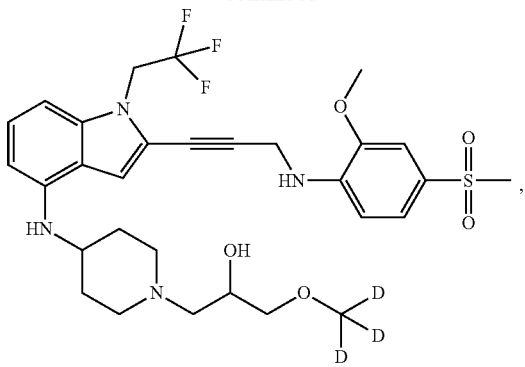
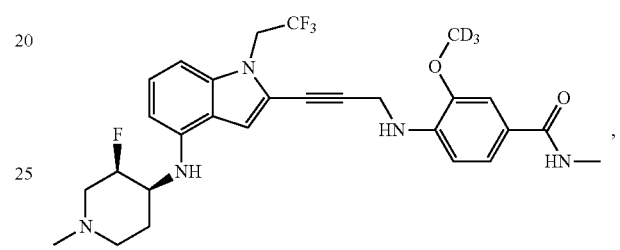
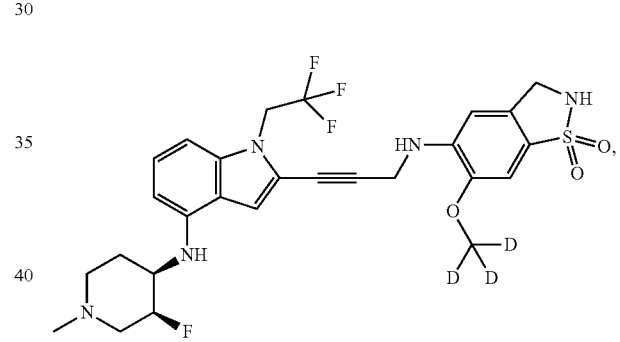
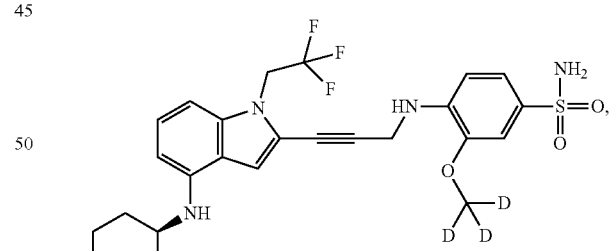
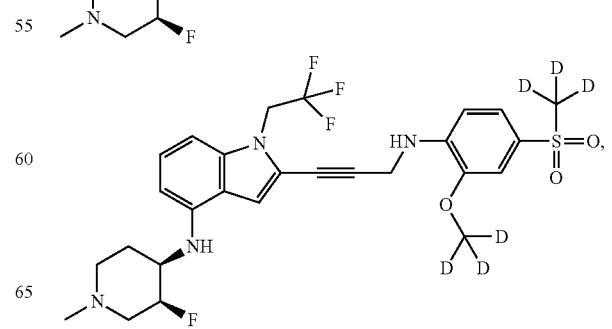

-continued
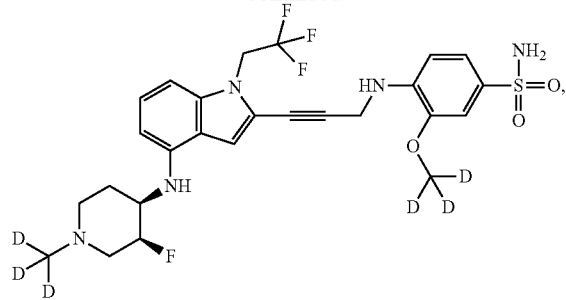
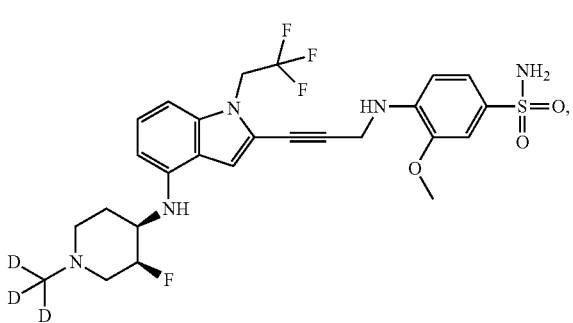
-continued
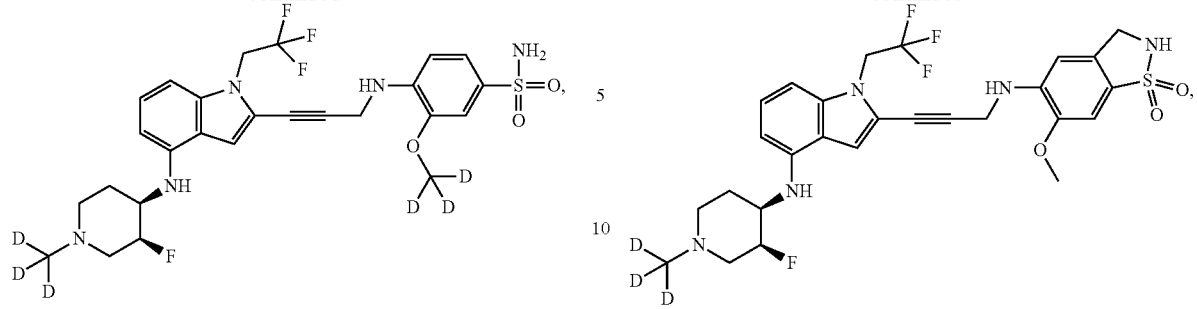
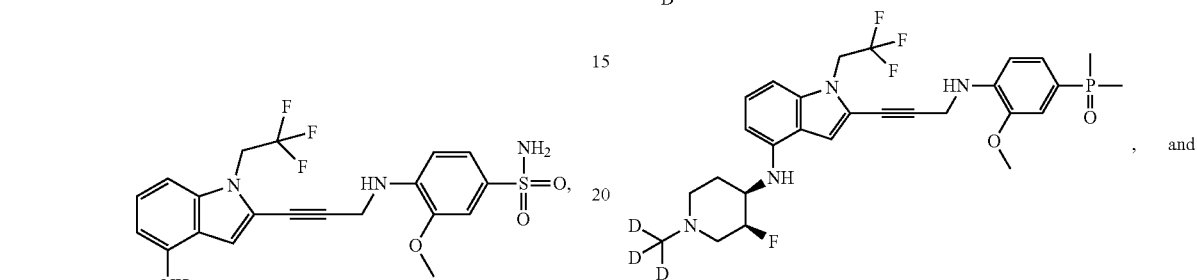
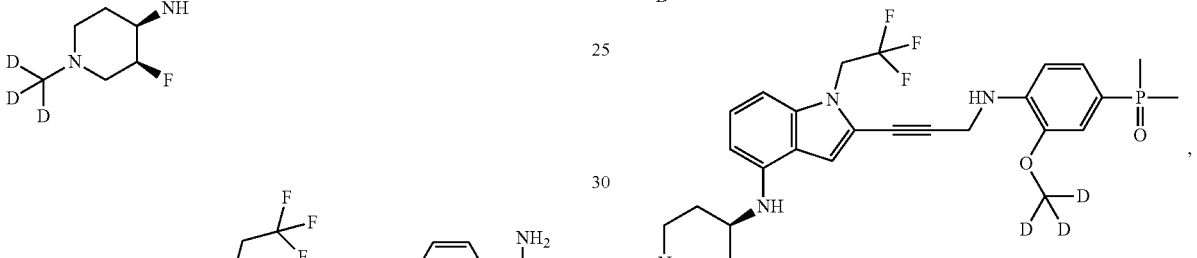
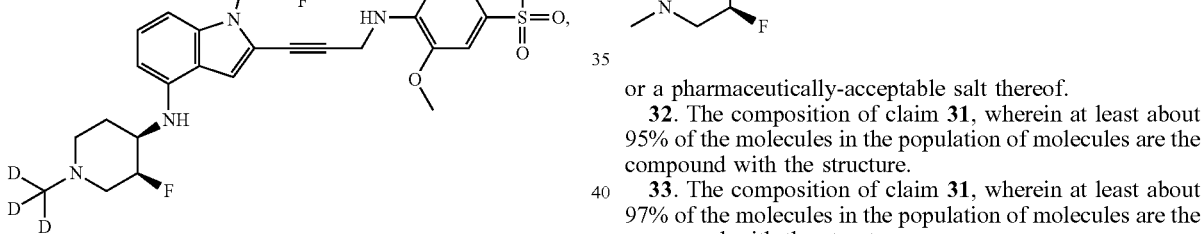
or a pharmaceutically-acceptable salt thereof.
32. The composition of claim 31, wherein at least about 95% of the molecules in the population of molecules are the compound with the structure.
33. The composition of claim 31, wherein at least about 97% of the molecules in the population of molecules are the compound with the structure.
* * * * *

UNITED STATES PATENT AND TRADEMARK OFFICE
CERTIFICATE OF CORRECTION

Page 1 of 2

PATENT NO. : 11,963,953 B2
APPLICATION NO. : 18/160060
DATED : April 23, 2024
INVENTOR(S) : Binh Vu It is certified that error appears in the above-identified patent and that said Letters Patent is hereby corrected as shown below:

In the Claims

Claim 11; Column 79; Line 56:
Delete:
"$C_1$-$C_4$ alkyl,"
And replace with:
--$C_1$-$C_4$ alkyl, deuterated $C_1$-$C_4$ alkyl,--

Claim 13; Column 82; Lines 56-67 and Column 83; Lines 1-13:
Delete:

"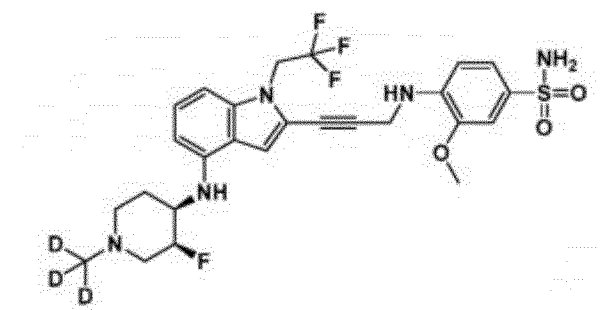

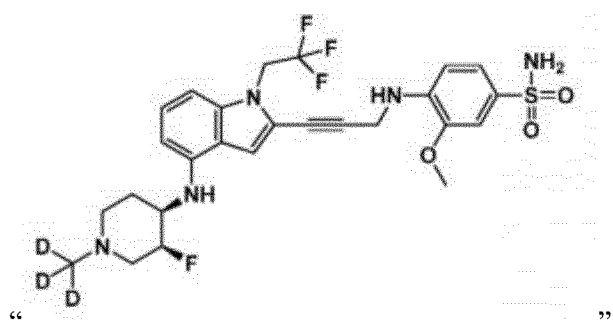

"

Signed and Sealed this
Ninth Day of July, 2024

*Katherine Kelly Vidal*

Katherine Kelly Vidal
*Director of the United States Patent and Trademark Office*

CERTIFICATE OF CORRECTION (continued)
U.S. Pat. No. 11,963,953 B2

And replace with:

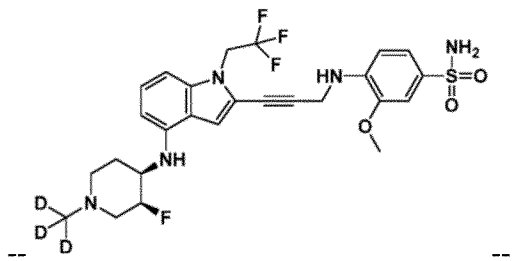

-- --

Claim 31; Column 87; Lines 30-43:
Delete:

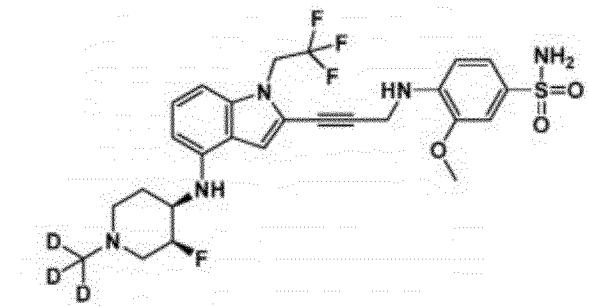

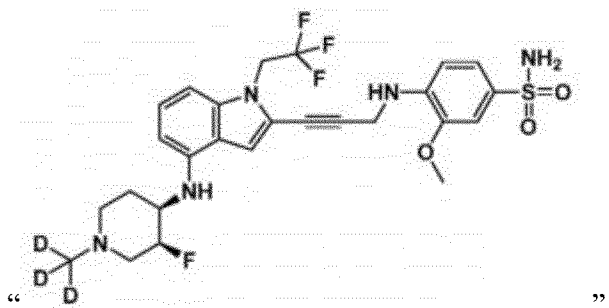

" "

And replace with:

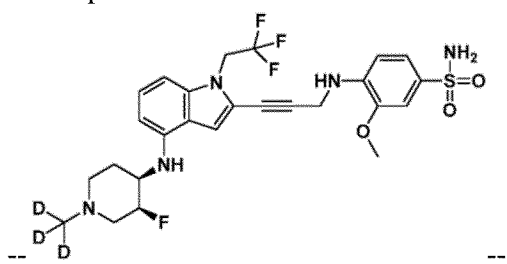

-- --

SEQUENCE LISTING

```
Sequence total quantity: 2
SEQ ID NO: 1              moltype = AA   length = 219
FEATURE                   Location/Qualifiers
source                    1..219
                          mol_type = protein
                          organism = synthetic construct
SEQUENCE: 1
SSSVPSQKTY QGSYGFRLGF LHSGTAKSVT CTYSPALNKM FCQLAKTCPV QLWVDSTPPP   60
GTRVRAMAIY KQSQHMTEVV RRCPHHERCS DSDGLAPPQH LIRVEGNLRV EYLDDRNTFR  120
HSVVVPCEPP EVGSDCTTIH YNYMCNSSCM GGMNRRPILT IITLEDSSGN LLGRNSFEVH  180
VCACPGRDRR TEEENLRKKG EPHHELPPGS TKRALSNNT                        219

SEQ ID NO: 2              moltype = DNA   length = 26
FEATURE                   Location/Qualifiers
source                    1..26
                          mol_type = other DNA
                          organism = Synthetic construct
SEQUENCE: 2
attaggcatg tctaggcatg tctagg                                       26
```